(12) United States Patent
Nishizawa et al.

(10) Patent No.: US 7,491,864 B2
(45) Date of Patent: Feb. 17, 2009

(54) ABSORBENT ARTICLE FOR BODY FLUIDS AND PRODUCTION METHOD THEREOF

(75) Inventors: Kazunori Nishizawa, Tochigi (JP); Tomotsugu Matsui, Tochigi (JP); Tomohiro Otani, Tochigi (JP); Yuka Kurita, Tochigi (JP)

(73) Assignee: DAIO Paper Corporation (JP)

( * ) Notice: Subject to any disclaimer, the term of this patent is extended or adjusted under 35 U.S.C. 154(b) by 503 days.

(21) Appl. No.: 10/467,150

(22) PCT Filed: Feb. 1, 2002

(86) PCT No.: PCT/JP02/00833

§ 371 (c)(1),
(2), (4) Date: Jan. 30, 2004

(87) PCT Pub. No.: WO02/062279

PCT Pub. Date: Aug. 15, 2002

(65) Prior Publication Data

US 2004/0127874 A1    Jul. 1, 2004

(30) Foreign Application Priority Data

| Feb. 2, 2001 | (JP) | 2001-026913 |
| Feb. 2, 2001 | (JP) | 2001-026914 |
| May 17, 2001 | (JP) | 2001-148131 |
| Jul. 26, 2001 | (JP) | 2001-226507 |
| Aug. 9, 2001 | (JP) | 2001-241912 |
| Oct. 10, 2001 | (JP) | 2001-312765 |
| Oct. 29, 2001 | (JP) | 2001-331564 |

(51) Int. Cl.
*A61F 13/15* (2006.01)
*A61F 13/20* (2006.01)

(52) U.S. Cl. .................. 604/367; 604/378; 604/385.01

(58) Field of Classification Search ................. 604/378, 604/368, 367, 364, 381–382, 385.01, 385.101
See application file for complete search history.

(56) References Cited

U.S. PATENT DOCUMENTS

| 2,681,032 A | * | 6/1954 | Shaw ......................... 116/200 |
| 3,717,150 A | * | 2/1973 | Schwartz .................... 604/372 |
| 4,213,459 A | * | 7/1980 | Sigl et al. ................... 604/380 |
| 4,269,188 A | * | 5/1981 | Nishizawa et al. .......... 604/368 |
| 4,357,938 A | * | 11/1982 | Ito et al. ..................... 604/376 |
| 4,418,524 A | * | 12/1983 | Ito et al. ....................... 57/239 |

(Continued)

FOREIGN PATENT DOCUMENTS

JP    54-152545    11/1979

(Continued)

*Primary Examiner*—Michele Kidwell
(74) *Attorney, Agent, or Firm*—Andrus, Sceales, Starke & Sawall, LLP

(57) ABSTRACT

An absorbent article for body fluids aimed at utilizing an entire absorbent member efficiently and having a thinner form, a larger absorption capacity and longer wearability as a whole is provided. The absorbent member 25 has a contraction material 27 which contracts itself on contacting urine passing through a liquid-permeable surface layer provided on the side facing to the body skin and an absorbent material for body fluids 26 which is practically united with the contraction material 27 is arranged on the upper side of a leak proof layer provided on the side farther from the body skin.

5 Claims, 45 Drawing Sheets

U.S. PATENT DOCUMENTS

| | | | | |
|---|---|---|---|---|
| 4,447,240 | A | * | 5/1984 | Ito et al. ................ 604/385.23 |
| 4,500,315 | A | * | 2/1985 | Pieniak et al. .............. 604/379 |
| 4,524,577 | A | * | 6/1985 | Ito et al. ...................... 57/200 |
| 4,623,342 | A | * | 11/1986 | Ito et al. ................ 604/385.23 |
| 4,809,493 | A | * | 3/1989 | Genba et al. .................. 57/238 |
| 4,942,089 | A | * | 7/1990 | Genba et al. ................ 428/364 |
| 5,143,776 | A | * | 9/1992 | Givens ....................... 428/194 |
| 5,175,046 | A | * | 12/1992 | Nguyen ...................... 428/198 |
| 5,411,497 | A | * | 5/1995 | Tanzer et al. ................ 604/368 |
| 5,593,400 | A | * | 1/1997 | O'Leary ................ 604/385.27 |
| 5,885,264 | A | * | 3/1999 | Matsushita .................. 604/361 |
| 5,891,124 | A | * | 4/1999 | Nomura et al. ........ 604/385.23 |
| 6,056,732 | A | * | 5/2000 | Fujioka et al. ......... 604/385.01 |
| 6,423,883 | B1 | * | 7/2002 | Morman et al. ............. 604/368 |
| 6,432,094 | B1 | * | 8/2002 | Fujioka et al. ......... 604/385.01 |
| 6,432,097 | B1 | * | 8/2002 | Ahr et al. ................ 604/385.19 |
| 2002/0128616 | A1 | * | 9/2002 | Morman et al. ............. 604/364 |
| 2003/0120231 | A1 | * | 6/2003 | Wang et al. ................. 604/368 |
| 2004/0243085 | A1 | * | 12/2004 | Veith et al. ............... 604/385.3 |

FOREIGN PATENT DOCUMENTS

| | | |
|---|---|---|
| JP | 63-12704 | 1/1988 |
| JP | 6-102068 | 12/1994 |
| JP | 2656245 | 5/1997 |
| JP | 11-506963 | 6/1999 |
| JP | 11-200209 | 7/1999 |
| JP | 2000-24033 | 1/2000 |
| JP | 2000-24033 | 4/2000 |
| JP | 2000-102562 | 4/2000 |
| JP | 2000-510031 | 8/2000 |
| JP | 2000-510033 | 8/2000 |
| WO | WO 9734559 A1 * | 9/1997 |
| WO | WO 9745082 A1 * | 12/1997 |

* cited by examiner

ABSORBENT ARTICLE FOR BODY FLUIDS AND PRODUCTION METHOD THEREOF

CROSS REFERENCE TO RELATED APPLICATION

The present application is the U.S. national stage application of International Application PCT/JP02/00833, filed Feb. 01, 2002, which international application was published on Aug. 15, 2002 as International Publication WO 02/062279. The International Application claims priority of Japanese Patent Application 2001-26913, filed Feb. 2, 2001; Japanese Patent Application No. 2001-26914, filed Feb. 2, 2001; Japanese Patent Application No. 2001-148131, filed May 17, 2001; Japanese Patent Application No. 2001-226507, filed Jul. 26, 2001; Japanese Patent Application No. 2001-241912, filed Aug. 9, 2001; Japanese Patent Application No. 2001-312765, filed Oct. 10, 2001; and Japanese Patent Application No. 2001-331564, filed Oct. 29, 2001.

TECHNICAL FIELD

This invention relates to absorbent articles for body fluids such as paper diaper and sanitary napkin for absorbing and containing body fluids.

BACKGROUND ART

Absorbent articles for body fluids such as paper diaper and sanitary napkin basically comprise a liquid-permeable surface layer arranged on the side facing to the body skin, a leakproof layer arranged on the side farther from the body skin and an absorbent portion for body fluids arranged there between.

In these articles, a variety of constructions are known for the absorbent portion for body fluids and mainly an absorbent paper made of highly absorbent polymer, flocculent pulp (flap pulp), crepe paper or the like is used as an absorbent material. In accordance with recent progress in the technology of highly absorbent polymer, it has become possible to construct the absorbent portion for body fluids in a thinner form, and thus, body fitness of the absorbent portion of the product has been improved and leakage of body fluids has been lessened.

The improvement in the absorbent property of the product triggers a demand of further development of a new product being in a thinner form and having a larger absorption capacity and longer wearability by consumers.

In order to fulfill such a demand, it is necessary that the absorbent portion for body fluids must absorb all volume of, for example, urine excreted many times. However, as urination is repeated, the rate of absorption of the absorbent portion for body fluids becomes slower, and in particular, absorption of body fluids often does not extend to the end part of the longitudinal direction of the absorbent portion for body fluids. This is considered to be due to insufficient diffusion of body fluids to the longitudinal direction (the longitudinal direction of product) and occurrence of a so-called gel blocking phenomenon which blocks wetting expansion due to swelling of the highly absorbent polymer.

In order to solve these phenomena, there are proposed the technique to promote the longitudinal wetting expansion disclosed in Kohyo (Jpn. unexamined patent publication) No. 2000-510031, Kohyo (Jpn. unexamined patent publication) No. 2000-510033 and the like, the technique to block gel blocking of the highly absorbent polymer disclosed in Kohyo (Jpn. unexamined patent publication) No. 2000-510031, Kohyo (Jpn. unexamined patent publication) No. 2000-510033 and the like, the design of both shape of the highly absorbent polymer and the arrangement thereof, the method for securing spaces to be occupied by swelling of the highly absorbent polymer on wetting, and the like.

The use of any methods described above, however, can not provide a satisfactory solution for the problems. Upon consideration of this cause again, the absorbent portion for body fluids of the conventional absorbent articles for body fluids was found to be based on the premises that body fluids from excretory part would wet and extend (diffuse) to the end of the longitudinal direction by making it lengthwise, arranging it along the longitudinal direction of the product, and designing its approximate center to be located at the excretory part of body fluids. Therefore, body fluids practically can not be absorbed by the entire absorbent portion for body fluids as long as body fluids do not diffuse to the longitudinal direction sufficiently.

DISCLOSURE OF INVENTION

Accordingly, the problem to be solved by the present invention is to provide, with consideration given to the limit of diffusion of body fluids in the absorbent portion for body fluids, absorbent articles for body fluids in which the whole part of an absorbent member is efficiently utilized by constructing in a way that an absorption part of body fluids is displaced by the use of a contraction material which contracts on contacting body fluids, thereby resulting in a thinner form, a larger absorption capacity and longer wearability as a whole.

Another problem to be solved is that the absorption part is made renewable against the excretory part of body fluids in association with excretion of body fluids. Still another problem to be solved is to provide the absorbent articles for body fluids free from a so-called gel blocking phenomenon that blocks wetting expansion at the time of swelling of a highly absorbent polymer, thereby allowing the function of the highly absorbent polymer to be fully fulfilled.

The absorbent articles of the present invention for body fluids for absorbing and retaining body fluids where these problems have been solved are provided, in a contractible way, with an absorbent member which contracts on contacting body fluids.

When the absorbent member which contracts on contacting body fluids is provided in a contractible way, the part of the absorbent member which previously absorbed body fluids becomes displaced from the excretory part of the body fluids and in turn, a new part of the absorbent member is located since the absorbent member contracts on contacting body fluids. In other words, the absorption part of the absorbent member is renewed and displaced against the excretory part of the body fluids in accordance with the excretion of the body fluids. Therefore, the whole part of the absorbent member can be efficiently utilized and, as a whole, the absorbent articles for body fluids being in a thinner form and having a larger absorption capacity and longer wearability can be obtained.

This kind of the absorbent articles for body fluids are generally provided with a liquid-permeable surface layer arranged on the body skin-facing side, a leakproof layer arranged on the side farther from the body skin and an absorbent portion for body fluids arranged there between. A preferable embodiment proposed in this case is constructed such that the contraction material with a predetermined length which contracts on contacting body fluids and the absorbent member made of the absorbent material for body fluids practically united with the contraction material are arranged in the absorbent portion for body fluids so that the contraction material may contract. In this case, the contraction of the contraction material by contacting body fluids is accompanied by the contraction of the absorbent material for body fluids practically united therewith. Accordingly, the aforementioned renewal function of the present invention is fulfilled.

In the present invention, the absorbent member is made contractible against the article. This most preferable embodiment is the one in which one end of the absorbent member is fixed to the article. In this case, the absorbent member contractively moves by the contraction toward the fixing part of the article. Also in this case, the other end of the absorbent member is made either to be in a free unfixed end or to be provisionally fixed to the article so as to be released in association with the contraction of the absorbent member.

In the present invention, the construction where a plurality of the absorbent members are arranged side by side and their fixing parts are selectively provided on one end and the other end in the arrangement direction may be adopted.

The absorbent member of the present invention may comprise the contraction material with a predetermined length which contracts on absorbing body fluids and the absorbent material for body fluids practically united with the contraction material. In this case, the absorbent member may be constructed such that the absorbent material for body fluids comprising both the highly absorbent polymer and a retaining carrier thereof and the contraction material are provided and this contraction material is practically united with the absorbent material for body fluids. Further in this case, a preferable embodiment is constructed such that the highly absorbent polymer is arranged intermittently on the carrier in the direction of contraction. In the place where the highly absorbent polymer is not arranged, swelled highly absorbent polymer is free from mutual interference and the contraction is not inhibited.

The embodiment of this intermittent arrangement of the highly absorbent polymer may preferably adopt a construction where the carrier of the highly absorbent polymer is made in a pouch-like form extending to the direction of the contraction and the highly absorbent polymer is arranged therein intermittently in the direction of the contraction. In this instance, the highly absorbent polymer is securely retained within the carrier and free from falling off the carrier. In addition, the pouch-like carrier can retain a larger amount of the highly absorbent polymer in one place.

Further, the embodiment of this intermittent arrangement of the highly absorbent polymer may fulfill effective prevention of the aforementioned inhibition of contraction without fail as long as the length in the direction of contraction of the part where the highly absorbent polymer is not arranged is adjusted to be from 30 to 400% of the length in the direction of contraction of the part where the highly absorbent polymer is arranged.

Still further, the embodiment of this intermittent arrangement of the highly absorbent polymer may preferably adopt a construction where the contraction material is fixed to the part arranged with the highly absorbent polymer in the direction of contraction and is not fixed to the part not arranged with the highly absorbent polymer. That is, the contraction material hardly contracts at the part fixed to carrier of the absorbent material for body fluids and also the polymer-arranged part of the carrier hardly contracts as described above. Accordingly, in these constructions, both the contraction material and the absorbent material for body fluids may be allowed to contract efficiently.

In the embodiment where the pouch-like carrier of the present invention is used, the intermittent arrangement described above may not be necessarily adopted.

Further, the embodiment where the pouch-like carrier is used may preferably use the pouch-like carrier which is formed in a shape extending to the direction of the contraction of the absorbent member and which may be expanded by swelling of the highly absorbent polymer therein. There is an advantage, brought about by the use of the pouch-like carrier, that a larger amount of the highly absorbent polymer may be arranged in one part, whereas when body fluids are supplied, the polymer having swelled earlier in said arranged part tends to block the supply of the body fluids to the rest of the unswelled polymer. The prevention of this may be to form a larger size of the pouch-like carrier in consideration of the swelling volume of the highly absorbent polymer. However, the highly absorbent polymer increases its volume up to about 50-fold at the maximum after absorbing body fluids and when this is taken into consideration, the width of the pouch-like carrier becomes too large, rendering it difficult to contain the highly absorbent polymer within an objective setting space of the article. In contrast, the use of an expandable pouch-like carrier according to the present invention makes the setting space required initially for the pouch-like carrier small as well as hardly permits local gel blocking to occur because the pouch-like carrier expands concurrently with the swelling of the highly absorbent polymer.

For this purpose, a construction where the pouch-like carrier is arranged in the article in a state folded back toward the width direction orthogonal to the direction of contraction so as to be opened by swelling of the highly absorbent polymer at the folded-back portions of the pouch-like carrier for restoration and expansion as well as the pouch-like carrier is arranged in the article in the folded state to have a width not larger than one half of the width in the unfolded state may be adopted. In this case, the pouch-like carrier may be constructed so that it may be arranged in the article in a state that both side ends of the pouch-like carrier are folded back toward the central side of the width direction respectively.

Another embodiment may adopt a construction where the pouch-like carrier is provided with tucks so as to be expanded and extended by swelling of the highly absorbent polymer in the pouch-like carrier.

Still another embodiment may adopt a construction where the expansion of the pouch-like carrier to the width direction is restrained. When the expansion of the pouch-like carrier to the width direction is restrained, the space occupied by the carrier does not change before and after swelling, and therefore the pouch-like carrier may be placed in proximity to each other.

In the absorbent member of the present invention comprising the contraction material and the absorbent material for body fluids, when the contraction material is arranged at the center of the width direction of the absorbent material for body fluids, the contraction of the contraction material acts uniformly on the absorbent material for body fluids in the width direction, thereby allowing the absorbent member to preferably contract linearly.

In the absorbent member of the present invention in which the contraction material and the absorbent material for body fluids are united by being fixed to each other, it is difficult for the contraction material to contract at the part fixed to the carrier of the absorbent material for body fluids. Accordingly, it is preferable that the contraction material and the absorbent material for body fluids are practically united by being fixed intermittently to each other in the longitudinal direction.

A preferable embodiment for the absorbent material for body fluids of the present invention may make use of a thread-like or string-like material which is made of a fibrous, highly absorbent polymer having a capacity of absorbing body fluids more than 10 times its own weight. In a preferable embodiment in this case, the contraction material and the absorbent material for body fluids are practically united by being bundled and fixed to each other intermittently in the longitudinal direction.

When the absorbent material for body fluids expands by absorbing body fluids as described above, the contraction of the contraction material practically united with the former is inhibited. Accordingly, it is preferable that the contraction material and the absorbent material for body fluids are constructed so as to be separated from each other at the portion contacting body fluids. However, it is also possible in the present invention that the contraction material and the absorbent material for body fluids are constructed so as not to be separated from each other.

In order to achieve this separation, specifically, the contraction material and the absorbent member for body fluids are constructed to be united by bonding to each other so that the bonding part may be separated upon contacting body fluids. In this case, when the bonding force at the aforementioned bonding part under the state not contacting body fluids is made 2-fold higher than the bonding force of the bonding part on contacting body fluids, the bonding force at the part where body fluids has not been absorbed yet is sufficient and the part would not separate inadvertently.

The bonding of the contraction material to the absorbent material for body fluids may be carried out with a water-dispersion type hot melt adhesive or water-soluble adhesive. The bonding pattern may be made linear, plane-wise or point-wise.

The absorbent member of the present invention may be composed of only a thread-like or string-like member made of a fibrous highly absorbent polymer which has a capacity of absorbing body fluids more than or equal to 10 times as large as its own weight and contracts by absorbing body fluids. In this case, the decrease in the number of parts and cost and a thinner construction of the absorbent member may be achieved.

On the other hand, an improvement in the aforementioned renewal function and additions of other functions may be achieved by an improvement in the construction other than the absorbent member.

For example, there is a preferable improvement in the construction where the use-surface side sheet permeable to body fluids and the back-surface side sheet are provided, the use-surface side sheet and the back-surface side sheet are provided with fixing parts at places spaced in the width direction of the product along the longitudinal direction, thereby forming channel spaces between the adjacent fixing parts along the longitudinal direction, and the absorbent member is arranged within the channel spaces. In this instance, the diffusion of body fluids are facilitated due to the presence of the channel spaces, and the supply of body fluids to the absorbent member becomes smooth. At the same time, there is an improvement in cushioning owing to the sheets forming these channel spaces.

Further, an assured supply of body fluids to the absorbent member may be achieved, for example, by providing a liquid-retaining member in contact with the absorbent member. This design is particularly useful when the absorption rate of the absorbent material for body fluids is fast due to the fact that it contains highly absorbent polymer and the like. Namely, when body fluids have been absorbed and retained by the absorbent material for body fluids before contacting the contraction material, the supply of body fluids to the contraction material becomes insufficient, possibly resulting in an insufficient contraction of the contraction material.

The liquid-retaining member of the present invention may be made of thin paper or nonwoven fabric. When the liquid-retaining member is used, it is preferable that one end of the absorbent member is fixed to the article and the liquid-retaining member is localized on the side of the fixed end of the absorbent member. That is, when one end of the absorbent member is fixed to the article, it is better for the part on the fixed side of the absorbent member to be supplied with body fluids since the absorbent member having contacted body fluids moves toward its fixed side. Accordingly, the liquid-retaining member may act more efficiently by a localized placement of the liquid-retaining member on the side of the fixed end of the absorbent member.

When the absorbent member is constructed by being provided with the absorbent material for body fluids comprising both the highly absorbent polymer and its retaining carrier and the contraction material, and when the absorbent material for body fluids and the contraction material are practically united with each other, it is preferable that the contraction material is arranged to be interposed between the liquid-retaining member and the carrier or that the liquid-retaining member is constructed in such a way that it does not protrude from the side edges of the carrier and practically covers the contraction material in the entire width direction. Thereby, the supply of body fluids to the contraction material is made further smooth and secure.

Further, when the absorbent article for body fluids has a liquid-permeable surface layer provided on the side facing the body skin, a leakproof layer provided on the side farther from the body skin and the absorbent portion for body fluids interposed there between, it is preferable that the absorbent member of the present invention is arranged on the leakproof layer by interposition of the liquid-retaining member. Thereby, the supply of body fluids to the absorbent member is further made smooth and secure.

Since the absorbent member of the present invention contractibly moves, it is preferable that a reduction in the moving resistance thereof leads to an improvement in the renewal function. For this purpose, it is possible to adopt a construction where a plurality of cushion members are arranged and also the absorbent member is arranged between the cushion members in the article. In this instance, the absorbent member is present between the cushion members, and even if an external pressure is applied to these members, the pressure is sustained mainly by the cushion members, and therefore, the moving resistance of the absorbent member is not elevated. Thereby, the absorbent member can contractively move in an effective fashion.

It is preferable that the cushion member is in a shape extending toward the longitudinal direction of the product and that a plurality of the cushion members are arranged intermittently with a spacing in the width direction of the product.

As the cushion member, it is preferable for the cushion member to be formed such that an absorbent cushioning material for body fluids is enclosed within a closed pouch-like body composed of a sheet permeable to body fluids. In this case, the cushion member not only serves as the aforementioned cushioning function but also an absorbent function for body fluids.

Further, it is possible to adopt a construction where the pouch-like body of the cushion member is partitioned to have a plurality of compartments and the aforementioned absorbent cushioning material for body fluids is enclosed within each compartment. Thereby, the cushioning material is hardly maldistributed within the pouch-like body. In this instance, the partition is preferably constructed so as to be removed by contacting body fluids. Thereby, it is possible that the removal of the partition upon contacting body fluids may result in deformation to a more stable shape, preventing at the same time the cushioning material initially from being unevenly distributed.

In order to make the partition of the pouch-like body removable by contacting body fluids, it is preferable that the partition is made by bonding the inside surfaces of the pouch-like body to each other using a water-dispersion type hot melt adhesive or water-soluble adhesive.

As mentioned heretofore, the essence of the present invention is to use the absorbent member which contracts on contacting body fluids. As long as this absorbent member is used, non-contractible absorbent materials which absorbs body fluids but does not contract may be provided.

On the other hand, the production of the absorbent article for body fluids of the present invention may make use of a general construction method being used in the field of this kind of absorbent articles for body fluids. That is, this kind of absorbent articles for body fluids are continuously produced, on the production line, generally by attaching their parts so as to be stacked in turn from the lower part. According to this basic procedure in the present invention as well, a continuous form of the contractive absorbent member is produced in bulk in advance, cut off in a predetermined length one after another, arranged on a suitable place of the objective attachment part moving down on the production line, and then fixed by being provided with the fixing part as needed. The absorbent member having been produced on a separate line and wound on a roll in advance may be set on an assembly line, or the production line of the absorbent member may be connected to the assembly line to avoid the winding process.

Particularly when the absorbent member having the aforementioned expandable pouch-like carrier is arranged in the folded state, the construction is carried out in a way that the absorbent member is attached to the objective part for attaching while being folded in the width direction orthogonal to the direction of contraction or being provided with tucks on the pouch-like carrier. Prior to the folding in this case, a plurality of seal parts where the surfaces opposite to each other of the thickness direction of the pouch-like carrier are bonded to each other in a continuous line-wise manner from one end to the other end of the width direction may be provided with a spacing in-between in the direction of contraction of the contraction material. In thus-formed absorbent member, the inner space of the pouch-like carrier is partitioned by the seal parts, while the lateral expansion is not restrained at the time of swelling.

In contrast, in order to restrain the lateral expansion of the absorbent member at the time of swelling, a plurality of the seal parts where the surfaces opposite to each other of the thickness direction of the pouch-like carrier are bonded to each other in a continuous linear manner from one end to the other end of the width direction are provided with a spacing in-between in the direction of contraction of the absorbent member after having folded the absorbent member or formed tucks on the absorbent member.

MODES FOR CARRYING OUT THE INVENTION

Several embodiments of the present invention will hereinafter be described further in detail with reference to the accompanying drawings.

The present invention is applicable, in general, to articles for absorbing body fluids, for example, disposable paper diapers, disposable sanitary napkins and the like. It should be noted that once an embodiment for so-called tape-type paper diapers of which both side ends on the back are brought over to the right and left front abdominal sides and fixed with a tape fastener (including an adhesive tape fastener and a hook-and-loop fastener) is explained, embodiments for disposable underwear-type diapers or disposable pad-type absorbent articles and for sanitary napkins seem to be readily conceivable, and therefore, examples for the latter two are omitted.

1 First Embodiment 1.1 Example of Tape-type Paper Diaper

Figure 1:
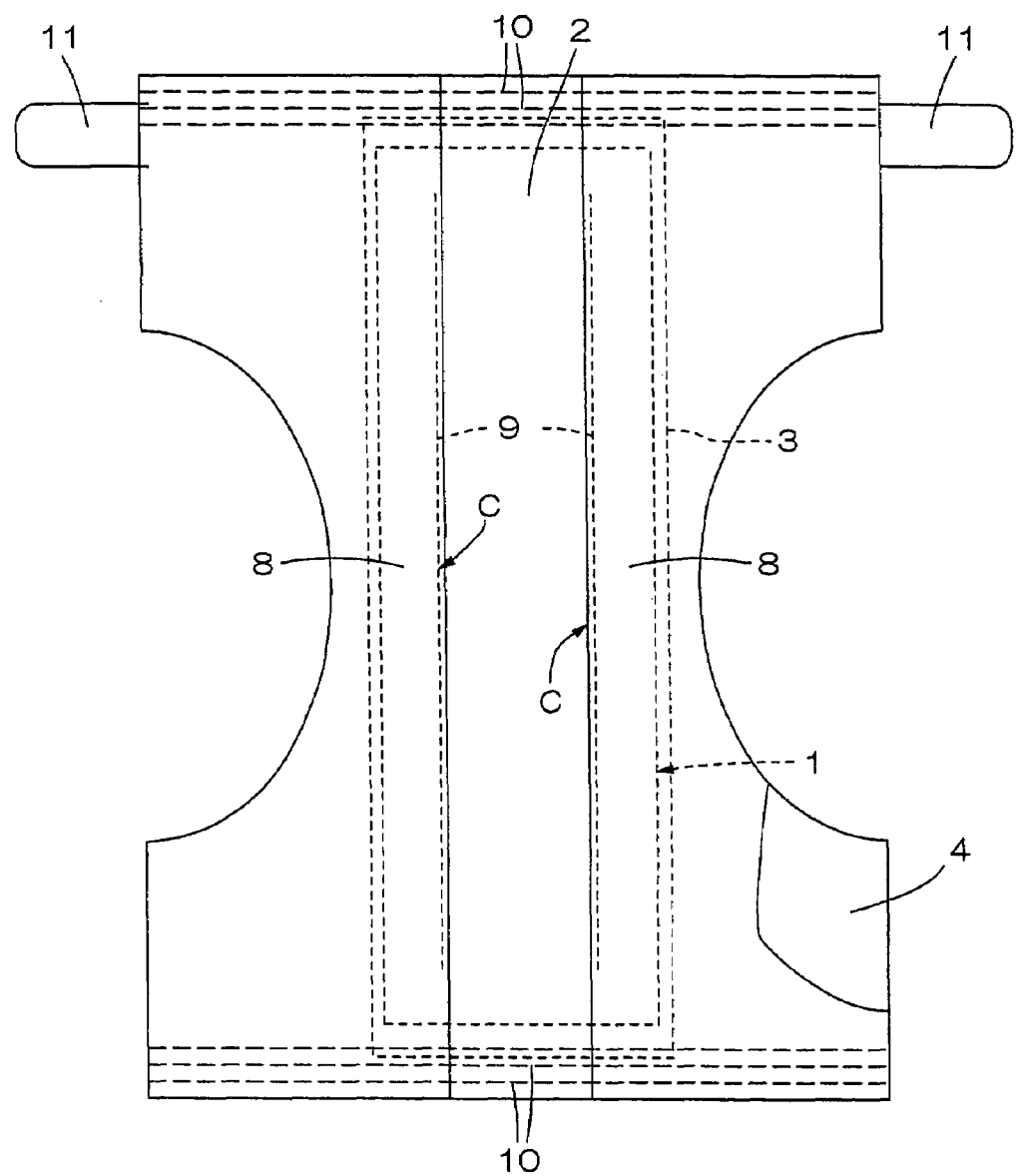
FIG. 1 is a plan view of a disposable paper diaper in a developed state.
Figure 2:
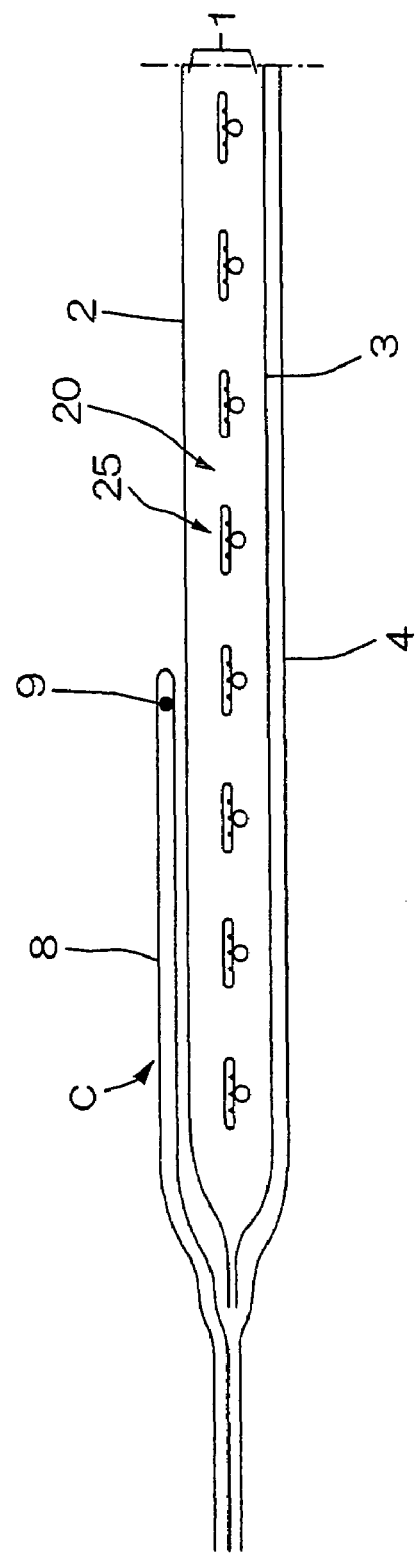
FIG. 2 is a longitudinal cross sectional view of a main part of FIG. 1.
Figure 3:
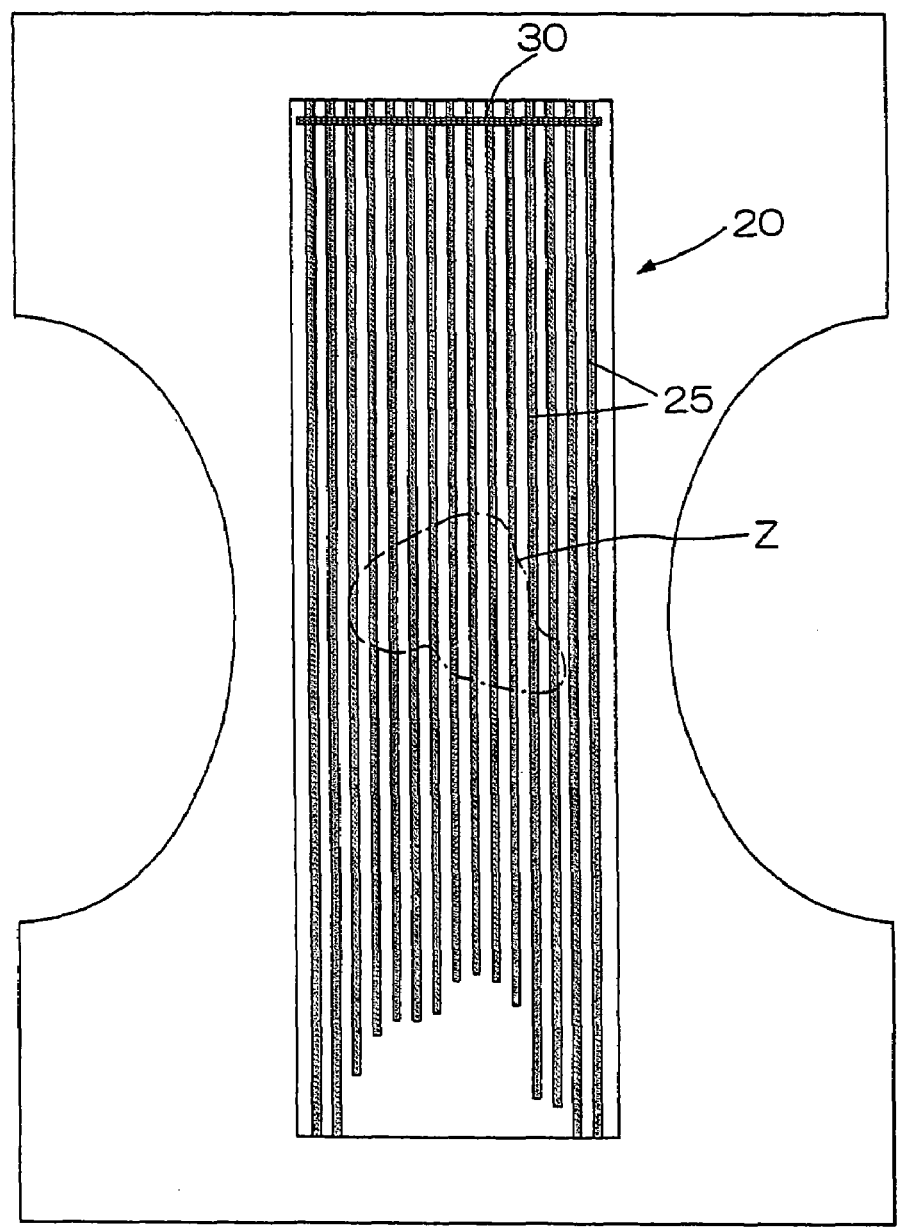
FIG. 3 is a schematic plan view showing a state at the time of absorbing body fluids.

FIG. 1, FIG. 2 and FIG. 3 illustrate an example of a disposable diaper applied to the present invention. As shown in FIG. 1 and FIG. 2, this disposable diaper comprises liquid-permeable non-woven fabric, porous film or the like which is provided on the side facing the body skin, a rectangular surface sheet 2 which directly contacts the skin of a wearer, a leakproof layer 3 which is provided on the side farther from the body skin and composed of a rectangular liquid-impermeable back-sheet and the like made of polyethylene plastic film or the like, and an absorbent portion for body fluids 1 located between the preceding two components.

In addition, there is provided a flexible outer sheet 4 on the rear side of the product, that is, on the back side of the leakproof layer 3, and this flexible outer sheet 4 comprises a sheet of non-woven fabric or multi-layered non-woven fabric sheets which are air-permeable and water-repellent.

On the both sides of the product, uprising cuffs C and C protruding from the lower part along the use-surface side are formed respectively; these uprising cuffs are composed of an uprising sheet 8 which is practically continuous in the width direction and a piece or a plurality of pieces of elastic member 9 made of, for example, rubber thread. In more detail, the uprising cuff C is made of double-layered uprising sheet 8 and formed in a fixed state, wrapping up the elastic member 9, by using a hot melt adhesive or the like. It is preferable that the uprising sheet 8 constituting each uprising cuff C is not liquid-permeable but liquid-impermeable or hydrophobic. It may also be acceptable that a property of a liquid-permeable sheet such as non-woven fabric is converted to liquid-impervious property by treating with silicone. Further, it is preferable for the uprising sheet 8 to be provided with permeability to air or moisture. It is possible to enhance leakproof property further by inserting a liquid-impermeable film sheet between the uprising sheets 8.

The inner surface of the double uprising sheets 8 is fixed to the surface sheet 2 and the outer sheet 4 by using a hot melt adhesive or the like. As the result, the fixation beginning of the double uprising sheets 8 forms the uprising edge of the uprising cuffs C. The leading side farther than this uprising edge is a free portion which is not fixed to the main body of the product.

On the other hand, the longitudinal front and back ends of the double uprising sheets 8 are fixed to the article, more specifically to the outer surface of the surface sheet 2, by using a hot melt adhesive or the like in a state that the end of the free portion is directed to the central side of the article. The space surrounded by the right and left uprising cuffs, C and C, forms a space for containment of urine or loose stool. When urinated into this space, the urine is absorbed in the absorbent portion for body fluids 1 through the liquid-permeable surface sheet 2, and the uprising cuffs C serve as a barrier, thus preventing the solid content of the loose stool from overrunning.

On the other hand, the longitudinal end portions of the front body and back body are provided, between the non-woven fabrics of the outer sheet 4 at the waist part, with elastic members for waist, 10 and 10, which are composed of fine rubber threads spaced in parallel at the edge of the waist opening part for the sake of enhancing fitness to the waist and fixed with a hot melt adhesive or the like in an expanded state so as to allow them to expand and contract. The space and pieces for the elastic members, 10 and 10, are determined appropriately, and for example, the space is preferably from 4 to 8 mm and the pieces are preferably from 3 to 10. The numeral 11 represents a tape fastener for connecting the right and left back side edges to each other by bringing them over to the right and left abdominal front sides.

1.2 Basic Construction of the Present Invention

In the present invention, an absorbent member which contracts on contacting body fluids is provided at a predetermined part to absorb and retain body fluids, for example, the absorbent portion for body fluids 1 shown in FIG. 2, so as to be able to contract. The details of such an absorbent member will be described later.

1.3 Basic Function

In the diaper thus constructed, when a body fluid such as urine is excreted into a zone Z as shown in FIG. 3, an absorbent member 25 which contacts the body fluid contracts. As the result, the portion of the absorbent member 25 which has absorbed the body fluid moves from the position where the body fluid was excreted and in turn, a new portion of the absorbent member 25 moves in the position. In other words, the absorbent portion of the absorbent member 25 is renewed and displaced from the portion where the body fluid is excreted in accordance with the excretion of the body fluid. Therefore, the whole part of the absorbent member 25 is utilized efficiently, and as a whole, the absorption volume is strikingly improved, while the absorbent member 25 may be thin. Accordingly, a diaper to which the present invention is applied can be endured for a long time wearing.

2 Example of Absorbent Member 2.1 "Absorbent members which contracts on contacting body fluids" of the present invention will hereinafter described in detail referring to specific examples. Specific examples of the absorbent members are classified broadly into "those comprising an contraction material having a specified length which contracts on contacting body fluids and an absorbent material for body fluids united practically with the contraction material" and "absorbent members comprising a single material that possesses a function of contraction by contacting with body fluids together with a function of absorption and retention of body fluids". Further, the former is classified broadly into "an absorbent material for body fluids comprising "a highly absorbent polymer and a carrier for its retention"" and "an absorbent material for body fluids comprising a highly absorbent material alone".

Figure 4:
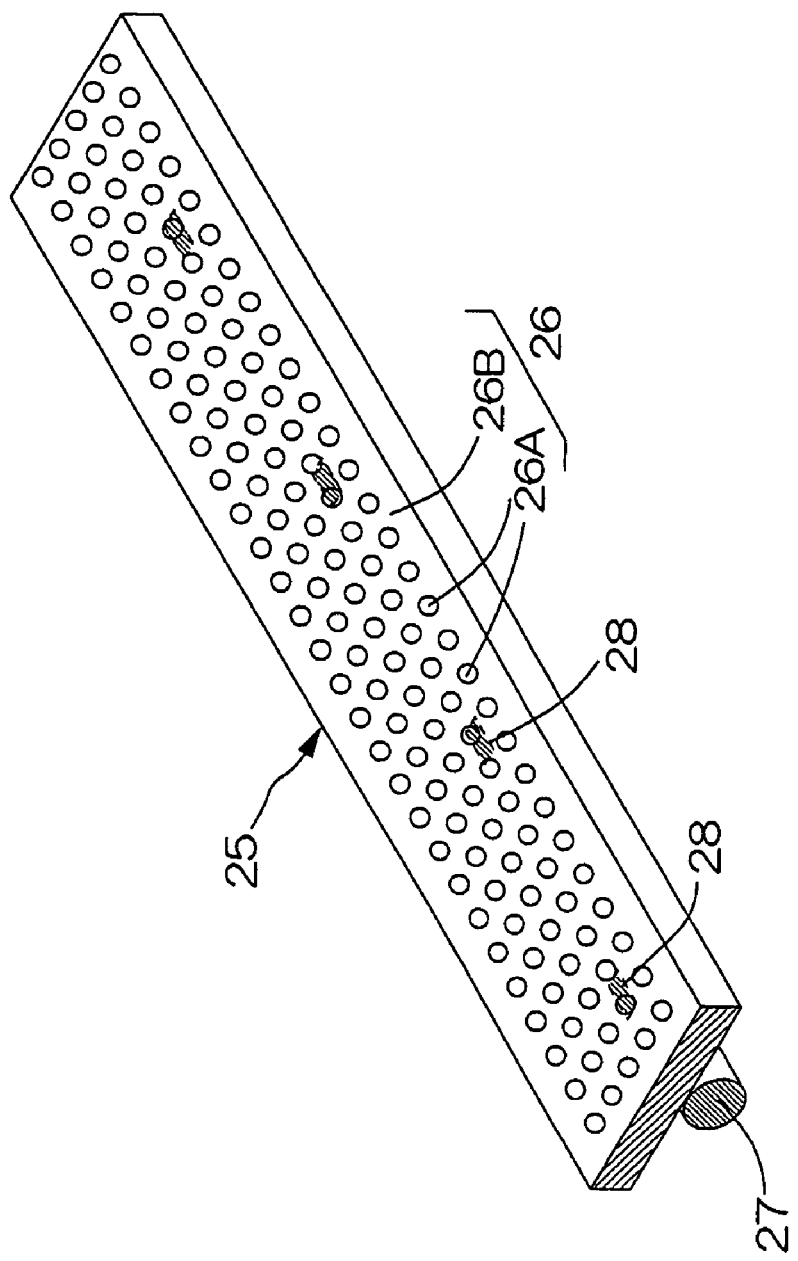
FIG. 4 is a perspective view of an example of an absorbent member.

2.1.1 Absorbent member comprising a contraction material and an absorbent material for body fluids 2.1.1.1 Absorbent material for body fluids comprising a highly absorbent polymer and a carrier for its retention FIG. 4 illustrates an example of the absorbent member 25 comprising a contraction material 27 and an absorbent material for body fluids 26. In this absorbent member 25, the absorbent material for body fluids 26 consisting of a highly water-absorbent polymer 26A and a carrier 26B for retention of the highly water-absorbent polymer 26A and the contraction material 27 are practically united.

In more detail, the carrier 26B is in a ribbon shape and made of non-woven fabric and the like. In the absorbent member 25 of this example, the highly water-absorbent polymer 26A is attached to or retained by bonding or the like on the carrier 26B. The highly water-absorbent polymer 26A may be arranged on the carrier either serially in the direction of contraction as illustrated or intermittently as described later (ditto for other examples). The absorbent material for body fluids 26 can be obtained, for example, by fixing the highly water-absorbent polymer 26A on a material sheet of the carrier 26A, followed by cutting in a predetermined width and length.

Figure 5:
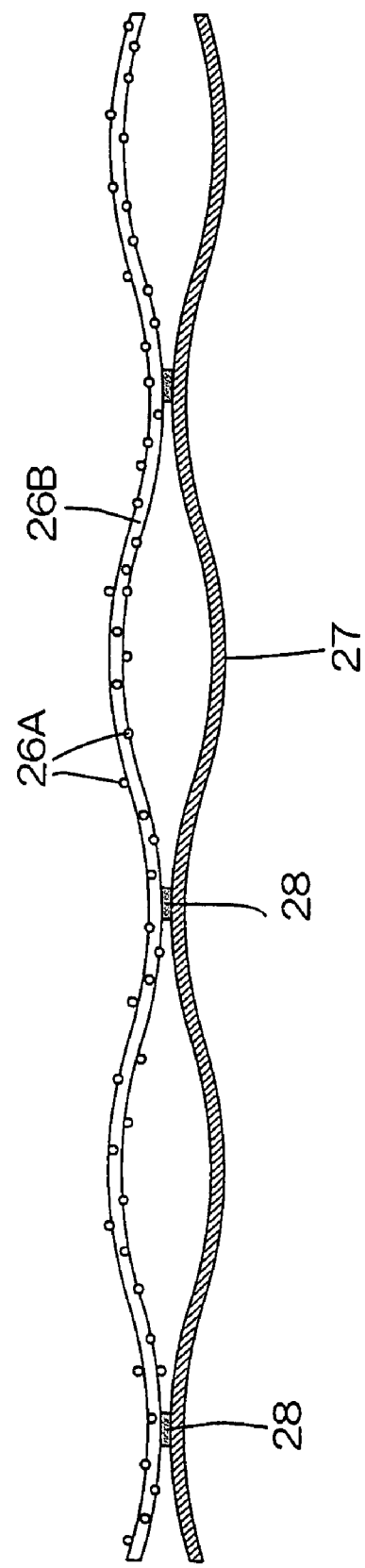
FIG. 5 is a front view of an example of another absorbent member.

Further in the present invention, as shown in FIG. 5, the thread-like carrier 26B on which the highly water-absorbent polymer 26A is attached and the contraction material 27 are united by bonding or the like, thus providing another form to be adopted.

Furthermore in the present invention, for the purpose of using a large amount of a highly absorbent polymer or preventing it from falling off from the carrier, a sealed pouch-like carrier in which the highly absorbent polymer is contained can be used. This can be obtained by forming a pouch as well as enclosing and retaining a highly water-absorbent polymer therein, followed by cutting in a predetermined width and length and forming, for example, a ribbon shape as a whole. In this way, it is possible to prevent the polymer from falling off and retain a larger amount of the polymer in one place. Particularly as described later, when the inner space of the pouch-like carrier is divided to have a plurality of compartments and a highly water-absorbent polymer is retained in all or appropriate parts of these compartments, it is possible to prevent uneven distribution of the polymer within the pouch-like carrier. Since a construction where this pouch-like carrier is applied will be described later, more explanation on this matter is omitted here.

Thus, the carrier 26B of the present invention may be in a filamentous form or made of spun yarn. Further, the carrier 26B may be made by slitting a sheet composed of staple fiber or continuous fiber in a ribbon-like or tape-like shape or may be made in a pouch-like shape. In addition, the carrier 26B may have a multi-layered pouch-like structure or a matrix structure. In this case, the highly water-absorbent polymer 26A may be fixed among the multilayer of the carrier 26B or on the surface thereof or in the matrix structure or the surface thereof.

2.1.1.1.1 Example of method for retaining a highly absorbent polymer on the carrier In case where the highly absorbent polymer 26A in a particulate or fibrous form is used, the highly absorbent polymer 26A can be retained on the carrier 26B by attaching or bonding. To be more specific, a well-known art for fixing highly water-absorbent polymers, for example, attachment by adding a slight amount of water to the highly absorbent polymer 26A, adhesion by using an adhesive and the like can be employed. As long as the adhesive is adherent in performance, it is advantageous for processing, but not particularly limited. The bonding of the highly absorbent polymer 26A to the carrier 26B should be maintained for at least a few minutes after being swelled by water, and a longer maintenance time may be permitted.

In addition, using fiber aggregates such as non-woven fabrics (examples to be described later) as a carrier also allows a highly absorbent polymer to be retained among the fibers or interposed between the fiber aggregates to be laminated. Thus, a composition used widely for the absorbent body in the field of this kind of absorbent articles for body fluids can be employed for the absorbent material for body fluids of the present invention.

On the other hand, the highly absorbent polymer in a thread-like form can be retained on the carrier 26B by mechanical intertwining such as suture, knitting and weaving in addition to attaching and bonding as described before.

In case where a pouch-like carrier is used, the highly absorbent polymer may be movably contained therein. It should be noted that the highly absorbent polymer may be unevenly distributed within the carrier when the contained amount of the highly absorbent polymer is relatively small in the pouch-like carrier. In such a case, the highly absorbent polymer may be either attached or bonded to the inner surface of the pouch-like carrier. The attaching or bonding may be carried out by the well-known art for fixing highly absorbent polymers, for example, bonding by using an adhesive and the like besides attachment by adding a slight amount of water.

2.1.1.1.2 Material for the Carrier

The material for the carrier may be selected appropriately, and basically it may be either permeable to body fluids, for example, non-woven fabric, porous film and the like, or impermeable to body fluids, for example, synthetic resin-made sheet and the like; however it is preferable to use the former. In particular, liquid-permeable hydrophilic non-woven fabric containing thermoplastic synthetic fibers and having a basis weight of approximately from 15 to 20 g/m$^2$ (well-known spun bonded non-woven fabric, carded web-bonded non-woven fabric, meltblown non-woven fabric, non-woven fabric combined them and the like) or tissue paper containing synthetic pulp (e.g. SWP manufactured by Mitsui Petroleum Co. Ltd.) and having a basis weight of approximately from 15 to 20 g/m$^2$ may preferably be used. In particular, the material is preferably provided with a water-holding capacity so as to efficiently wet the contraction material 27 arranged side by side.

Particularly when the pouch-like carrier is used, at least a part of the pouch-like carrier is made permeable to body fluids. In order to fulfill the absorptive function (e.g. a balance of absorption rate and diffusion) comparable to that of conventional absorbent articles, at least the body-facing side of the pouch-like carrier (the side facing to the excretory part of body fluids; ditto hereinafter) is made permeable to body fluids. In this case, the whole of the pouch-like carrier may be made of a sheet permeable to body fluids, or a part or the whole of the body fluid-accepting side of the pouch-like carrier may be made of a sheet permeable to body fluids and a part or the whole of the opposite side may be made of a sheet impermeable to body fluids or a sheet hardly permeable to body fluids. On the other hand, when the diffusion is considered more seriously than the absorption rate, the body-facing side of the pouch-like carrier may be made impermeable—or hardly permeable—to body fluids, and the lateral side and rear side (the opposite side of the body-facing side) may be made permeable to body fluids.

Figure 6:
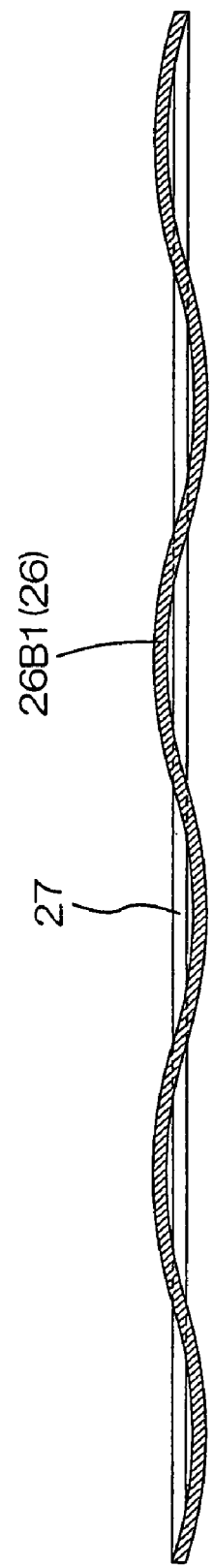
FIG. 6 is a front view of an example of another absorbent member.

2.1.1.2 Absorbent material for body fluids comprising a highly absorbent material alone As shown in FIG. 6, an absorbent material for body fluids 26 comprising a highly absorbent material alone may also be used and in this case, advantages offered are that the aforementioned carrier 26B becomes unnecessary and that there are no worries about falling off of the polymer 26A from the carrier 26B and the like. The absorbent material for body fluids 26 for use in this construction is preferably in a thread-like form as illustrated. When the contraction material 27 for use in combination with this absorbent material for body fluids is also in a thread-like form, the absorbent material for body fluids 26 and the contraction material 27 may be intertwined with each other to be united as illustrated. And in this case, the absorbent material for body fluids 26 and the contraction material 27 may also be united by suture, knitting, weaving or the like. In addition, there is another preferable construction in which the absorbent material for body fluids 26 and the contraction material 27 may be united by lining up to be bundled without intertwining with each other.

The absorbent material for body fluids 26 in such a thread-like or string-like form has a small contact area against the surrounding contact surface, and therefore, has a small contact resistance. Accordingly, the renewal function of the present invention may be fulfilled, even if the contraction force of the contraction material 27 is weak. This effect is particularly remarkable in the construction in which the absorbent material for body fluids 26 and the contraction material 27 are united by lining up to be bundled without intertwining with each other. In other words, the amount, size or performance of the contraction material 27 required for fulfilling the same level of the renewal function may be reduced, thus lowering the cost of the contraction material 27. The use of the absorbent material for body fluids 26 in a thread-like or string-like form may decrease a void space compared with the collective use of the particulate, highly absorbent polymer which has conventionally been used in the field of absorbent articles, and therefore, the same absorption capacity may be achieved by a smaller volume and making a thinner absorbent member 25 may be achieved. Further, the absorbent material for body fluids 26 in such a thread-like or string-like form is preferable because unification with the contraction material 27 can be carried out with ease and reliability.

In another example not illustrated, the highly water-absorbent polymer 26A is directly bonded only to the contraction material 27 without using the carrier 26B, which can be used as the absorbent member 25. Thus, in this latter case, the highly water-absorbent polymer 26A itself functions as the absorbent material for body fluids 26. In this case, the highly water-absorbent polymer 26A may also be bonded to both the carrier 26B and the contraction material 27.

2.1.1.3 Specific Example of the Highly Absorbent Polymer

The highly water-absorbent polymer for use in this kind of disposable absorbent articles and capable of absorbing and retaining body fluids more than 20 times its own weight can be used. As examples for this, there are starch type, cellulose type and synthetic polymer type, including starch-acrylate (salt) graft copolymer, saponified starch-acrylonitrile copolymer, crosslinked sodium carboxymethyl cellulose and acrylate (salt) polymer.

Preferable absorption characteristic of the highly water-absorbent polymer is that it absorbs and swells more than 10 times its volume within 10 seconds.

The form of the highly absorbent polymer to be used may be a pulverized particulate form which is currently common, and instead of this or in combination with this, a fibrous form may also be used. The highly absorbent polymer in a fibrous form may be used in a thread-like or string-like form by spinning or the like. The aforementioned example shown in FIG. 6 is an example where the thread-like or string-like highly absorbent polymer is employed.

As a highly absorbent polymer in such a fibrous form, besides the highly absorbent polymer disclosed in Japanese Patent Publication No. 2656245, that prepared by carboxymethylating rayon filament or rayon spun yarn, followed by treatment with an appropriate crosslinker such as epoxy type to limit the solubility (practically non-contractible upon contacting body fluids) can be utilized. Instead of the rayon, cellulose-type fibers such as cotton and cuprammonium rayon may be utilized in the above instance. Further, an absorbent fiber made by hydrolyzing acrylic fiber may also be utilized. In addition, the material disclosed in Kokai (Jpn. unexamined patent publication) No. 11-200209 may be utilized as well. A commercially available material, Lanseal (manufactured by Toyobo Co. Ltd.), may be listed.

When the highly absorbent polymer 26A is bonded to the carrier 26B by an adhesive, the highly absorbent polymer is preferably altered so that its surface may partially be compatible with the adhesive with ease.

2.1.1.4 Supply Amount of the Highly Absorbent Polymer

The amount of the highly water-absorbent polymer 26A supplied to the carrier 26B is determined according to setting of the absorption volume by said absorbent article, and it is desirable to change the shape of the carrier 26B depending on light use or heavy use. The examples shown in FIGS. 3 to 5 are suitable for light use, while an example suitable for heavy use may make use of a form in which the highly water-absorbent polymer 26A is contained in the aforementioned pouch-like carrier.

It should be mentioned that, when the pouch-like carrier is used, a large amount of a highly absorbent polymer may be packed within the carrier, while there is a fear that local gel blocking may occur due to tight contact of the highly absorbent polymers mutually at the site of swelling which is caused by absorption of body fluids. Once this occurs, the flow expansion of body fluids to the highly absorbent polymer at other places is prevented, which gives rise to a reduction in the absorption rate. Therefore, in order to prevent this, an interstitial volume after swelling of the highly absorbent polymer is preferably reserved within the pouch-like carrier beforehand by adjusting the amount of the highly absorbent polymer to 0.01 to 0.1 g per 5 to 20 $cm^2$ of the space area of the pouch-like carrier in a state that it is crushed flat, thereby allowing to form a space within the pouch-like carrier.

2.1.1.5 Specific Example of the Contraction Material

The contraction material 27 contracts upon contacting body fluids and may be produced by the art disclosed in Kokoku (Jpn. examined patent publication) No. 6-102068 and Japanese Patent Publication No. 2656245. As a commercially available product, "Solvron" manufactured by Nitivy Co. Ltd. may be used and its thickness is preferably from 500 to 1600 dtex. As the contraction material 27, materials in any form, for example, thread-like with circular or square cross section, sheet-like, film-like, and net-like forms and the like may be usable. The contraction material 27 may also be in a filament form or spun yarn.

2.1.1.6 Example of method for uniting the contraction material and the absorbent material for body fluids The contraction material 27 and the absorbent material for body fluids 26 can be practically united in a form fixed longitudinally and intermittently by the adhesive 28 or in a form intertwined mechanically as mentioned above.

As the procedures, the absorbent material for body fluids 26 is obtained by retaining the highly water-absorbent polymer 26A on the carrier 26B, followed by uniting this with the contraction material 27. Alternatively, the carrier 26B and the contraction material 27 are united together, and then the highly water-absorbent polymer 26A can be retained on the carrier 26B. In particular, when the pouch-like carrier is used, it is possible that the carrier-forming sheet and the contraction material are united, and then the highly absorbent polymer is arranged on the sheet to make this pouch-like.

It should be noted that one absorbent material for body fluids 26 may be provided with a plurality of the contraction materials 27, for example, in the width direction side by side with certain space. Further, a plurality of the contraction materials 27 which are bonded to each other in the longitudinal direction with certain space are fixed to the absorbent material for body fluids 26. In addition, a plurality of the pieces of the absorbent material for body fluids 26 may be used in twisting in order to adjust the degree of contraction.

2.1.2 Absorbent member comprising a single material that possesses the function of contraction by contacting with body fluids together with the function of absorption and retention of the body fluids In a particularly preferable embodiment, the absorbent member which has a capacity of absorbing body fluids more than 10 times its own weight and comprises solely a thread-like or string-like material composed of a fibrous, highly absorbent polymer contracting upon absorbing body fluids may be used. The thickness of the absorbent member may be selected appropriately and is preferably at most 5 mm. Such a fibrous, highly absorbent polymer is based on "a fiber which comprises denatured polyvinyl alcohol containing carboxyl groups from 0.5 to 10% by mole and contracts in the presence of water" disclosed in Japanese Patent Publication No. 2656245, and can be obtained by enhancing the absorbency with increased number of polar group introduction or by adjusting crosslinking degree to control the solubility. It should be noted that this embodiment is not illustrated but the appearance is almost the same as that of the illustrated embodiment from which the absorbent material for body fluids 26 is omitted.

In this case, the thread-like or string-like material composed of a fibrous, highly absorbent polymer contracting upon absorbing body fluids serves both as the contraction material 27 and the absorbent material for body fluids 26 in the aforementioned embodiment, and therefore, there are several advantages that the number of materials may be decreased, the production may be simplified, a thinner absorbent member 25 may be attempted and so on. Particularly, since the absorbent member 25 is thread-like or string-like, its volume is made small compared with that of the collective use of the particulate highly absorbent polymer, allowing to make the absorbent member 25 much thinner. In general, a higher absorbent polymer having a higher absorbent capacity tends to lower its contraction force. However, the absorbent member 25 in a thread-like or string-like form has a small contact area against the surrounding contact surface, and therefore, the contact resistance becomes smaller. Accordingly, the renewal function of the present invention may be fulfilled by enhancing the absorbent capacity of the absorbent member 25, even if its contraction force becomes lower.

2.2 Examples of Other Preferable Absorbent Members

Next, examples of other preferable absorbent members are explained. In all of these embodiments, the absorbent material for body fluids comprises the highly absorbent polymer and the carrier.

Figure 7:
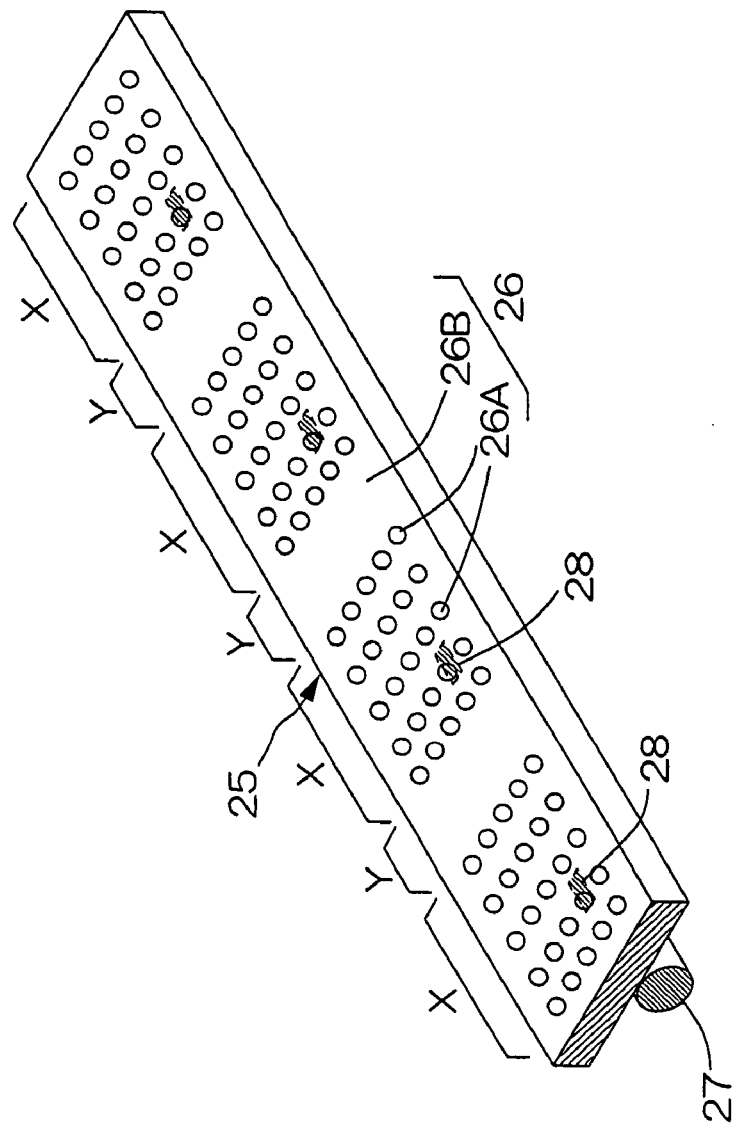
FIG. 7 is a perspective view of an example of another absorbent member.

2.2.1 Construction where the highly absorbent polymer is arranged intermittently in the direction of contraction In the present invention, when the absorbent material for body fluids comprises the highly absorbent polymer and the carrier, it is preferable that the highly absorbent polymer 26A is arranged intermittently on the carrier 26B intermittently in the direction of contraction as shown in FIG. 7. In this case, the part X having the highly absorbent polymer 26A and the part Y not having the highly absorbent polymer 26A are repeatedly arranged by turns in the direction of contraction of the carrier 26B. The example shown in FIG. 7 employs the intermittent arrangement of the highly absorbent polymer 26A in the example shown in the aforementioned FIG. 4. And the embodiment shown in FIG. 8 employs the intermittent arrangement of the highly absorbent polymer 26A in the example shown in the aforementioned FIG. 5. As evidenced by these examples, the intermittent arrangement of the highly absorbent polymer 26A may be employed in either embodiment described above.

Figure 9:
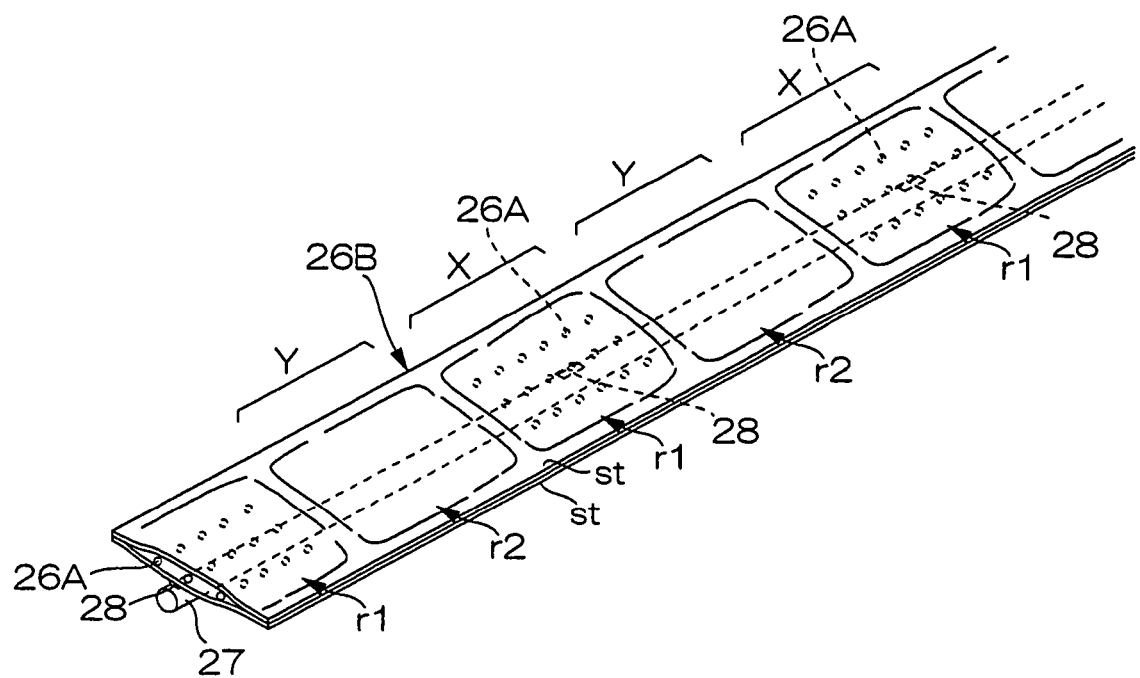
FIG. 9 is a perspective view of an example of another absorbent member.
Figure 10:
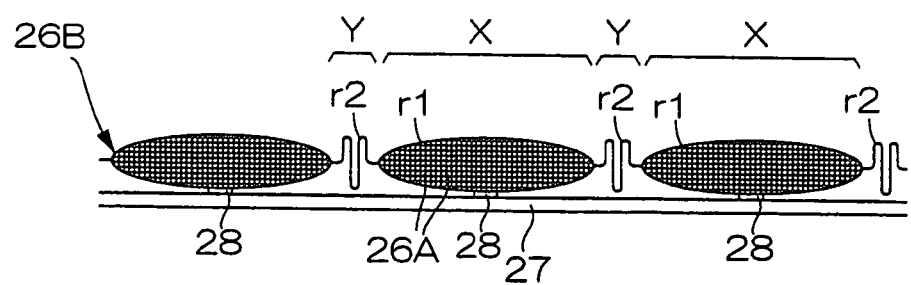
FIG. 10 is a perspective view of the example shown in FIG. 9 in a contracted state.

On the other hand, in the construction where the highly absorbent polymer 26A is arranged on the outer surface of the carrier 26B, a limitation in the supply amount of the highly absorbent polymer 26A can not be avoided as a whole considering the retention capacity of the highly absorbent polymer 26A, and the limitation causes the absorbent capacity to become lower, rendering it unsuitable for heavy use. To solve this problem, an example in which the pouch-like carrier is utilized in order to increase the usable amount of polymer as mentioned above and in which the highly absorbent polymer is contained intermittently in the direction of contraction within the pouch-like carrier extending to the direction of contraction as shown in FIG. 9 and FIG. 10 is also proposed. In this embodiment, with the aim of arranging the polymer intermittently, the pouch-like carrier 26B is formed so as to be provided therein with many compartments, r1, r2 . . . , in the direction of contraction, and every two compartments of r1, r2 . . . are filled with the highly absorbent polymer 26A (every three or more compartments may be filled with the polymer), and the filled compartment r1 filled with the highly absorbent polymer 26A and the unfilled compartment r2 not filled with the highly absorbent polymer 26A are formed alternately in the direction of contraction.

As a method for forming such compartments of the pouch-like carrier 26B, for example, a method in which a pair of liquid-permeable sheets, st and st, are overlaid and predetermined parts such as the rim of the pouch-like carrier and the periphery of the compartment are bonded with a hot melt adhesive, ultrasonic adhesion, or bonding with heat seal is recommended. The materials for the pouch-like carrier are those described above. In addition, this sheet is united with the contraction material 27, and when the contraction material 27 contracts, a force of approximately from 2 to 5 N is applied to the portion bonded to the contraction material 27, and therefore, it is preferable that the sheet possesses enough wet strength to endure the force.

Further, being different from the illustrated embodiment, the highly absorbent polymer may be intermittently arranged by a fixation means such as attachment or adhesion against the unified inner space of the pouch-like carrier without providing any partition.

Thus, when the highly absorbent polymer 26A is arranged on the carrier 26B intermittently in the direction of contraction and when the highly absorbent polymer 26A absorbs body fluids and swells, the contraction of the absorbent material for body fluids 26 at the expansion portion X shown in FIG. 10 is blocked due to its expansive force, while the portion Y where the highly absorbent polymer 26A is not arranged is free from such blocking and can readily contract, resulting in that the absorbent member 25 as a whole can contract efficiently. For this reason, the absorbent member 25 as a whole can contract sufficiently, even if a large amount of the polymer is arranged at one place.

Particularly when the carrier 26B is made pouch-like and the highly absorbent polymer 26A is arranged intermittently in its inside, there are advantages that the intermittent arrangement of the highly absorbent polymer 26A can be maintained more securely as well as the absorbent capacity may be ensured sufficiently, since the highly absorbent polymer 26A is free from falling from the carrier and a larger amount of the highly absorbent polymer 26A may be retained in one place. Thus, in the embodiment where the highly absorbent polymer 26A is arranged intermittently in the inside of the pouch-like carrier 26B, the highly absorbent polymer 26A is retained securely within the carrier 26B, and therefore, when applied to the absorbent article for body fluids, said carrier 26B may be exposed to the body side and the surface sheet 2 in specific reference to the embodiment shown in the aforementioned FIG. 2 may be omitted.

When the highly absorbent polymer is arranged intermittently and when the length of contraction direction of the portion Y where the highly absorbent polymer 26A is not arranged is longer than that of the polymer-arranged portion X, the efficiency of contraction is improved, whereas the absorbent capacity is reduced due to the reduction in area of the polymer arrangement. In contrast, when the length of contraction direction of the portion Y where the highly absorbent polymer 26A is not arranged is shorter than that of the polymer-arranged portion X, the absorbent capacity is improved, whereas the efficiency of contraction is decreased. Accordingly, in the carrier 26B, the length of contraction direction of the portion Y where the highly absorbent polymer 26A is not arranged (corresponding to the unfilled compartment part r2 in the pouch-like carrier shown in FIG. 9) is designed to be desirably from 30 to 400%, more particularly from 80 to 300%, of the length of contraction direction of the portion X where the highly absorbent polymer 26A is arranged (corresponding to the filled compartment part r1 in the pouch-like carrier shown in FIG. 9). In this way, both the efficiency of contraction and the absorption capacity become excellent.

Figure 8:
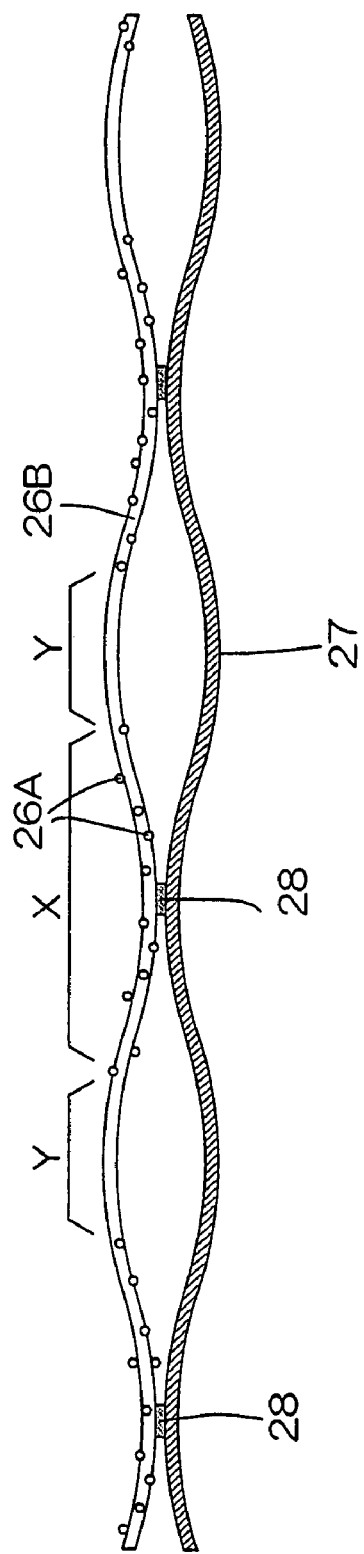
FIG. 8 is a front view of an example of another absorbent member.

As described above, the contraction material 27 and the absorbent material for body fluids 26 are practically united by such as intermittent fixation in the longitudinal direction using the adhesive 28 or the like. However, the fixing part 28 of the contraction material 27 fixed to the carrier 26B of the absorbent material for body fluids 26 hardly contracts and also the polymer-arranged portion X in the carrier 26B hardly contracts as mentioned above. Therefore, the fixing part 28 and the polymer-arranged portion X are matched in the contraction direction as shown in FIGS. 7 to 9, and in other parts, the contraction material 27 and the carrier 26B are desirably left unfixed to each other. In this way, both of the contraction material 27 and the absorbent material for body fluids 26 may contract effectively. In contrast, when the fixing part 28 of the contraction material 27 is matched to the portion Y where the highly absorbent polymer is not arranged or when the contraction direction of the contraction material 27 is totally fixed to the carrier 26B, the contraction of one member is restricted by the fixation to the other member, thereby making it hard to contract and lowering the efficiency of contraction.

2.2.2 Construction with Expandable Pouch Body

As described above, when the pouch-like carrier is used, a larger amount of the highly absorbent polymer may be advantageously retained in one place, whereas when body fluids are supplied, the part of the highly absorbent polymer having swelled earlier in said retaining place may tend to block the supply of body fluids to the rest of the unswelled polymer. To prevent this, a larger size of the pouch-like carrier may be formed with consideration given to the swelling volume of the highly absorbent polymer. However, the highly absorbent polymer increases its volume up to about 50-fold at the maximum after absorbing body fluids and when this is considered, the width of the pouch-like carrier becomes too large, rendering it difficult to contain the highly absorbent polymer within an objective setting space of the article.

For this reason, a proposed embodiment preferably makes use of the pouch-like carrier formed to be expandable according to the swelling of the highly absorbent polymer inside. This makes the setting space initially required for the pouch-like carrier small as well as makes it hard for local gel blocking to occur because the pouch-like carrier expands concurrently with the swelling of the highly absorbent polymer. Several examples of this expansion means will hereinafter be explained specifically.

2.2.2.1 First Expandable Means

As a first expandable means, a recommended construction is that the pouch-like carrier containing the highly absorbent polymer is arranged in the absorbent portion for body fluids in a state folded back in the width direction orthogonal to the direction of contraction so that the folded-back portion may open to be restored to the original state and expand by swelling of the highly absorbent polymer retained inside. The number of the folds is not particularly limited, but preferably two and three at most, and the width in the folded state is preferably less than half of that in the unfolded state.

Figure 11:
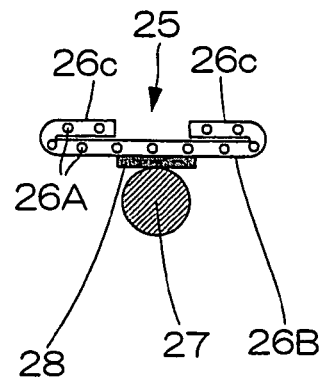
FIG. 11 is a cross sectional view of an example of another absorbent member.
Figure 12:
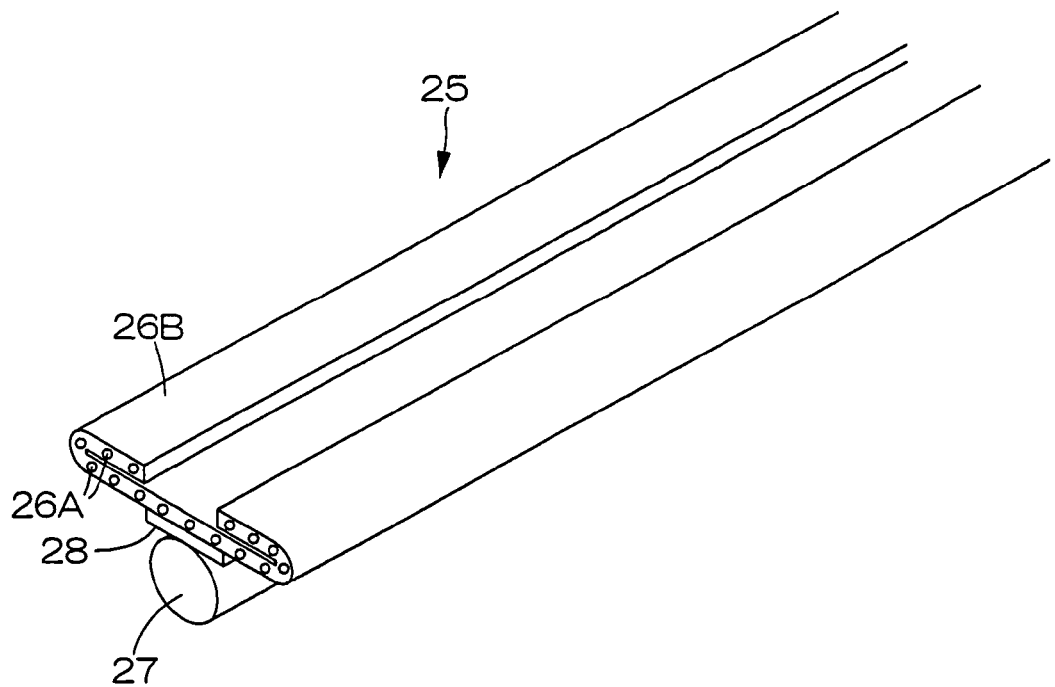
FIG. 12 is a perspective view of the example shown in FIG. 11.
Figure 13:
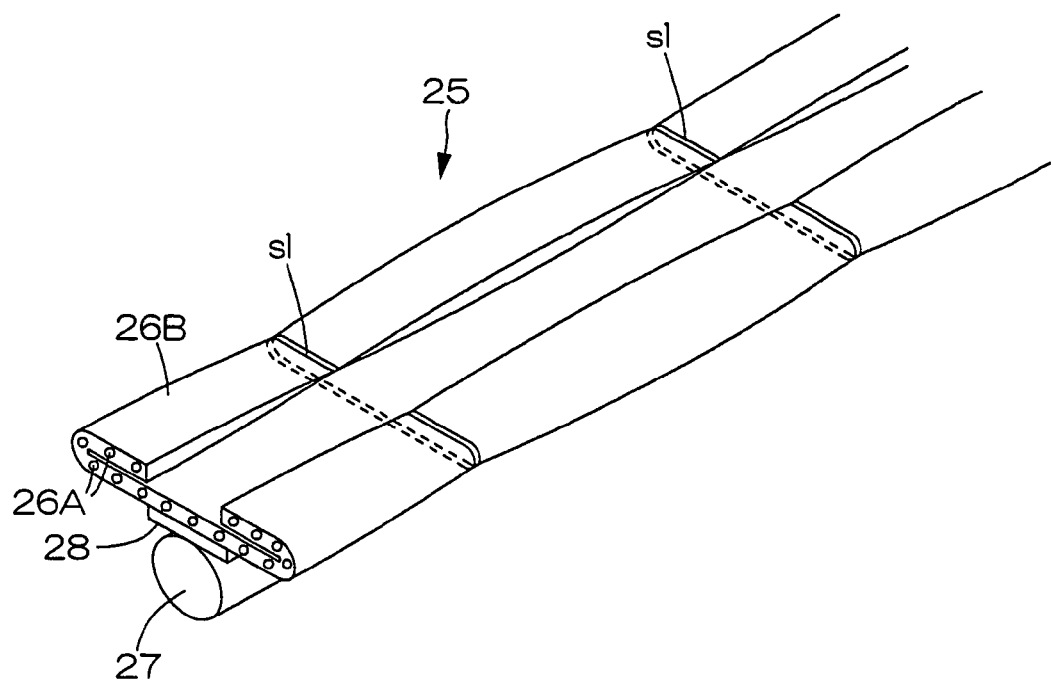
FIG. 13 is a perspective view of an example of another absorbent member.
Figure 14:
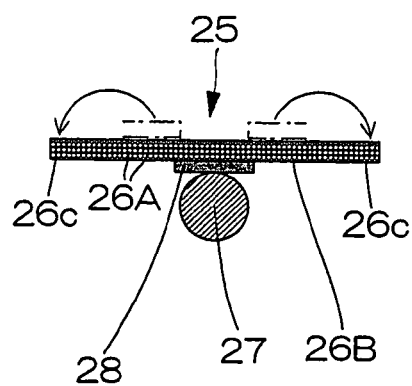
FIG. 14 is a cross sectional view showing a state at the time of absorbing body fluids in the examples shown in FIGS. 11 to 13.

FIG. 11 illustrates this preferable construction where the pouch-like carrier 26B containing the highly absorbent polymer 26A is arranged in the article (for example, in the absorbent portion for body fluids 1 in the aforementioned example shown in FIG. 2) in a state that both lateral end portions, 26C and 26C, are folded back toward the center of the width direction. As shown in FIG. 12, the carrier is in a form capable of being opened up at both sides when sealing is not conducted to make the aforementioned compartments, r1, r2 . . . On the other hand, when sealing is conducted to make the aforementioned compartments, r1, r2 . . . , the carrier is made to a form capable of being opened up on both sides by applying the seal, s1, s1 . . . , prior to its folding as shown in FIG. 13 (not limited to this). Thus, when the polymer 26A absorbs body fluids and swells, the pouch-like carrier 26B is restored to the original state by being opened up at the folded-back portions, 26c and 26c and new absorbent surface is exposed, as shown in FIG. 14. In other words, the folded-back portions which have absorbed body fluids open to both sides, and the underlying portions which have not absorbed yet are exposed, and therefore the polymer having swelled earlier does not block the supply of body fluids to the rest of the unswelled polymer. Further, it goes without saying that the arrangement space required initially for the pouch-like carrier becomes smaller.

Figure 15:
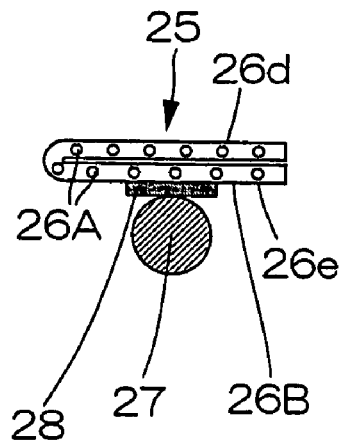
FIG. 15 is a cross sectional view of an example of another absorbent member.

A similar kind of the example includes a form in which one lateral end is folded to the other end at the center of the width direction as shown in FIG. 15.

2.2.2.2 Second Expandable Means

Figure 16:
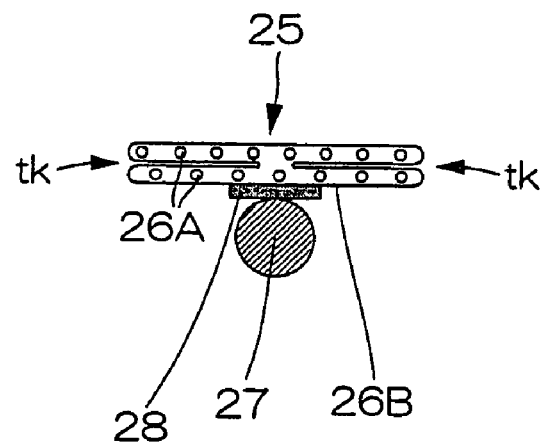
FIG. 16 is a cross sectional view of an example of another absorbent member.
Figure 17:
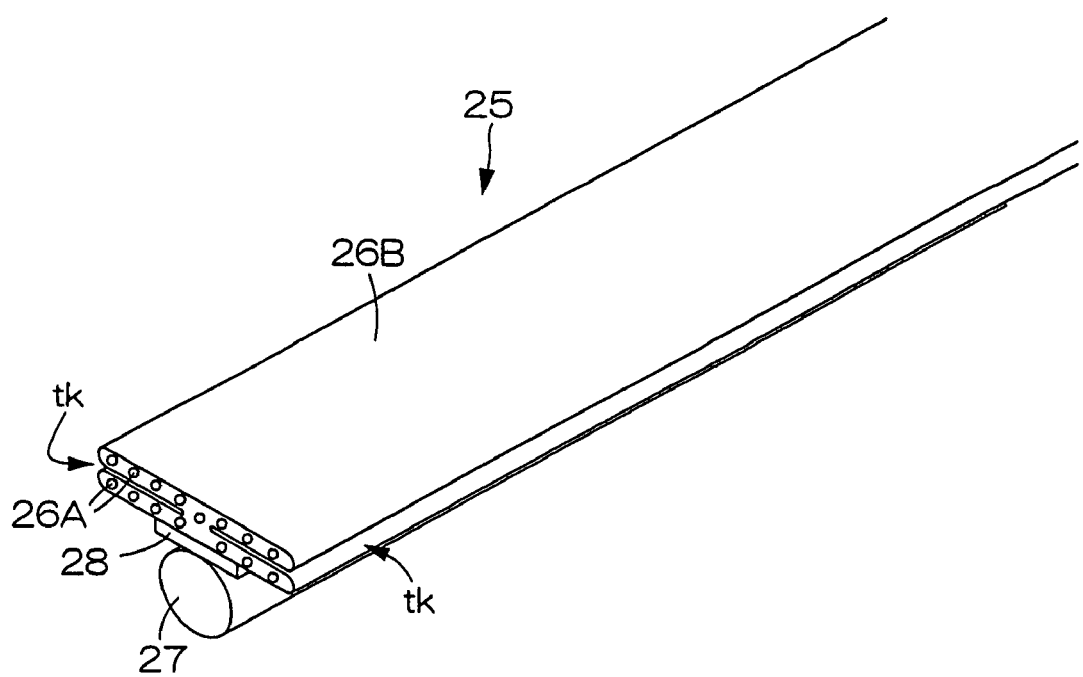
FIG. 17 is a perspective view of the example shown in FIG. 16.

As a second expandable means, it is recommended that the pouch-like carrier 26B is provided with tucks, tk and tk, as shown in FIG. 16 and FIG. 17. In the illustrated example, tucks, tk and tk, are formed on both sides of the pouch-like carrier 26B with folding lines along the direction of expansion-contraction. When such tucks, tk and tk, are formed, the pouch-like carrier 26B becomes advantageously expandable to the direction of thickness. In the present invention, the tuck tk may be formed on one side or all over, or the tuck tk may also be formed along the width direction or the diagonal direction. The illustrated example employs one tuck, while the number of the tuck may be increased further to two tucks, three tucks and so on.

Figure 18:
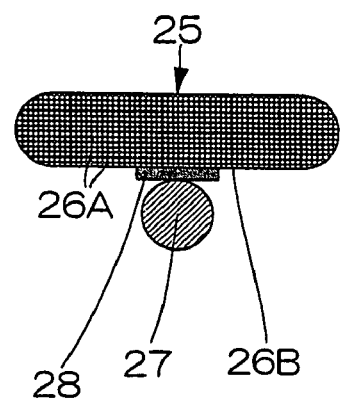
FIG. 18 is a cross sectional view showing a state at the time of absorbing body fluids in the examples shown in FIGS. 16 and 17.

In this way, the tucks, tk and tk, may be stretched to expand by swelling of the highly absorbent polymer 26A contained inside, as shown in FIG. 18.

2.2.2.3 Third Expandable Means

Still another expandable means proposed makes use of a construction capable of expanding dependent on swelling of the highly absorbent polymer 26A by means of shape design such as prior shirring on the pouch-like carrier 26B or material design to make the pouch-like carrier 26B of an elastic material.

2.2.2.4 Fourth Expandable Means

In the embodiment in which the pouch-like carrier 26B is partitioned so as to make many compartments in the direction of contraction as exemplified, for example, in the above FIG. 9 and FIG. 13, a preferable expandable form, although not illustrated, is constructed such that the partition part (corresponds to the seal s1 exemplified in FIG. 13) may be removed when the highly absorbent polymer in the compartment absorbs body fluids and swells. It should be noted that, if the peripheral bonding parts of the pouch-like carrier 26B (including the bonding parts of both longitudinal ends) are removed, the internal, highly absorbent polymer 26A is released and therefore, said peripheral bonding parts must be constructed not to be removed using an adhesive or a bonding means of which bonding force is not lowered by contacting body fluids.

In order to achieve the removal of the partition, the partitions, d, d . . . , is either constructed so as to be removed by contacting body fluids, or constructed so as to be removed not by contacting body fluids only but by the swelling force of the polymer. The former type of partition d may be formed by bonding the inner surfaces of the pouch-like carrier 26B to each other using an adhesive separable on contacting body fluids. The adhesive separable on contacting body fluids to be used includes water dispersion-type hot melt adhesives constituted of polyvinyl alcohol, polyalkylene oxide, or the like as a main composition and water-soluble hot melt adhesives such as starch glue and carboxymethyl cellulose. Herein, the term used in the present invention "bonding" in connection with the term "an adhesive separable on contacting body fluids" includes both bonding fixation and adhesion fixation in a general sense. The latter type of partitions, d, d . . . , may be formed by bonding (including adhesion) the inner surfaces of the pouch-like carrier 26B to each other with a bonding force enough to be separated by the swelling force of the polymer.

Further, the amount of the highly absorbent polymer 26A supplied to the inside of the pouch-like carrier 26B may be determined appropriately depending on the absorption capacity desired. When the amount to be contained is too large, gel blocking may occur, and therefore, it is recommended that the amount ranges approximately from 0.005 to 0.03 g/cm$^2$ of the area of the compartment r in a state that it is crushed flat. In other words, the volume of the pouch body in which gel blocking hardly occurs even if the highly absorbent polymer 26A swells may be ensured beforehand in this way.

In such absorbent member 25, when body fluids, for example, urine contacts the pouch-like carrier 26B through the use-surface side sheet 21 after passing through the surface sheet 2, the body fluids infiltrate into the pouch-like carrier 26B through the part permeable to body fluids as the body fluids diffuse along the pouch-like carrier 26B, and are absorbed by the highly absorbent polymer 26A in the corresponding compartment r. The highly absorbent polymer 26A which has absorbed body fluids swells. At this time, the partition d surrounding said swelling polymer 26A also contacts the body fluids as shown in FIG. 6 (??) and said partition d is removed. This removal may be achieved by the swelling force of the polymer 26A either as the main cause or the supplemental action in certain case. As the result of such removal, said swelling polymer 26 can freely swell beyond the limitation of the compartment r, and gel blocking to be caused by the tight mutual contact between the polymer 26A and 26A is effectively prevented.

Furthermore, since the partition d is not removed before absorbing body fluids, the highly absorbent polymer can not cross over this to migrate, is trapped within the compartment r where the polymer itself is contained, and is retained evenly within the whole pouch-like carrier 26B. Owing to this preventive effect of uneven distribution of the highly absorbent polymer 26A, the tight mutual contact between the polymer 26A and 26A is reduced, and therefore, the preventive effect of gel blocking by the removal of the partition described above is further improved.

2.2.2.5 Application Examples of Expandable Means

In case where the pouch-like carrier 26B restores to the original state by being opened up at the folded-back portions, 26c and 26c depending on the swelling of the polymer 26A as described in the first expandable means, the area occupied by the pouch-like carrier 26B in the absorbent portion for body fluids 1 widens after absorbing body fluids. The widening in association with swelling can not be avoided even in the second expandable means. Accordingly, when a plurality of the pouch-like carriers 26B are arranged, it is desirable to place some spaces in-between for their mutual separation. In this case, however, the number of the pouch-like carrier 26B to be arranged in the absorbent portion for body fluids 1 becomes fewer and a reduction in the absorption capacity can not be avoided.

Figure 19:
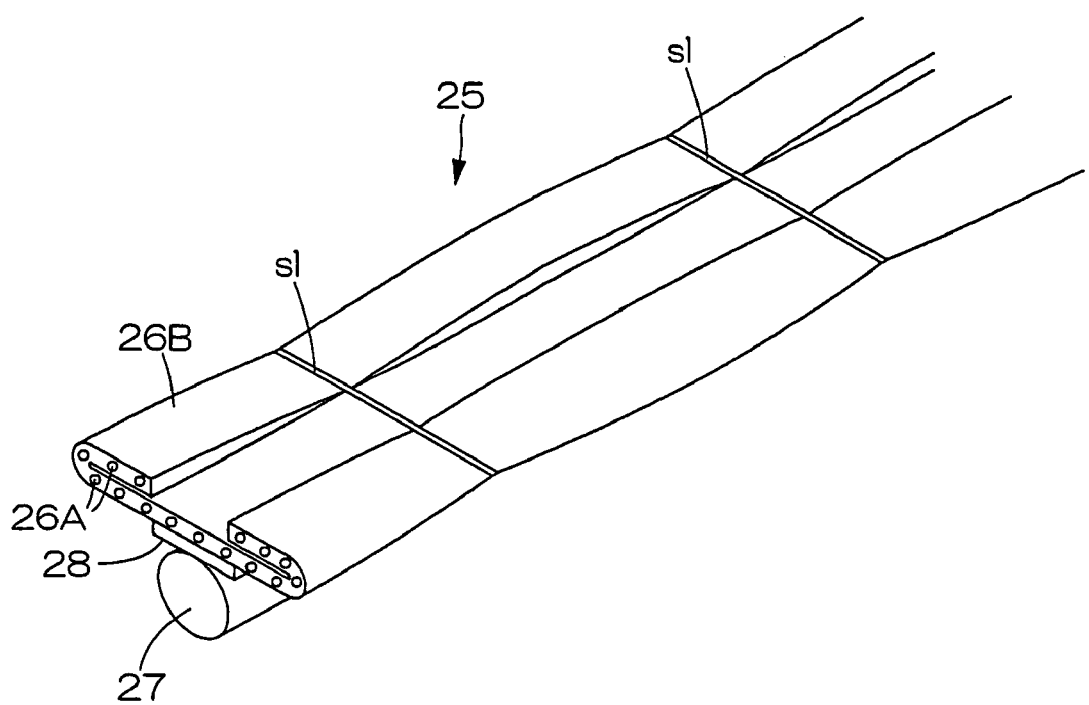
FIG. 19 is a perspective view of an example of another absorbent member.

Consequently, it is preferable that the pouch-like carrier itself or with other member is formed such that the expansion in the width direction may be restrained. Specific means recommended for this in the case of the first expandable means, for example, is offered, as shown in FIG. 19, such that a plurality of the interspaced seal parts, s1, s1 . . . , formed by that the surfaces facing to each other in the direction of thickness of the folded pouch-like carrier 26B are bonded to each other in a continuous line from one end to the other end of the width direction using a bonding means such as heat seal or hot melt adhesion are provided in the contraction direction of the absorbent member 25. These seal parts, s1, s1 . . . , are provided either in common with the aforementioned seals to form the compartments, r1, r2 . . . , or separately.

Figure 20:
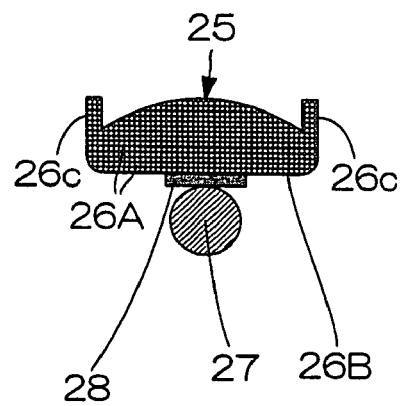
FIG. 20 is a cross sectional view showing a state at the time of absorbing body fluids in the example shown in FIG. 19.

In this way, since the seal parts do not expand to the width direction as shown in FIG. 20, the pouch-like carrier expands mainly to the thickness direction and hardly to the width direction. Accordingly, the polymers having swelled hardly cohere to each other owing to the expansion of the pouch-like carrier 26B, the supply of body fluids to the unswelled polymer is hardly prevented, the aforementioned preventive effect of local gel blocking is exerted as well as the pouch-like carrier 26B may be arranged with a narrower spacing and in a larger number and the absorbent capacity can be enhanced.

Figure 21:
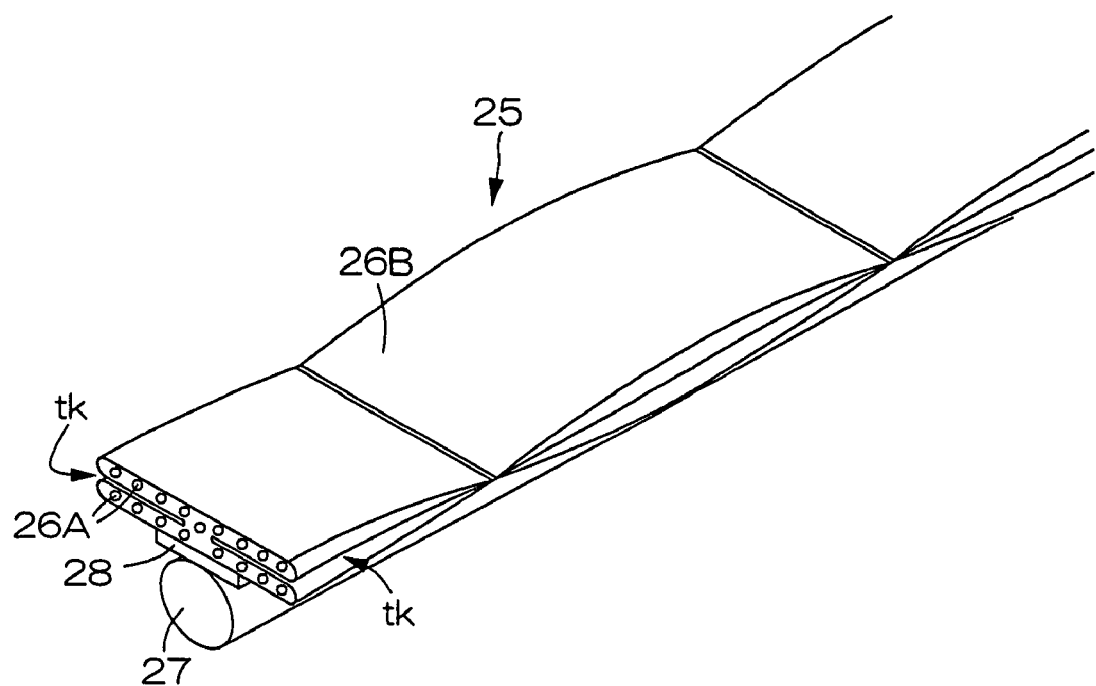
FIG. 21 is a perspective view of an example of another absorbent member.
Figure 22:
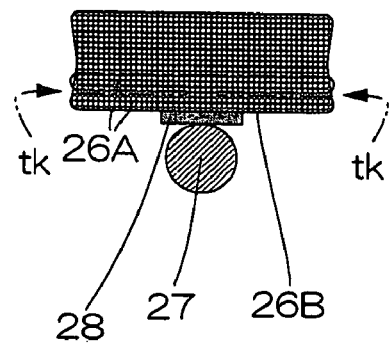
FIG. 22 is a cross sectional view showing a state at the time of absorbing body fluids in the example shown in FIG. 21.

Also in the aforementioned second expandable means, a plurality of the seal parts, s1, s1 . . . , formed by that the surfaces facing to each other in the direction of thickness of the pouch-like carrier 26B are bonded to each other in a continuous line from one end to the other end of the width direction of the pouch-like carrier 26B after the tucks, tk and tk, have been formed thereon may be provided with a spacing in the contraction direction of the absorbent member 25 as shown in FIG. 21, and as in the case of a seventh embodiment, the expansion to the width direction is restrained as shown in FIG. 22. Particularly, it is preferable that the tacks, tk and tk, are formed on both sides of the pouch-like carrier 26B with folding lines along the contraction direction as the illustrated embodiment, making the pouch-like carrier 26B readily expandable to the thickness direction.

2.2.3 Construction having the contraction material and the absorbent material for body fluids separable from each other As described in the section dealing with the intermittent arrangement of the highly absorbent polymer, the expansion of the absorbent material for body fluids at the portion of absorption of body fluids becomes a factor to inhibit the contraction of the contraction material practically united with the former. This problem may be solved by adopting the intermittent arrangement of the highly absorbent polymer. However, in the construction having the intermittent arrangement of the highly absorbent polymer, it is difficult to allow the highly absorbent polymer to be retained in a large amount in the carrier. As previously described, the embodiment in combination of the pouch-like carrier and the intermittent arrangement of the highly absorbent polymer can solve this contradictory problem. However, this embodiment has a demerit that the construction becomes complex.

In order to prevent the contraction material fundamentally from being inhibited in the contraction as well as simplify the construction, the embodiment proposed here is constructed such that the contraction material 27 and the absorbent material for body fluids 26 are united so as to be separated at the portion contacting body fluids in the absorbent member 25.

As a specific means for this, it is recommended that the unification of the contraction material 27 and the absorbent material for body fluids 26 is carried out by bonding (including adhesion in this case) using an adhesive whose adhesion force is weakened by contacting body fluids, for example, water dispersion-type hot melt adhesives constituted of polyvinyl alcohol, polyalkylene oxide, or the like as a main composition and water-soluble adhesives such as starch glue and carboxymethyl cellulose.

In this case, it is desirable to select adhesives, adhesion area and pattern (plane form, point form and the like besides various line forms such as spiral, linear and curved forms) and the like so that the adhesion force between the contraction material 27 and the absorbent material for body fluids 26 at the time of not contacting body fluids may become twice as large as that at the time of contacting body fluids.

Specific analysis concerning with the adhesion force provides the following: On wearing, the body pressure applied to the absorbent member by the wearer is usually from 50 to 100 g/cm$^2$. When a 3 cm wide ribbon-shape absorbent member is assumed to be used and this is moved, it would receive a resistance of from 300 to 1500 g/piece of the absorbent member (hereinafter simply referred to as "piece"). Accordingly, it is desirable that the adhesion force between the contraction material 27 and the absorbent material for body fluids 26 is 300 g/piece or more, particularly 1500 g/piece or more in a state not absorbing body fluids, and less than 300 g/piece, particularly less than 150 g/piece in a state absorbing body fluids. In connection to this, it is desirable that the contraction force of the contraction material is 300 g/piece or more, particularly 1500 g/piece or more and that the contraction force of the contraction material in a wet state is 300 g/piece or more, particularly 1500 g/piece or more. However, there are parts of the absorbent member and types of usage of the absorbent article which receive no body pressure at all. Accordingly, it is possible to make the adhesion force and the contraction force in such parts different from those in the parts receiving body pressure.

In this way, when the bonding part 28 contacts body fluids, the contraction material 27 and the absorbent material for body fluids 26 are separated from each other in said part contacting body fluids and thus the portion contacting body fluids of the contraction material 27 can contract freely without receiving restriction from the absorbent material for body fluids 26. At this time, the part not contacting body fluids of the contraction material 27 does not separate from the absorbent material for body fluids 26, and therefore, the absorbent material for body fluids 26 also contracts in association with the contraction of the contraction material 27. In this way, the absorbent material for body fluids 26 can contract efficiently.

In order to fulfill the same function, it is possible to construct in a way that the bonding force between the contraction material 27 and the absorbent material for body fluids 26 is made weak from the beginning irrespectively of contacting body fluids, thus being separated by the swelling force of the absorbent material for body fluids 26. In this instance, however, it is not possible to furnish different bonding forces between the portion contacting body fluids and the portion not contacting the body fluids, and therefore, the bonding at the portion not contacting body fluids is also removed by the influence of the aforementioned moving resistance of the absorbent member.

2.2.4 Other Constructions for the Absorbent Member

In the absorbent member 25 of the present invention, when the contraction material 27 is arranged at the center (when the pouch-like carrier is arranged in the folded state, it is the center of the width direction in the folded state) of the width direction (in this instance, the direction orthogonal to the contraction direction) of the carrier 26B, the contraction of the contraction material 27 acts on the carrier 26B uniformly in the width direction, which allows the absorbent member 25 to preferably contract lineally. In the illustrated examples, all are pursuant to this arrangement. In contrast, it is also possible that the width directional position of the carrier 26B is shifted such that, for example, the contraction material 27 is arranged to form a specified curve, thereby curving the direction of contraction intentionally.

When the pouch-like carrier is used, the compartments may be formed in a way that the compartments intersect two-dimensionally to one another, for example, in a grid shape, honeycomb shape and the like.

3 Second Embodiment

Hitherto, a variety of examples of the absorbent member of the present invention have been described, while there is plenty of scope for improving several parts other than the absorbent member in order to enhance the fundamental function of the present invention, that is, renewal function of the absorbent member. Hereinafter, preferable examples will be described for the parts other than the absorbent member.

Figure 23:
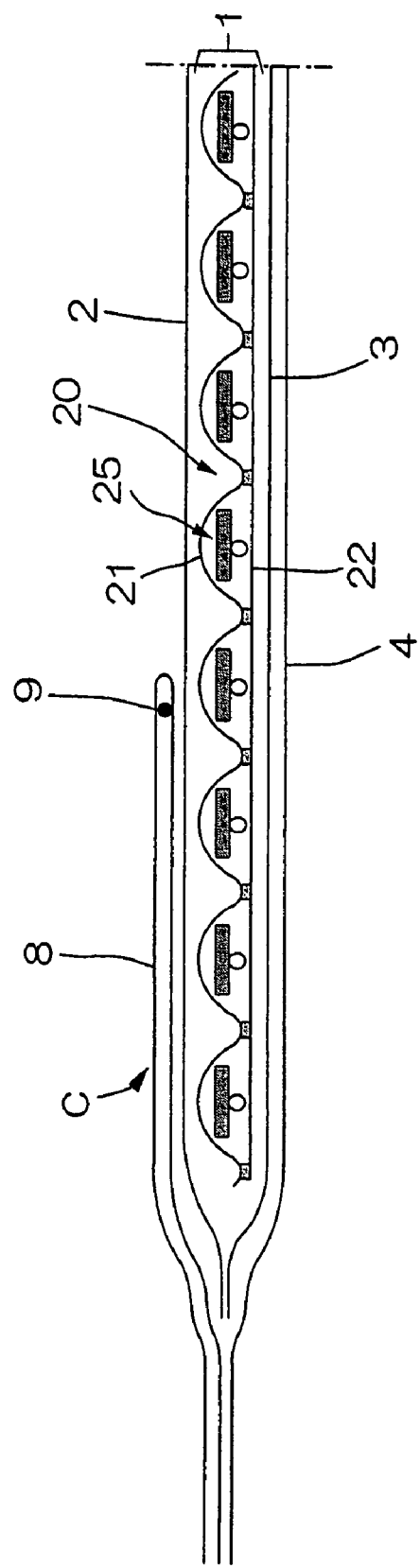
FIG. 23 is a longitudinal cross sectional view of a main part of a second embodiment.
Figure 24:
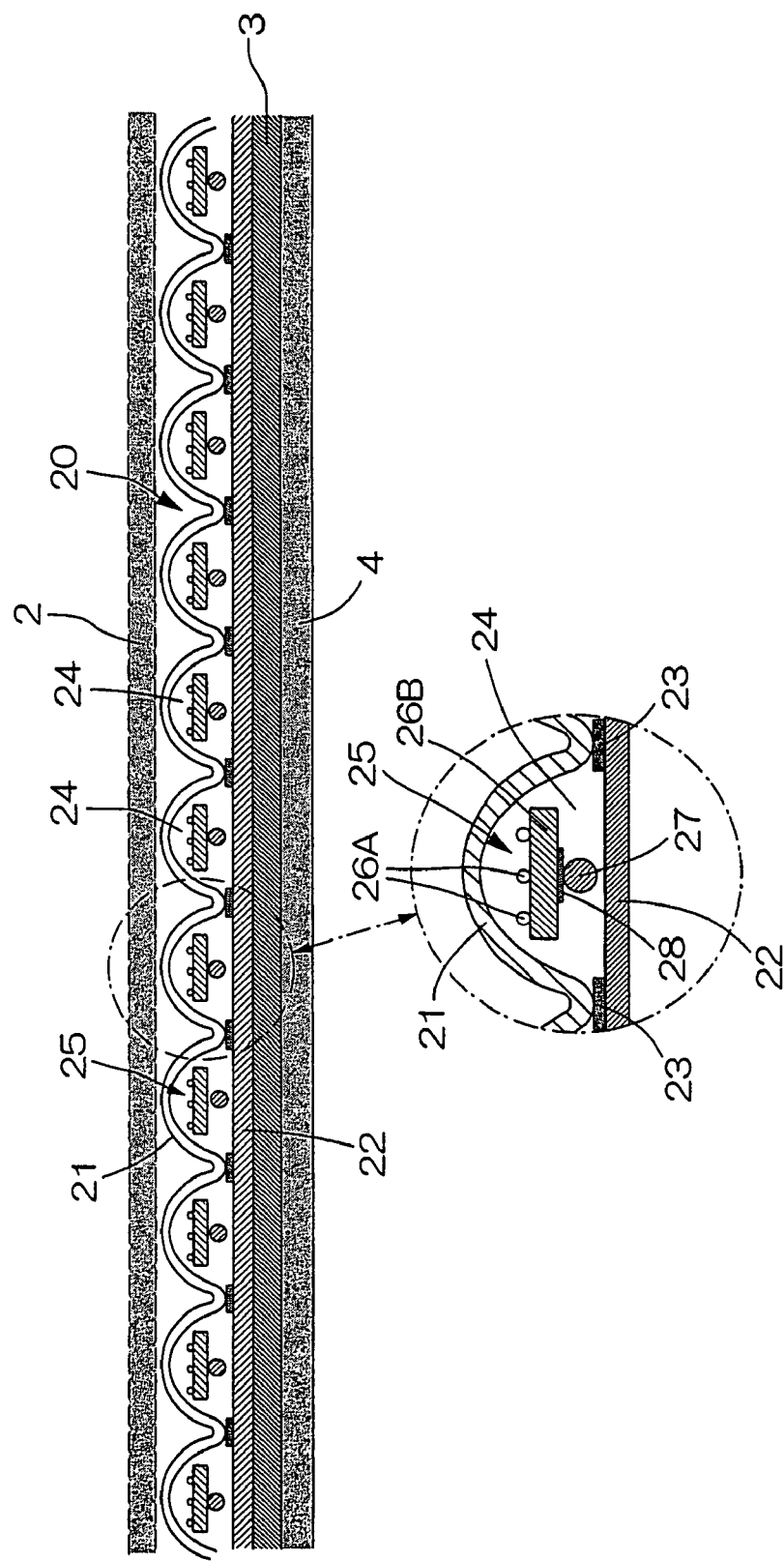
FIG. 24 is a longitudinal cross sectional view of the main part of the second embodiment.
Figure 25:
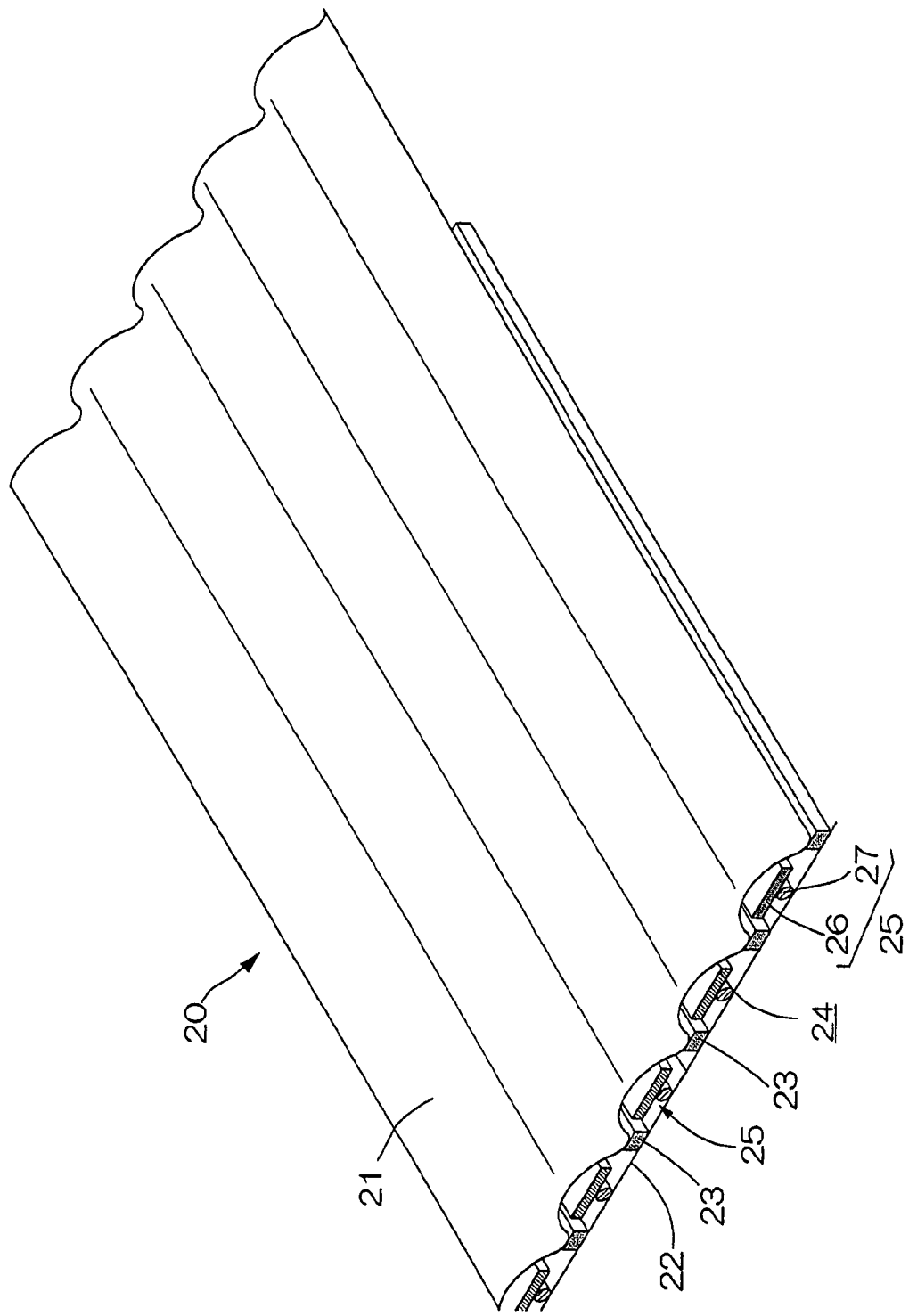
FIG. 25 is a perspective view of an absorbent body for body fluids of the second embodiment.

The example shown in FIGS. 23 to 25 is constructed such that a use-surface side sheet 21 and a back-surface side sheet 22 are provided, along the longitudinal direction, with fixing parts 23 at the positions spaced in-between in the width direction of the product, the space between the adjacent fixing parts, 23 and 23, serves as a channel space 24 along the longitudinal direction, the absorbent member 25 is placed within each channel space 24, 24 . . . , and these solely constitute the absorbent portion for body fluids 1 as an absorption body for body fluids 20. The fundamental construction of the article in the illustrated example is the same as that in FIG. 2. Accordingly, the body skin-facing side of the use-surface side sheet 21 of the absorption body for body fluids 20 is covered with the surface sheet 2, and the side farther from the body skin of the back-surface side sheet 22 of the absorption body for body fluids 20 is covered with the leakproof layer 3. For the absorbent member 25, all of the specific examples described previously are usable, and the absorbent member 25 illustrated above in FIG. 4 or FIG. 7 is being used in the illustrated example.

The aforementioned renewal function and the like of the absorbent member of the present invention are fulfilled by arranging the absorption body for body fluids 20 constructed as described above in the absorbent portion for body fluids 1.

In more detail, an excreted fluid, for example, urine passes through the surface sheet 2, contacts the carrier 26B via the use-surface side sheet 21 and diffuses along the carrier 26B, and when the urine contacts the contraction material 27, the latter itself contracts, accompanying the contraction of the absorbent material for body fluids 26 which is practically united with the contraction material. As the result, the portion of the absorbent material for body fluids 26 which has initially absorbed the body fluid becomes displaced from the excretory part of the body fluid and in turn, a new part of the absorbent material for body fluids 26 is located. In other words, the absorption part of the absorbent material for body fluids 26 is renewably displaced at the excretory part of the body fluid in accordance with the excretion of the body fluid. Therefore, the whole part of the absorbent member 25 is utilized efficiently, and as a whole, an absorbent article for body fluids in which the absorption body for body fluids 20 has a large absorption volume in spite of being in a thin form and may be endured for a long time wearing can be obtained.

In addition, when the absorbent material for body fluids 26 contracts in accordance with the contraction of the contraction material 27 by contacting body fluids, the absorption part of the absorbent material for body fluids 26 made of the highly water-absorbent polymer 26A is renewed at the excretory part of the body fluid, and therefore the function of the highly water-absorbent polymer 26A is fulfilled perfectly without having a so-called gel blocking phenomenon in which expanded wetting is inhibited by swelling of the highly absorbent polymer 26A.

And when the absorbent member 25 is contained in the channel space 24 as in the case of this construction, the contraction of the absorbent member 25 accompanied by the contraction of the contraction material 27 proceeds smoothly without fail. Further, body fluids can move and diffuse longitudinally through the inside of the channel space 24. Furthermore, when the article is worn, the channel space 24 serves as a buffering part or cushion and the touch becomes excellent.

Cross sectional shape of the channel space 24 and its number are selected appropriately. A plurality of the absorbent members 25 may also be collocated in one channel space 24 (not illustrated).

Important physical characteristics for the contraction material 27 are the contraction force and contraction percentage at the time of absorbing water. Considering that, when the absorbent member 25 moves within the channel space 24, the contraction force is lowered by the friction between the absorption part of the absorbent member 25 and the inner wall of the channel, it is desirable that the contraction material 27 is determined by taking the cross sectional area of the channel space 24 and the degree of swelling of the highly water-absorbent polymer 26A into account. It is possible for the highly water-absorbent polymer 26A to move satisfactorily after absorption as long as the contraction percentage of the contraction material 27 in its original yarn is 30% or more, preferably 70% or more.

The cross sectional area S of the channel space 24 varies depending on the shape of the absorbent member 25, and a preferable area is calculated by the following equation:

$$S = (30\text{-}200) \times a/b \qquad (1)$$

where a=g of the highly water-absorbent polymer/cm of the absorbent member, b=contraction percentage of the contraction material (length after contraction/length before contraction), S=cross sectional area ($cm^2$).

The material of the use-surface side sheet 21 to form the channel space 24 is not limited as long as it is liquid-permeable, and may be made of, for example, porous film and the like besides non-woven fabric. In this case, the material should preferably have pores small enough not to allow passage of the highly water-absorbent polymer 26A. The back-surface side sheet 22 bonded to the use-surface side sheet 21 may be selected from non-woven fabric, leakproof sheet, wetproof paper, absorbent paper and the like.

In the constructions shown in FIGS. 23 to 25, the absorption body for body fluids 20 is placed between the surface sheet 2 and the leakproof layer 3, and the use-surface side sheet 21 itself is permeated by body fluids and covers the absorbent member 25. Accordingly, the use-surface side sheet 21 itself can serve as "a surface layer" referred to in the present invention, that is, the surface layer 2 may be omitted. Moreover, even if the channel space 24 is provided, the absorbent member 25 may be placed outside of the channel space 24 as long as it can contract. That is, the arrangement place of the absorbent member 25 may be selected appropriately.

4 Third Embodiment

On the other hand, in the present invention, the absorbent member contracts by itself upon contacting body fluids; unless a sufficient amount of body fluids is supplied to the absorbent member, the effective contraction can not be expected to be achieved because the contraction of the absorbent member becomes poor. In particular, when the absorbent member 25 is composed of the absorbent material for body fluids and the contraction material, the contraction material and the highly absorbent polymer compete for absorbing body fluids, and when the highly absorbent polymer has absorbed up body fluids before the contraction material absorbs the body fluids to a sufficient degree, the contraction material can no longer contracts and the aforementioned renewal of the absorbent material for body fluids may not be fulfilled. Since the absorption rates of body fluids of most of currently available contraction materials are slower compared with those of the highly absorbent polymers which are preferably used as the absorbent material for body fluids, it is known that incomplete renewals are frequently experienced during the contraction.

Figure 26:
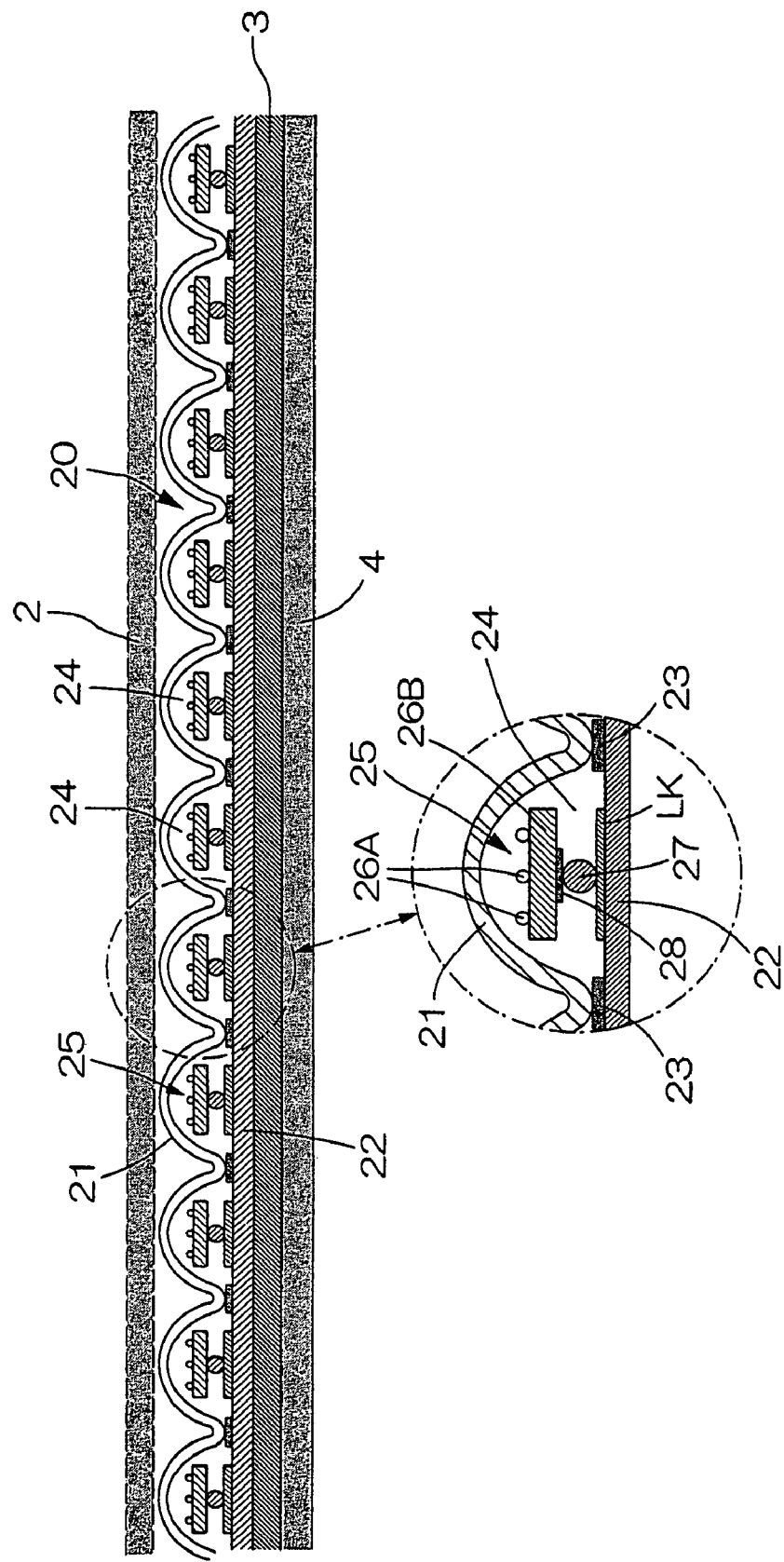
FIG. 26 is a longitudinal cross sectional view of a main part of a third embodiment.
Figure 27:
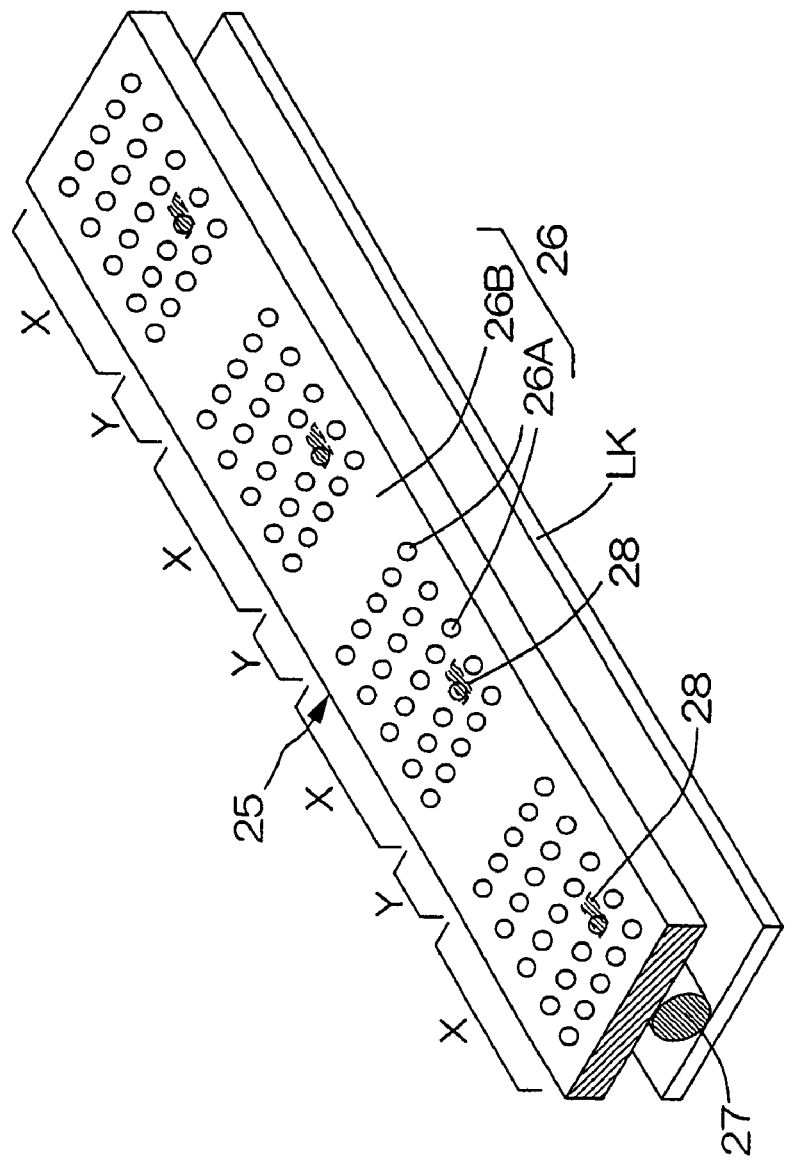
FIG. 27 is a perspective view showing an arrangement example of a liquid-retaining member on the absorbent member.

In order to solve this problem, it is recommended, therefore, to arrange a liquid-retaining member LK which is in contact with the absorbent member 25 as shown in FIG. 26 and FIG. 27. In case where the absorbent member 25 is composed of the absorbent material for body fluids 26 and the contraction material 27 and particularly when the absorbent material for body fluids 26 contains the highly absorbent polymer 26A having a high absorption rate, the liquid-retaining member LK is desirably arranged in contact with the contraction material 27. At this time, the liquid-retaining member LK may be fixed to the carrier 26B, the contraction material 27 or the back-surface side sheet 3, or may not be fixed at all, as long as the liquid-retaining member LK fulfills its function by contacting the contraction material 27.

In this way, the body fluids excreted onto the article are retained in the liquid-retaining member LK, resulting in supplying the absorbent member 25 with body fluids sufficient for its contraction.

As the liquid-retaining member LK, a weakly hydrophilic sheet capable of retaining water may suffice, and tissue paper or non-woven fabric may preferably be used from liquid-retaining property and the view point of cost. More specifically, paper with a property of absorbing body fluids including non-woven fabric made hydrophilic and having a basis weight of approximately from 10 to 20 g/m$^2$ (well-known non-woven fabric, for example, spunbonded non-woven fabric, carded web-bonded non-woven fabric, meltblown non-woven fabric, combinations thereof and the like) and thin paper (tissue paper) having a basis weight of approximately from 10 to 20 g/m$^2$ may preferably be used. By using these, effective contraction of the absorbent member 25 may become possible as described previously.

As in the illustrated example in particular, when the liquid-retaining member LK is arranged between the absorbent member 25 and the liquid-impermeable back-surface side sheet 22 (leakproof layer), there is an advantage that the liquid-retaining member reduces the friction between the absorbent member and the leakproof layer on wetting, making the contraction easy.

The shape, size, and arrangement for the contraction material of the liquid-retaining member LK of the present invention may be determined appropriately as long as the liquid-retaining member LK contacts the absorbent member 25. When the contraction material 27 is arranged to be interposed between the liquid-retaining member LK and the absorbent material for body fluids 26 as illustrated, body fluids are retained amply in the liquid-retaining member LK itself and the interspace between the liquid-retaining member LK and the absorbent material for body fluids 26, and thus preferably supplying a sufficient amount of body fluids to the contraction material 27. Further in the present invention, the liquid-retaining member may be arranged between the contraction material 27 and the absorbent material for body fluids, the contraction material 27 may be wrapped around by the liquid-retaining member, or the contraction material 27 may be interposed between a pair of the liquid-retaining members (not illustrated). The liquid-retaining member LK may preferably be extended continuously over the entire contraction direction of the contraction material, for example, in a band shape, while it is also possible that the liquid-retaining members LK are arranged intermittently so as to correspond only to the specified part of the contraction material 27 or arranged continuously or intermittently over a plurality of the contraction materials 27. Specific examples of the above will be described later.

As illustrated, when the liquid-retaining member LK is constructed so as not to protrude from the side edges of the absorbent material for body fluids 26 as well as to have at least a width enough to cover practically the entire width direction of the contraction material 27, the necessary and sufficient size is met for the liquid-retaining member LK in contracting the contraction material, reducing the cost of the member.

Figure 28:
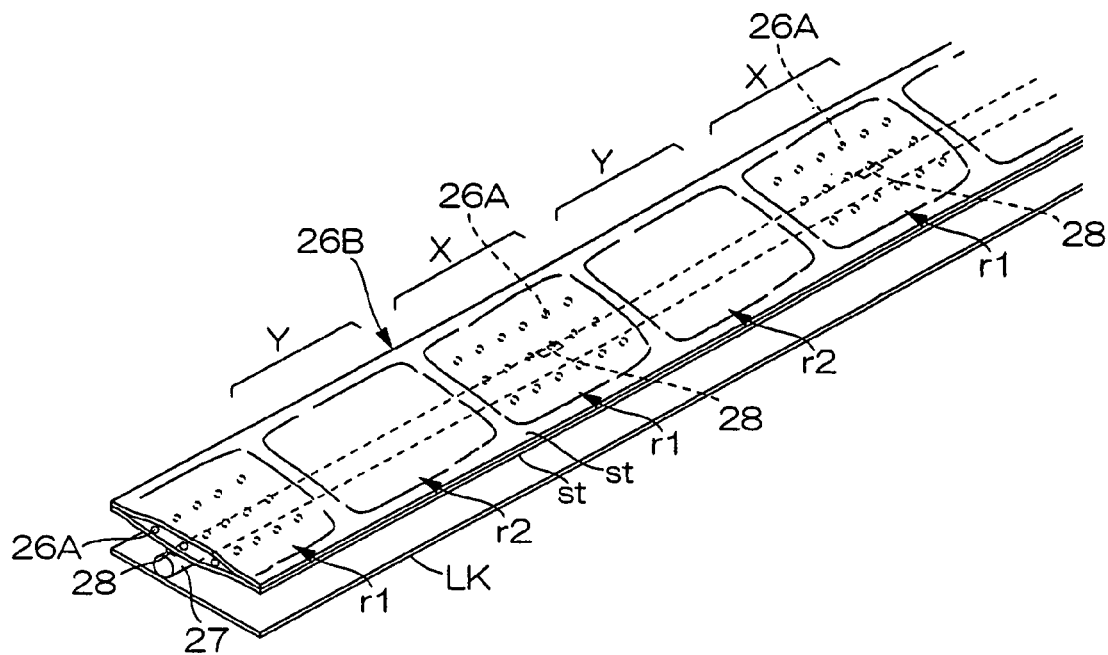
FIG. 28 is a perspective view showing an arrangement example of the liquid-retaining member on another absorbent member.
Figure 29:
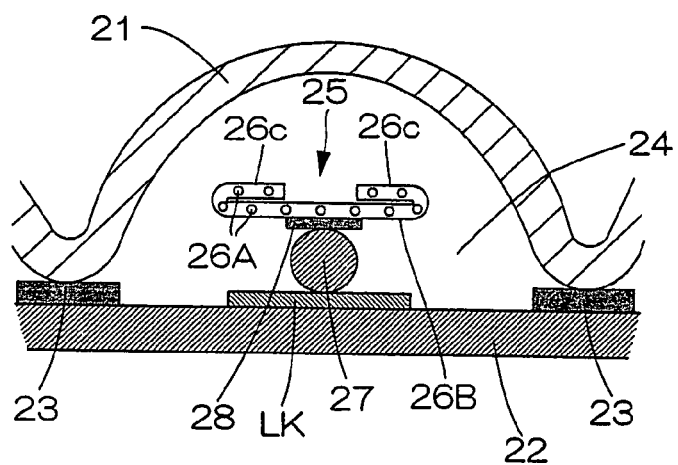
FIG. 29 is a cross sectional view of a main part showing an arrangement example of the liquid-retaining member on another absorbent member.
Figure 30:
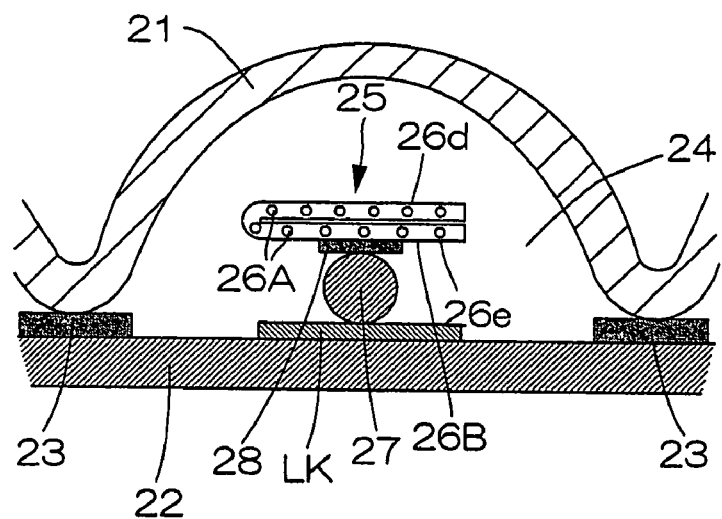
FIG. 30 is a cross sectional view of a main part showing an arrangement example of the liquid-retaining member on another absorbent member.
Figure 31:
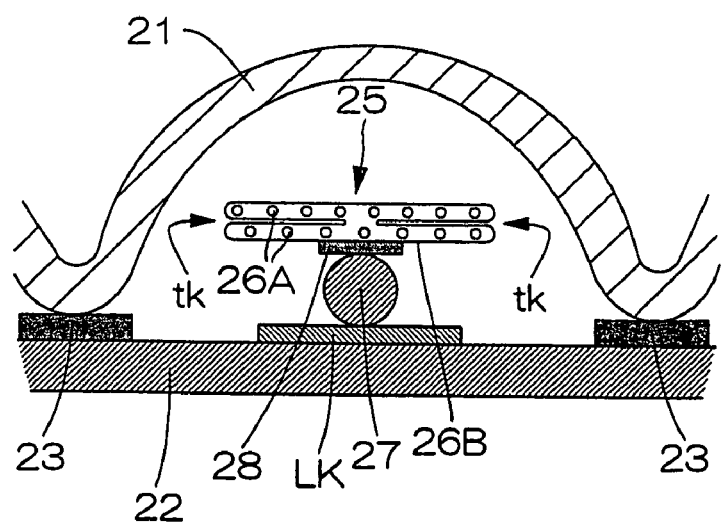
FIG. 31 is a cross sectional view of a main part showing an arrangement example of the liquid-retaining member on another absorbent member.

As to the absorbent member 25, all of the aforementioned specific examples can be used. In the constructions shown in FIG. 26 and FIG. 27, the aforementioned absorbent member 25 in FIG. 4 or FIG. 7 is used. FIG. 28 illustrates an example of arrangement of the liquid-retaining member LK when the aforementioned pouch-like carrier 26B shown in FIG. 9 is used. FIG. 29, FIG. 30 and FIG. 31 show examples of arrangement of the liquid-retaining member LK for the constructions shown in FIG. 11, FIG. 15 and FIG. 16, respectively.

In the examples shown in FIG. 26 and FIG. 27, the form in which the absorbent member 25 is placed within the channel space 24 of the second embodiment is adopted and therefore, the liquid-retaining member LK is arranged within the channel space. However, the liquid-retaining member of the present invention may be arranged anywhere as long as it is arranged in contact with the absorbent member 25. In addition, the liquid-retaining member may be applied to the construction not having the channel space 24 or the like and to all of the constructions described previously or to be described later.

5 Fourth Embodiment

The aforementioned channel space 24 in itself is designed to have a very effective construction, but there is the possibility that it may be crushed and deformed by receiving a pressure from the side facing the body skin during wearing the article and the like and that the desirable effect may not be fulfilled.

Figure 32:
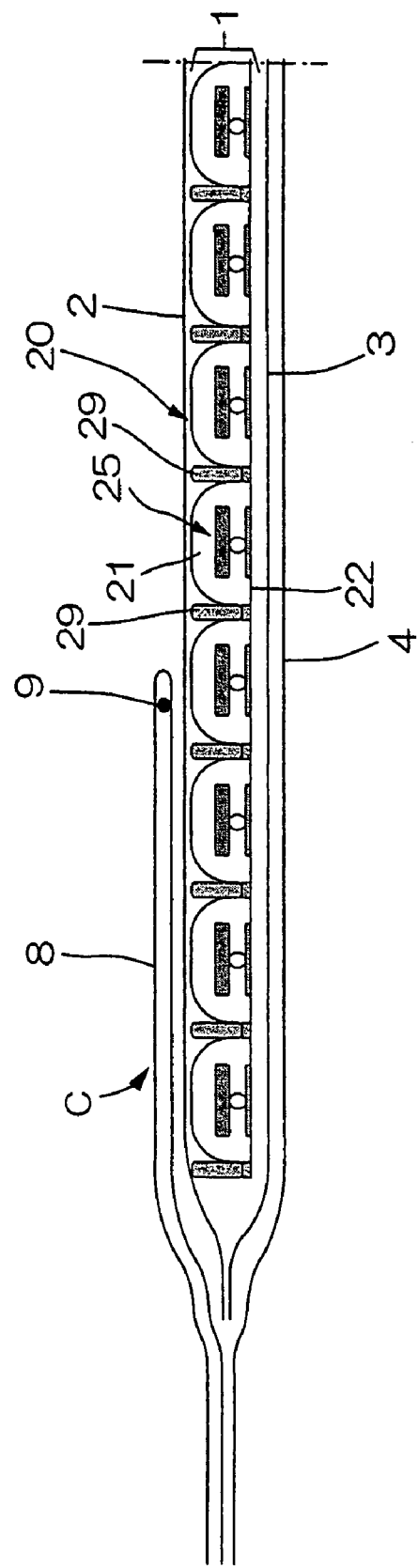
FIG. 32 is a longitudinal cross sectional view of a main part of a fourth embodiment.
Figure 33:
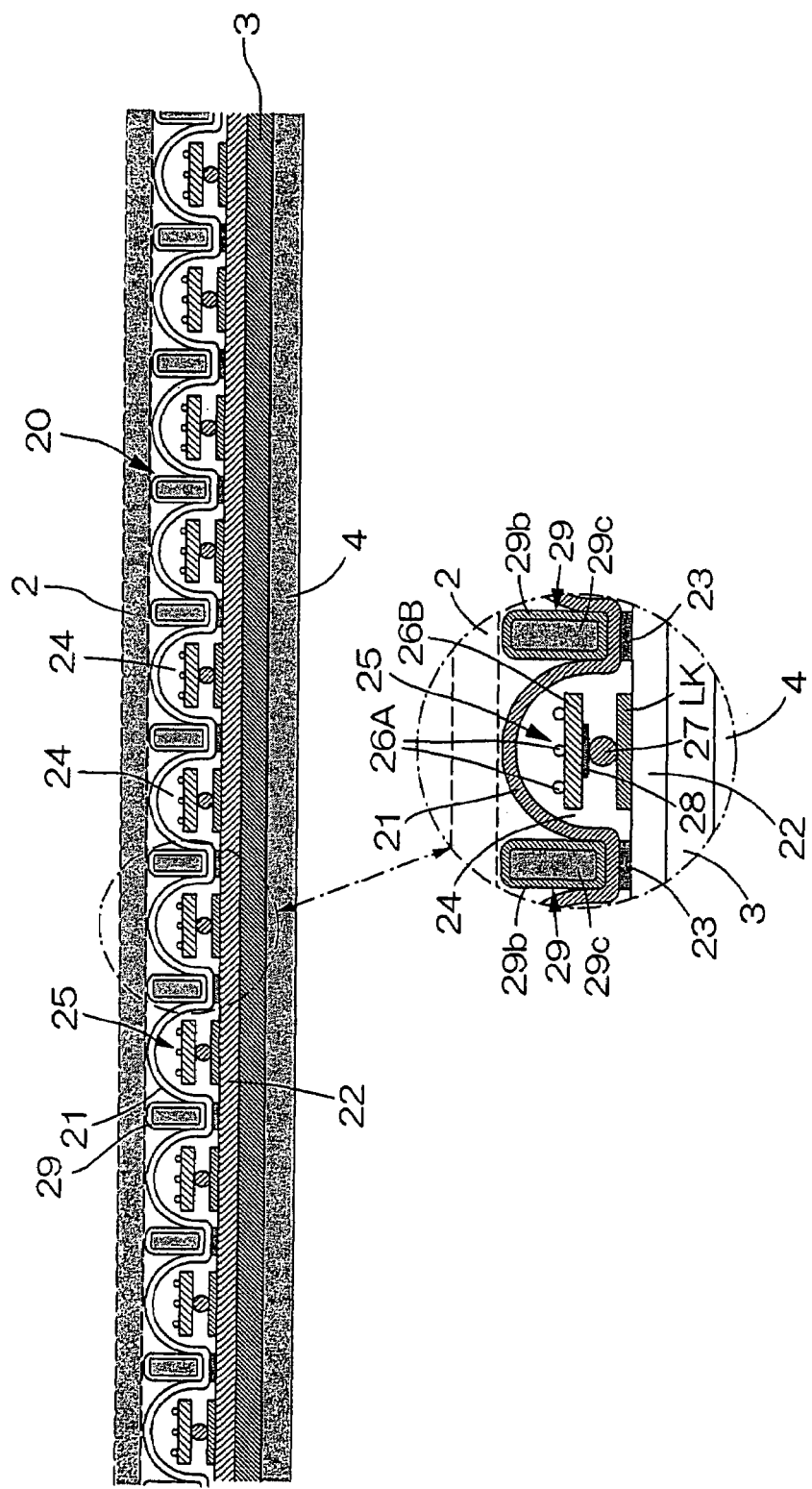
FIG. 33 is a longitudinal cross sectional view of the main part of the fourth embodiment.
Figure 34:
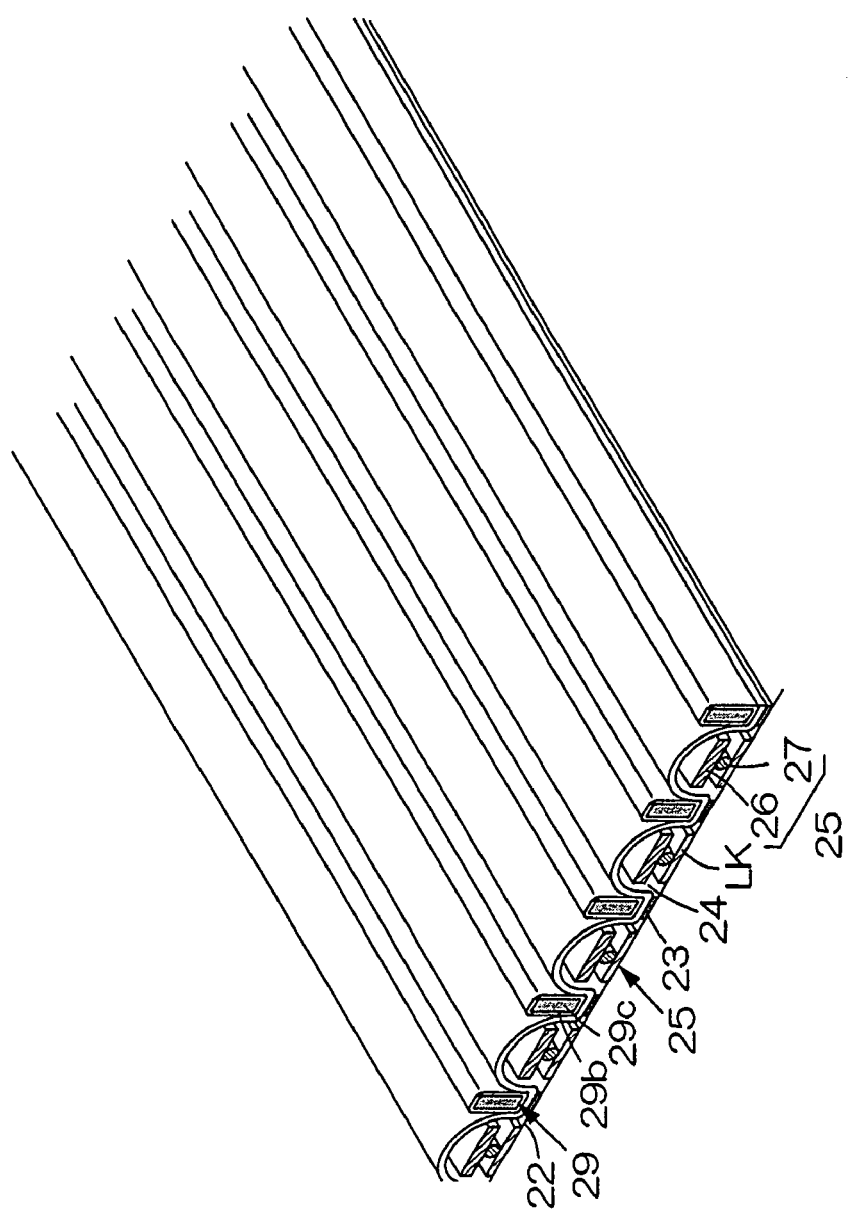
FIG. 34 is a perspective view of the main part of the fourth embodiment.

Accordingly, the proposed embodiment is made such that a plurality of cushion members, 29, 29 . . . , are arranged as well as the absorbent members are placed between the cushion members, 29, 29 . . . as shown in FIG. 32. In the construction shown in FIG. 32 and as shown in FIG. 33 and FIG. 34 as well where the absorbent members 25 are arranged within the aforementioned channel spaces 24, 24 . . . as a basic feature, the cushion members, 29 and 29, are placed respectively at the locations corresponding to the fixing parts 23 for fixing the use-surface side sheet 21 and the back-surface side sheet 22 on the upper side of the use-surface side sheet 21 (the side facing to the body skin). In this case, the cushion members 29 may be fixed within the absorbent portion for body fluids 1 by means of hot melt bonding, heat seal bonding and the like or may be simply placed on without being fixed.

Figure 35:
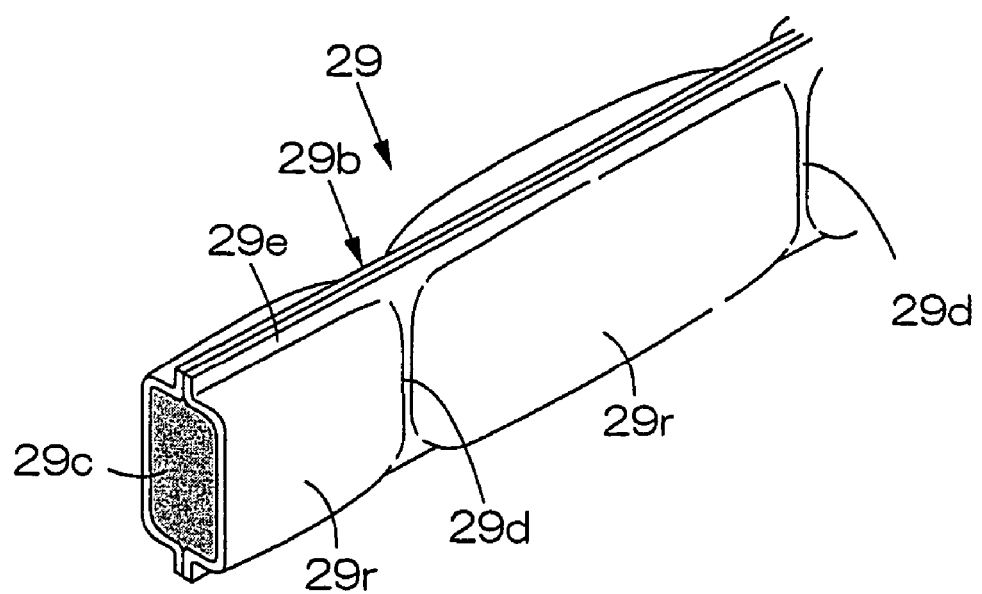
FIG. 35 is a perspective view of a cushion member of the fourth embodiment.

The cushion member 29 may suffice as long as it has a cushioning property, and fiber aggregates or sponge body alone may suffice for it. The cushion member 29 is preferably formed by including a cushioning absorbent material for body fluids 29c in a closed pouch-like body 29b made of a sheet permeable to body fluids as shown in FIG. 35. For the sheet permeable to body fluids, non-woven fabric may be used and for the cushioning absorbent material for body fluids 29c, materials known in absorbent articles, for example, highly absorbent polymer, cotton sponge, natural sponge, or their mixture, and the like may be used. The shape of the cushion member 29 may be determined appropriately, and when it is considered that the absorbent member 25 is arranged in-between, a slender shape as illustrated is preferable.

In addition, when the pouch-like body 29b for the cushion member 29 is constructed such that the pouch-like body 29b is partitioned in the longitudinal direction of the article to have a plurality of compartments, 29r, 29r . . . , and then the cushioning absorbent materials 29c for body fluids are contained in the compartments, 29r, 29r . . . , respectively, the cushioning property is distributed uniformly in the longitudinal direction because the cushioning material 29c is restrained in the longitudinal direction of the pouch-like body 29, which hardly makes the distribution uneven. The partition 29d is formed by bonding the inner surfaces of the cushion member 29 to each other at predetermined places using hot melt bonding, heat seal bonding, or the like.

It is also preferable that the partitions 29d are constructed such that the parts partitioned become removable on contacting body fluids. However, if a peripheral bonding part 29e of the pouch-like body 29 (including the bonding part at both longitudinal edges) is removed, the cushioning material 29c is released from the inside of the pouch-like body 29, resulting in a loss of cushioning, and therefore said peripheral bonding part 29e is constructed not to be removed using an adhesive or bonding means having a bonding force which is not weakened by contacting body fluids.

In order to achieve removal of such partitioning, the partitions, 29d, 29d . . . , are either constructed so as to become separable on contacting body fluids in the same way as that described for the removal of the partition of the pouch-like carrier or constructed so as not to be removed by contacting body fluids only but removed by swelling force of the inner cushioning absorbent material 29c. The former case of the partition d may be formed by bonding the inner surfaces of the pouch-like body 26B to each other using an adhesive separable on contacting body fluids. The adhesive separable on contacting body fluids to be used includes water dispersion-type hot melt adhesives constituted of polyvinyl alcohol, polyalkylene oxide, or the like as a main composition and water-soluble hot melt adhesives such as starch glue and carboxymethyl cellulose. Herein, the term used in the present invention "bonding" with "an adhesive separable on contacting body fluids" includes both bonding fixation and adhesion fixation in a general sense. A partitioning formed by such bonding has an advantage that it is applicable irrespectively of the kind of the cushioning material 29c. On the other hand, the latter case of the partitions, d, d . . . , is formed by bonding (including "by adhesion") the inner surfaces of the pouch-like body 26B to each other with a bonding force weak enough to be separated by the swelling force of the cushioning material 29c. However, a cushioning material not swelled by absorbing body fluids can not be selected. Accordingly, the latter case is considered to be suitable when the highly absorbent polymer is used as the cushioning material 29c.

When the absorbent member 25 is arranged between the cushion members, 29 and 29, a pressure applied from the side facing the body skin is sustained by these cushion members 29 and 29, spaces for both contraction of the absorbent member 25 and flow channels for body fluids may be reserved in-between, and even if the pressure applied from the wearer's body to the absorbent member 25 side is high during wearing, the spaces for contraction of the absorbent member 25 may be reserved without fail, thereby permitting assured and efficient renewal of the absorbent member 25 as well as efficient absorption of body fluids.

In addition, the contraction of the absorbent member 25 in association with the contraction of the contraction material 27 proceeds smoothly without fail, when the absorbent member 25 is arranged within the channel space 24 as illustrated in the embodiment. In this case, the channel space 24 hardly becomes crushed owing to the supporting action of the cushion members, 29, 29 . . . , and body fluids can easily move and diffuse in the channel space 24.

Furthermore, in case where the cushion member 29 is formed so as to enclose the cushioning material 29c to absorb body fluids in the closed pouch-like body 29b consisting of the sheet permeable to body fluids, circumstantial absorption of body fluids occurs in the cushioning material 29c, which restrains wetting from spreading toward the width direction of the product as well as facilitates spreading of wetting along the longitudinal direction of the product. Thus, so-called side leak which has been problematic up to now in disposable diapers and sanitary napkins may be effectively prevented.

Still further, in case where the partition 29d to be removed by contacting body fluids is arranged in the pouch-like body 29b of the cushion member 29, when the cushioning absorbent material for body fluids 29c in the cushion member 29 is swelled by absorbing body fluids, the partition 29d is removed at the same time of contacting body fluids and the shape of a compartment 29r may change naturally to a stable form. Therefore, it hardly occurs that the cushion member 29 falls down sideways or locally swells out, thereby creating a situation in which spaces for contraction of the absorbent member 25 are lost; the primary function of the cushion member 29 is not inhibited by absorbing body fluids but fulfilled without fail at all times. This action effect will be explained in more detail in the examples to be described later with reference to several accompanying drawings.

Although not illustrated, all of the aforementioned specific examples may be used as the absorbent member 25 for this embodiment. And in the examples shown in FIGS. 32 to 34, the cushion members, 29, 29 . . . , are arranged outside of the channel space 24 adopting the basic feature of the second embodiment where the absorbent member 25 is arranged within the channel space 24, while the cushion members 29 of the present invention may be arranged anywhere as long as the absorbent member 25 is interposed in-between. In addition, the cushion member 29 of the present invention may be applied to the construction not having the channel space 24 or the like and to all of the constructions described previously or to be described later.

6 Fifth Embodiment

In currently commercially-available paper diapers, non-contracting absorbent members which are formed by wrapping a rectangular absorption core, composed mainly of flocculent pulp (flap pulp) and having certain rigidity (semirigid), with crepe paper are arranged in the absorbent portion for body fluids. In the present invention, the aforementioned absorbent member 25 may be arranged together with this non-contracting absorbent member. In this case, the absorbent member 25 to contract may be arranged at an appropriate place, for example, an appropriate place inside or outside of the non-contracting absorbent member, specifically at the place between the surface sheet and the crepe paper, between the crepe paper and the absorption core, within the absorption core, between the crepe paper and the leakproof sheet, and the like (not illustrated).

7 Arrangement, Fixing, Etc. of the Absorbent Member

The absorbent member 25 of the present invention may not be fixed to the article as long as it is arranged to be able to contract in the article but is preferably provided with a fixing part 30, a part of which is fixed to the article by means of, for example, an adhesive, heat melt bonding (fusion) and the like. The fixing of the absorbent member 25 may be carried out by bonding to the surrounding member, for example, the leakproof layer 3 in the first embodiment, the back-surface side sheet 22 in the second embodiment and the like using an adhesive. By providing such fixing parts at appropriate places, when the absorbent member 25 contracts owing to absorbing body fluids as described above and shown in FIG. 3, the absorbent member 25 is displaced so as to be drawn toward the fixing part 30 and a body fluid-absorbing part Z is renewed by an unsoaked part of the absorbent member 25.

7.1 Arrangement Example 1

Figure 36:
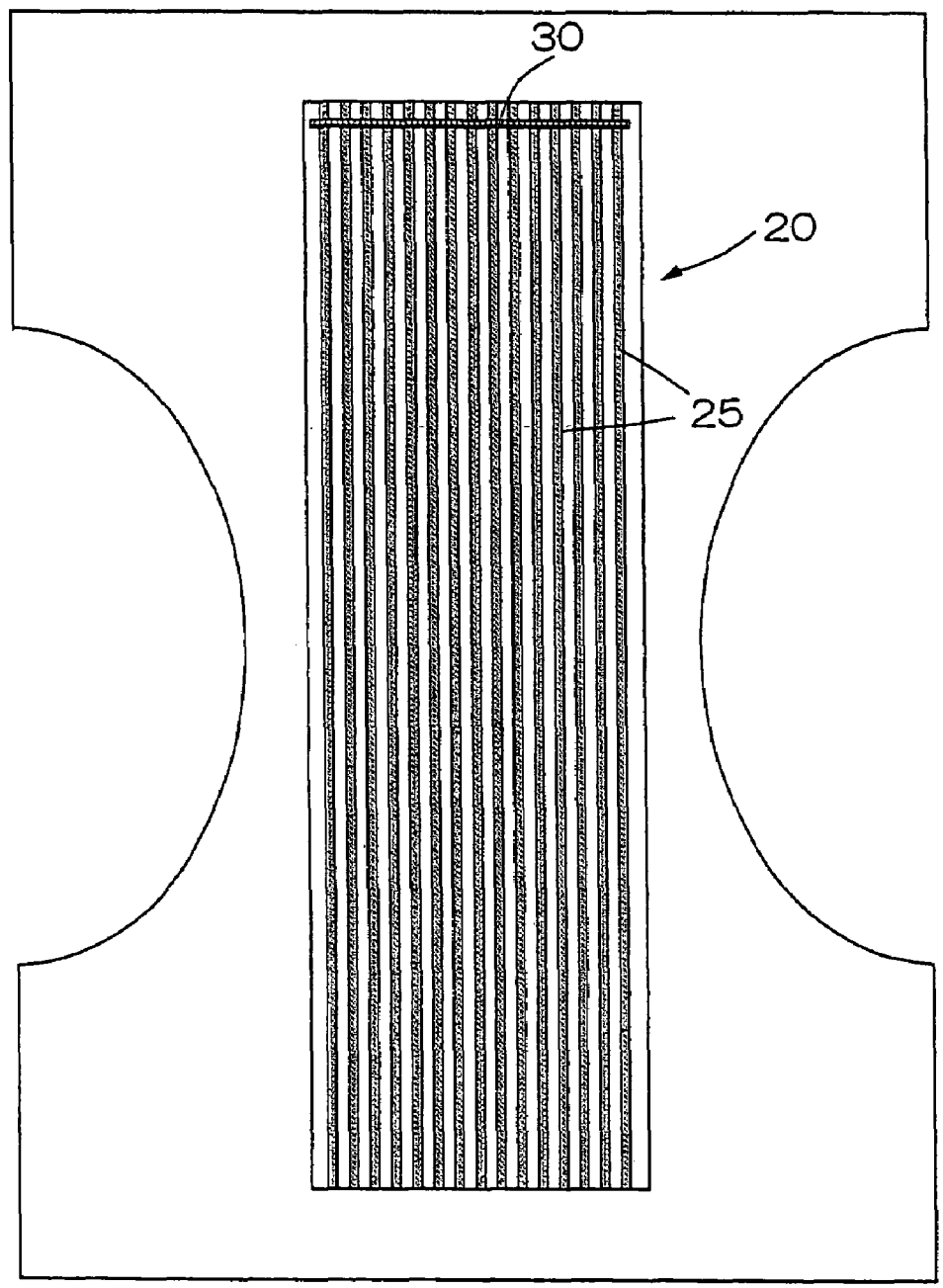
FIG. 36 is a plan view showing an arrangement example of the absorbent member.

The absorbent member 25 of the present invention is desirably arranged along the longitudinal direction (anterior posterior direction). of the product as shown in FIG. 36. In the illustrated example, the common end parts of a group of the absorbent members, 25, 25 . . . , constitute the fixing part 30.

In the present invention, it should be noted that the absorbent member is not limited to being arranged along the longitudinal direction but may be arranged in an arbitrary direction such as the width direction of the product. In addition, when a plurality of the absorbent members are arranged, these absorbent members may be arranged in directions different from one another or may cross one another.

7.2 Arrangement Example 2

Figure 37:
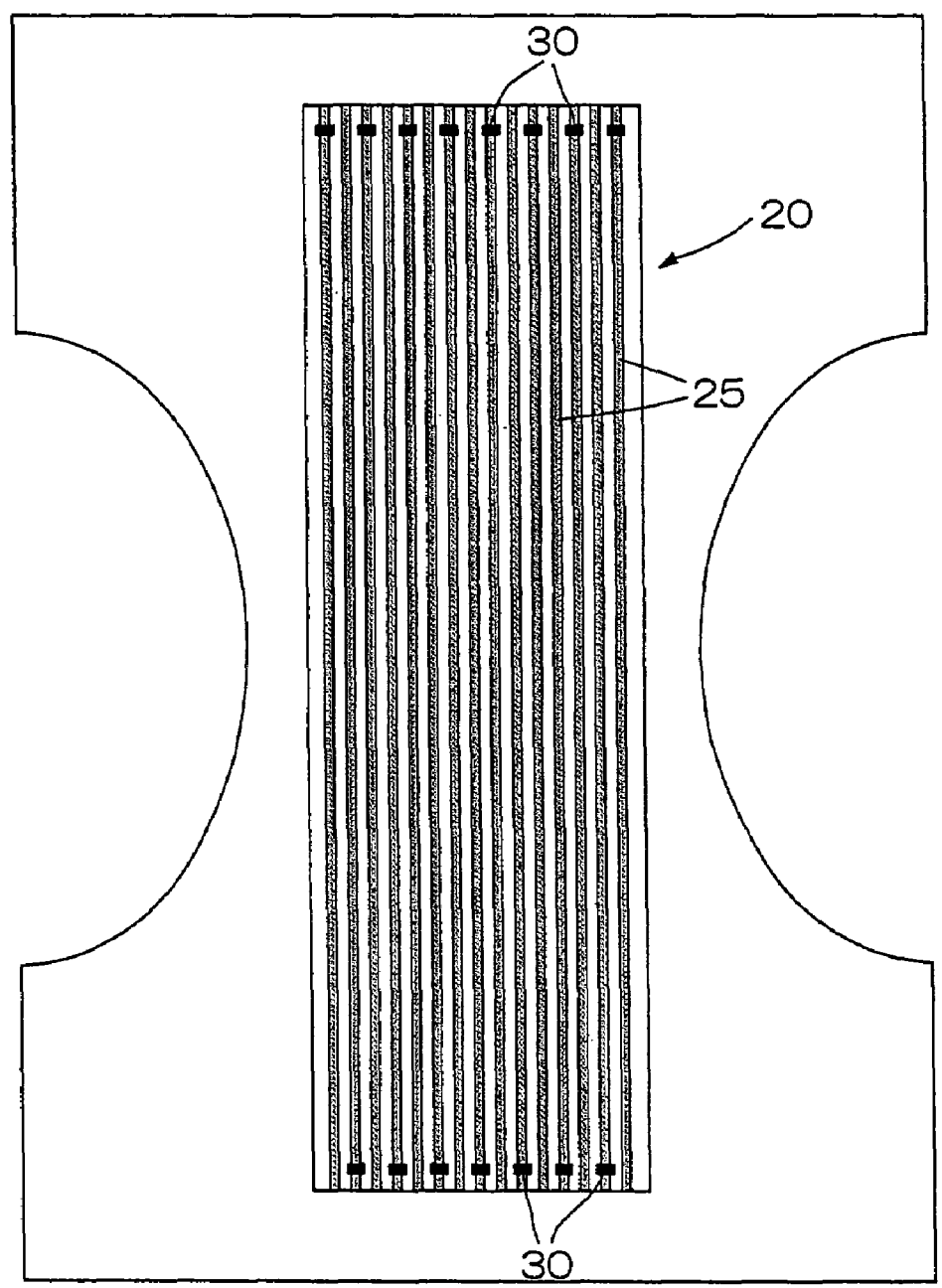
FIG. 37 is a plan view showing another arrangement example of the absorbent member.
Figure 38:
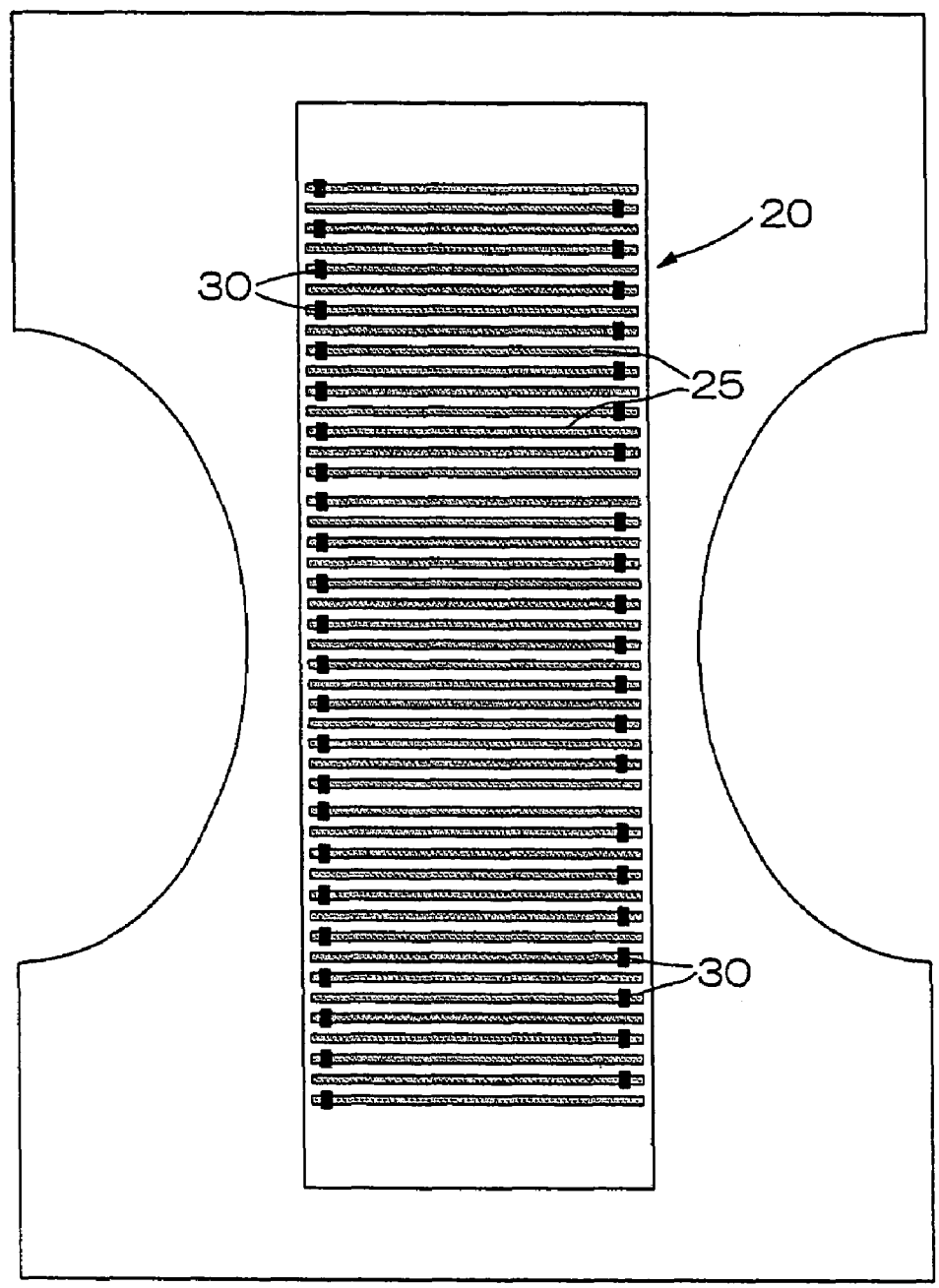
FIG. 38 is a plan view showing another arrangement example of the absorbent member.

As illustrated in FIG. 37 and FIG. 38, the staggered arrangement of the fixing part 30 is also an effective embodiment for a plurality of the absorbent members 25 placed side by side.

7.3 Arrangement Example 3

Figure 39:
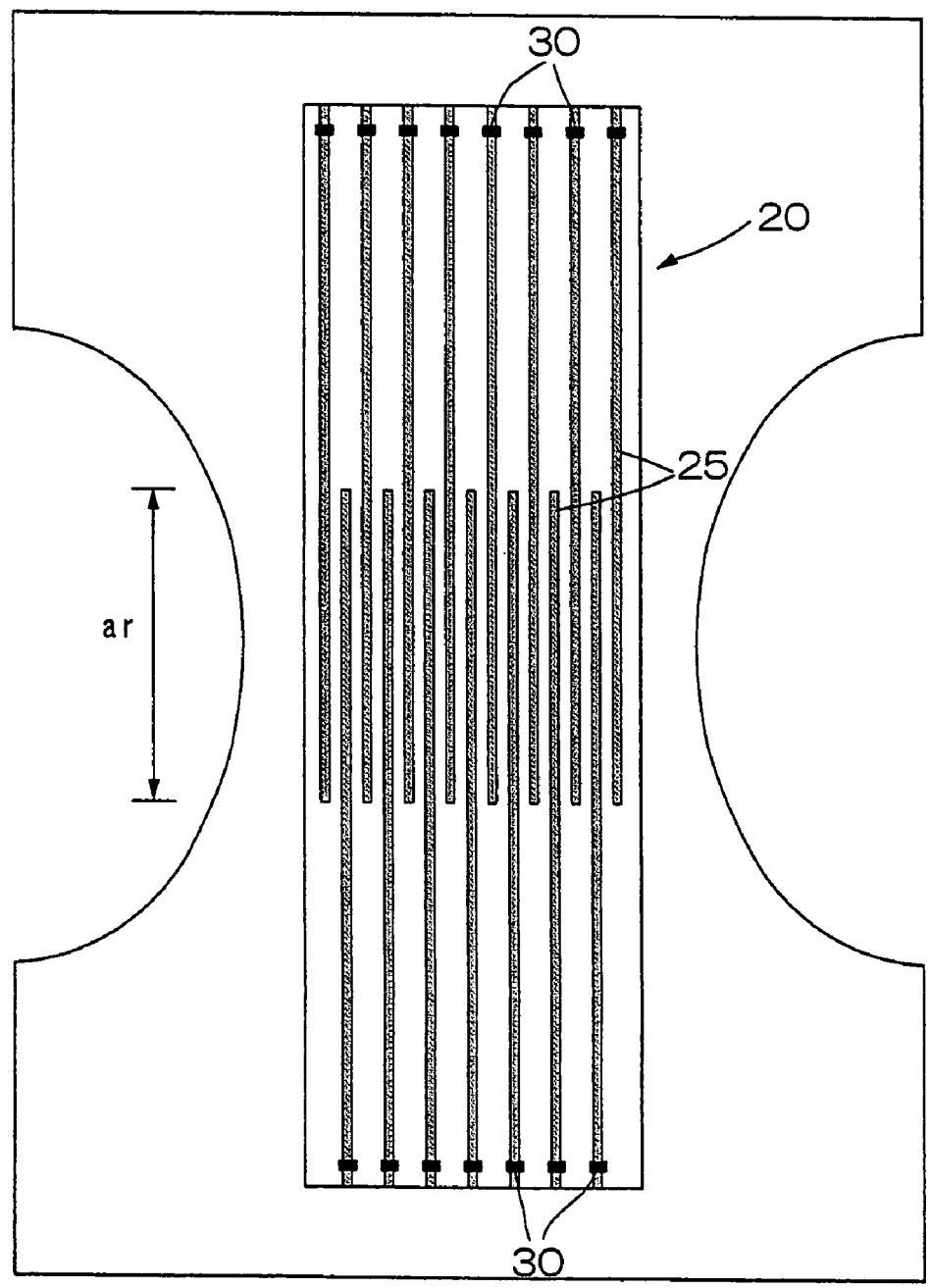
FIG. 39 is a plan view showing another arrangement example of the absorbent member.
Figure 40:
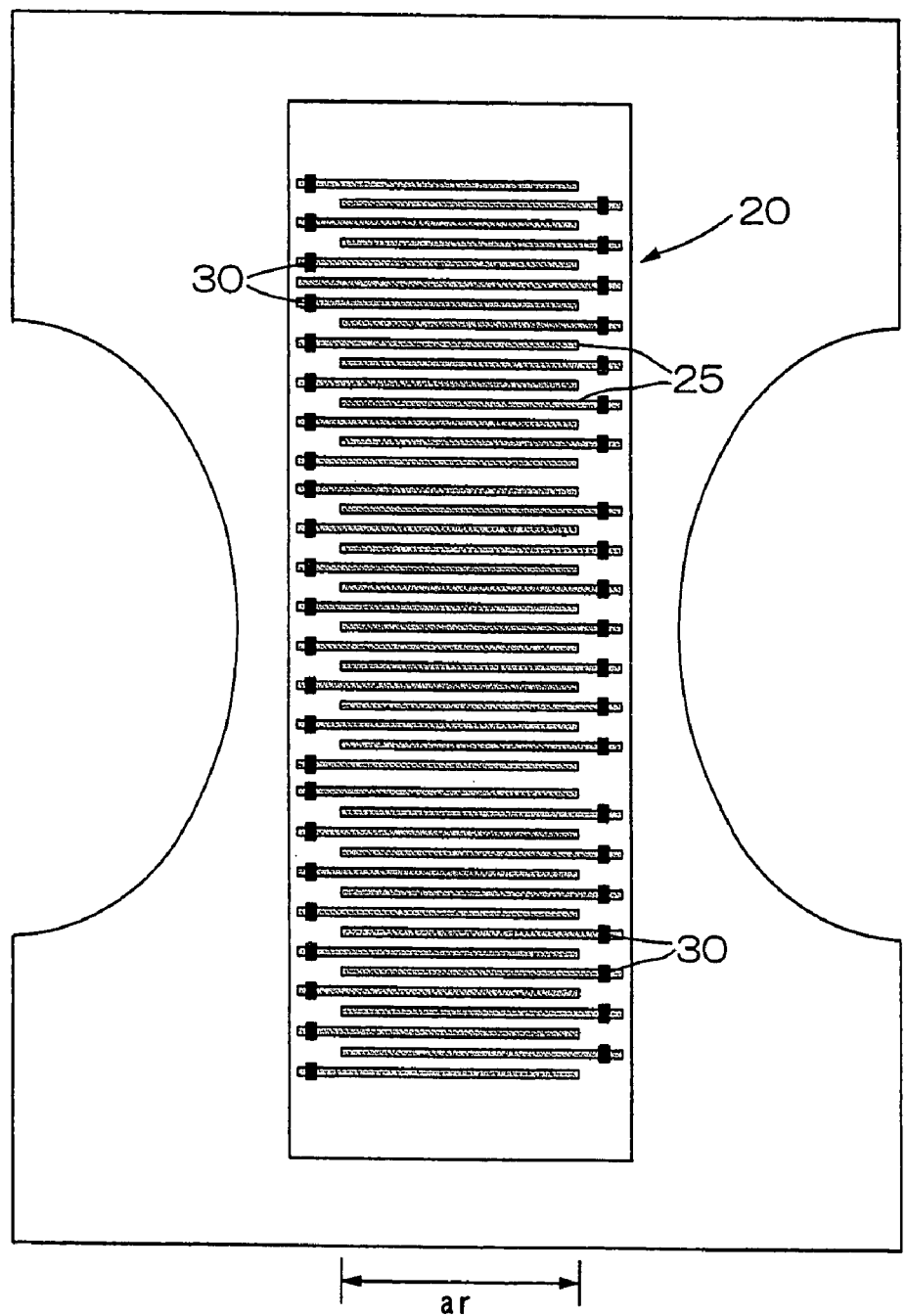
FIG. 40 is a plan view showing another arrangement example of the absorbent member.

In the case of the staggered arrangement of the fixing part 30, a plurality of the absorbent members 25 having the fixing part 30 on one side and a plurality of the absorbent members 25 having the fixing part 30 on the other side may be composed so as to overlap side by side only at an excretion area ar as shown in FIG. 39 (an example in which the absorbent members 25 are arranged along the longitudinal direction of the product) and FIG. 40 (an example in which the absorbent members 25 are arranged along the width direction of the product). In this case, the absorbent members 25 each may be arranged intensively in the excretion area as well as the length of the absorbent members 25 may be shortened, allowing a reduction in the material cost.

7.4 Arrangement Example 4

Figure 41:
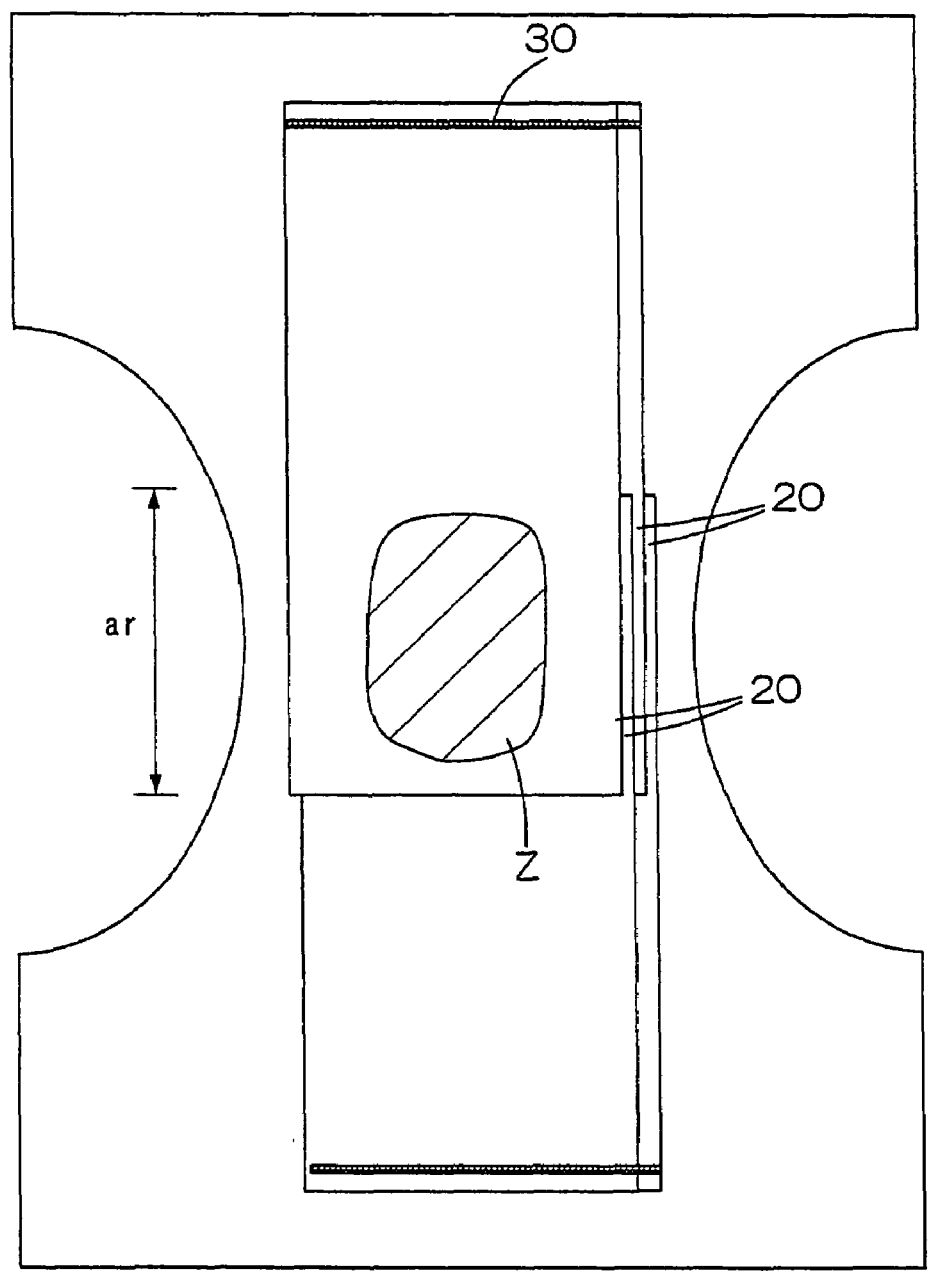
FIG. 41 is a plan view showing another arrangement example of the absorbent member.

Particularly as shown in FIG. 41, when a plurality of the absorption bodies for body fluids 20, 20 in a wide sheet shape (the absorbent members 25 in the case where the absorption bodies for body fluids comprise the absorbent members 25 only) are multi-layered, it is preferable that the free ends of the absorbent members 25 are multi-layered so as to be overlaid in the excretion area ar in a staggered arrangement, as well as the fixing parts 30 are arranged at the ends of the non-overlying sides respectively. In this case, all members constituting the absorption body for body fluids 20 are united.

Figure 42:
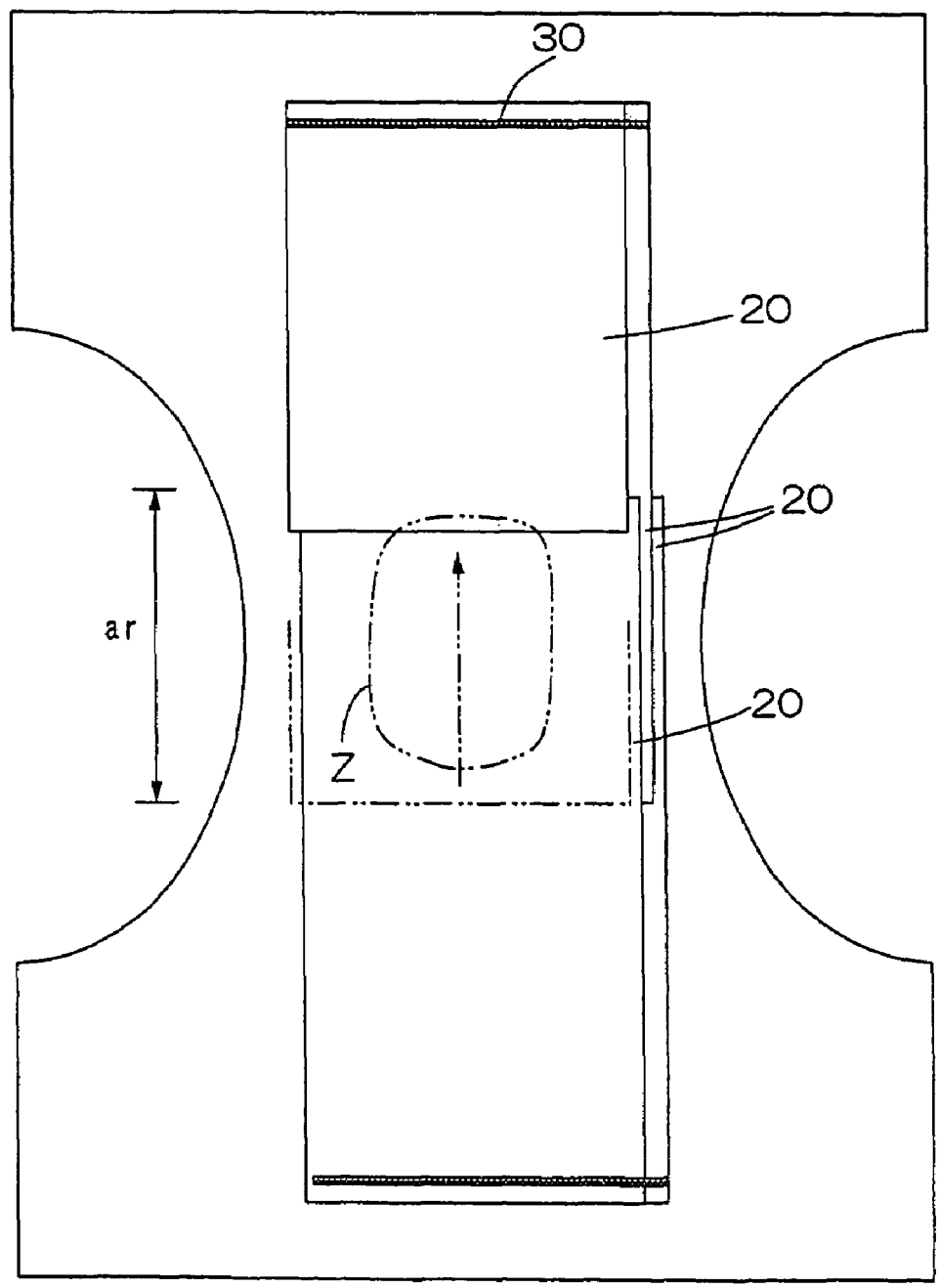
FIG. 42 is a plan view showing another arrangement example of the absorbent member.
Figure 43:
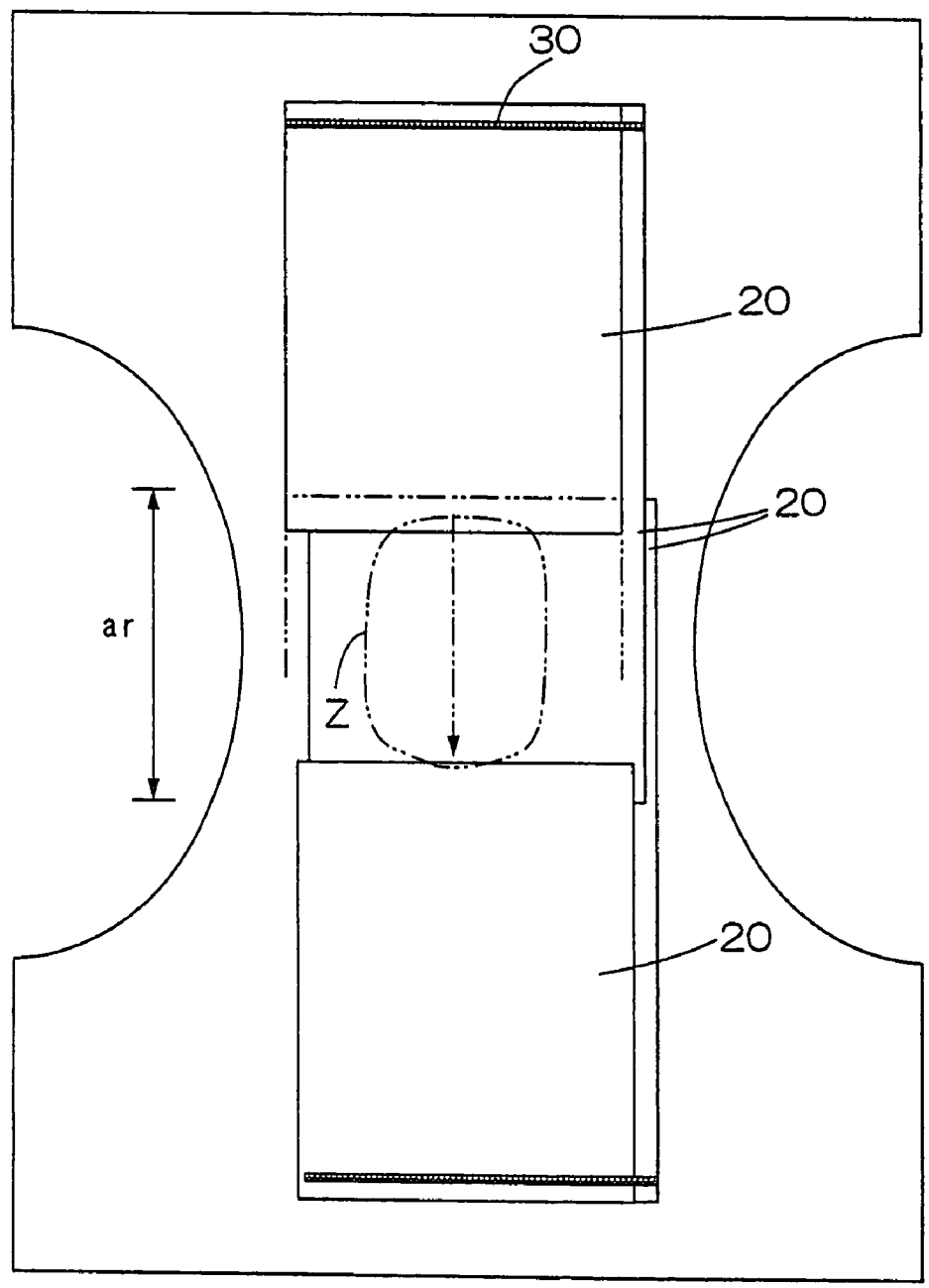
FIG. 43 is a plan view showing another arrangement example of the absorbent member.

In this way, whenever there is excretion in the zone Z of the absorption body for body fluids 20 which is exposed to the excretion area ar, the absorption body for body fluids 20 is dislocated toward the fixing part 30, and the underlying new surface of the absorption body for body fluids 20 may appear in turn as illustrated in FIG. 42 and FIG. 43. In order to explain this function, it should be noted that the absorption bodies for body fluids 20 are illustrated in a state where the absorption bodies for body fluids are displaced from one another to the width direction in FIGS. 41 to 43.

7.5 Arrangement Example 5

Figure 44:
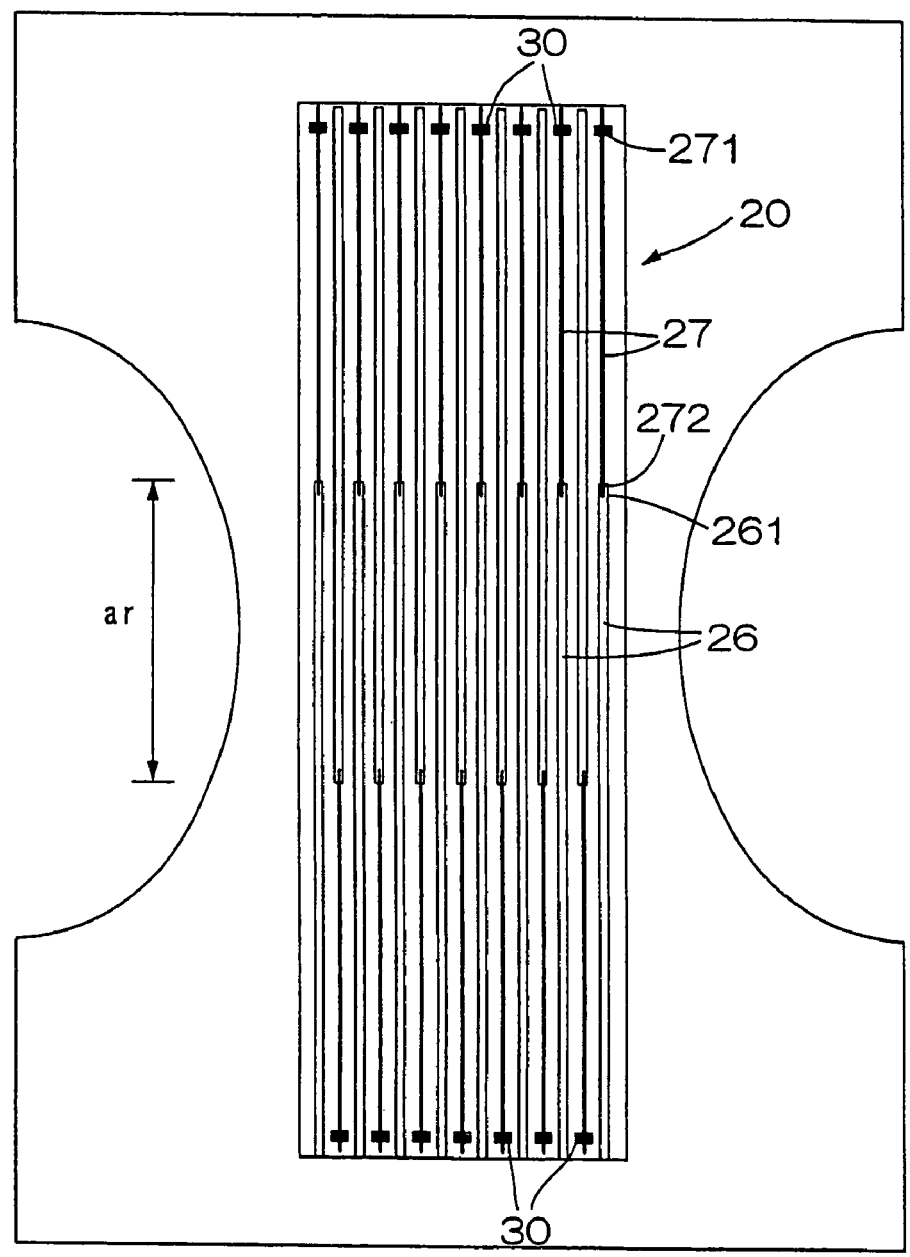
FIG. 44 is a plan view showing another arrangement example of the absorbent member.
Figure 45:
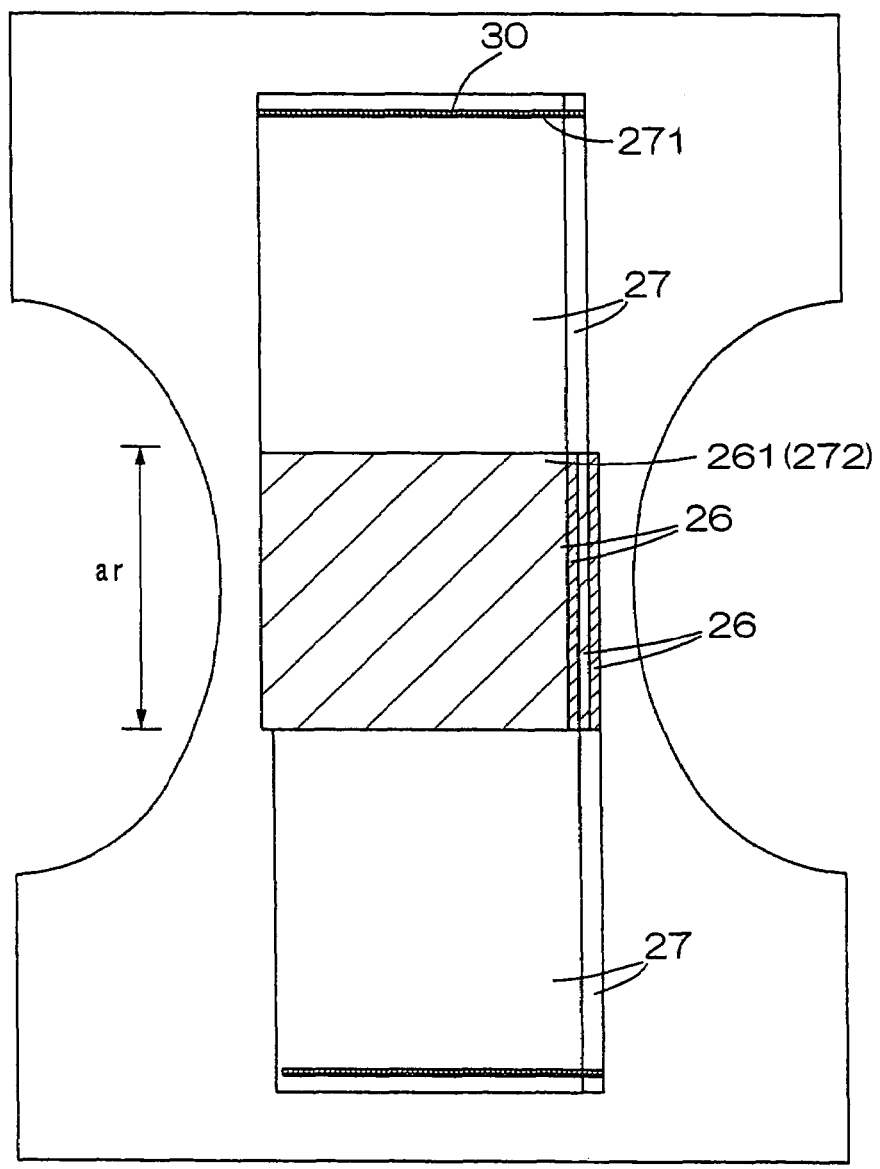
FIG. 45 is a plan view showing another arrangement example of the absorbent member.

In the present invention, the contraction material 27 may be either extended to the entire longitudinal direction of the absorbent material for body fluids 26 or constructed such that one end 271 of the contraction material 27 is fixed at a predetermined place such as the longitudinal end part of the product and the other end 272 opposite to the fixing part 30 is connected to one end 261 of the absorbent material for body fluids 26 as shown in FIG. 44 and FIG. 45. In this case, the other end of the absorbent material for body fluids 26 may preferably be extended over the excretion area ar up to the other longitudinal end of the product. Although not illustrated, the fixing part 30 is not in the staggered arrangement as shown but it may be arranged only at one side of the article as shown in FIG. 36 or the like.

It should be noted that the construction design of separable bonding of the contraction material 27 to the absorbent material for body fluids 26 is not applicable in this embodiment. Further, the contraction material 27 is present only on the side of the fixing part 30 and body fluids is not supplied directly to the contraction material 27, and therefore it is desirable to combine this embodiment with the embodiment in which body fluids diffuse excellently to the contraction direction as in the case of the second to the fourth embodiments.

7.6 Arrangement Example 6

Figure 46:
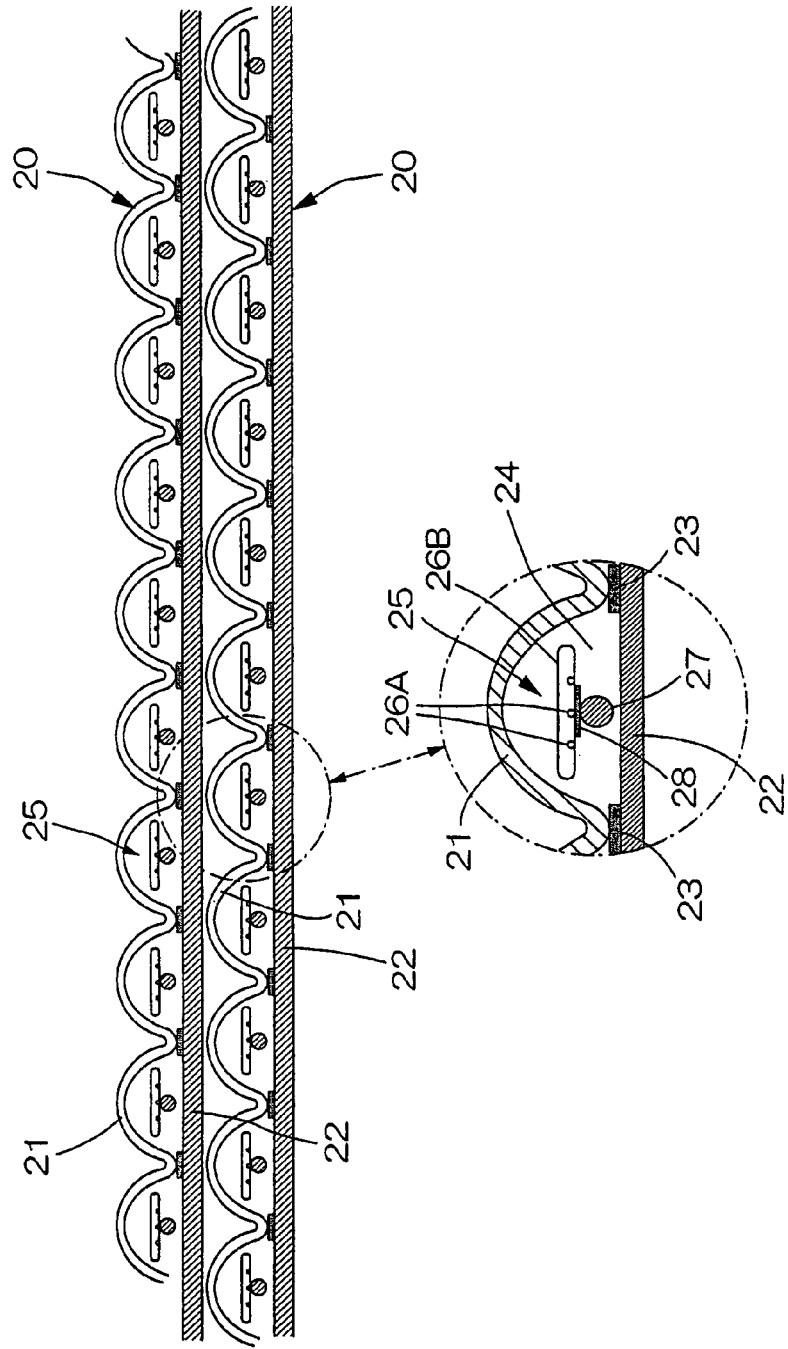
FIG. 46 is a cross sectional view of a main part showing another arrangement example of the absorbent member.

On the other hand, as illustrated in FIG. 46, the absorption body for body fluids 20 (the absorbent members 25 in case where the absorption bodies for body fluids comprise the absorbent members 25 only) may be multilayered in two or more layers as required. In this case, it is desirable that the upper and lower layers are not placed identically but displaced by one half pitch to avoid overlying on each other. Although not illustrated, the absorption bodies for body fluids, 20 and 20, provided with one or more absorbent members 25 may be arranged side by side or multilayered.

7.7 Arrangement Example 7

In the embodiment where one end 30 of the absorbent member 25 is fixed to the article, the absorbent members 25 contract toward the fixing part 30 of the article concurrently with absorption of body fluids. This contraction proceeds gradually, accompanying absorption of body fluids. Accordingly, there is the possibility that sufficient absorption of body fluid may not be achieved, unless the liquid-retaining member LK is always present at the place where the absorbent member 25 shifts by contraction.

Figure 47:
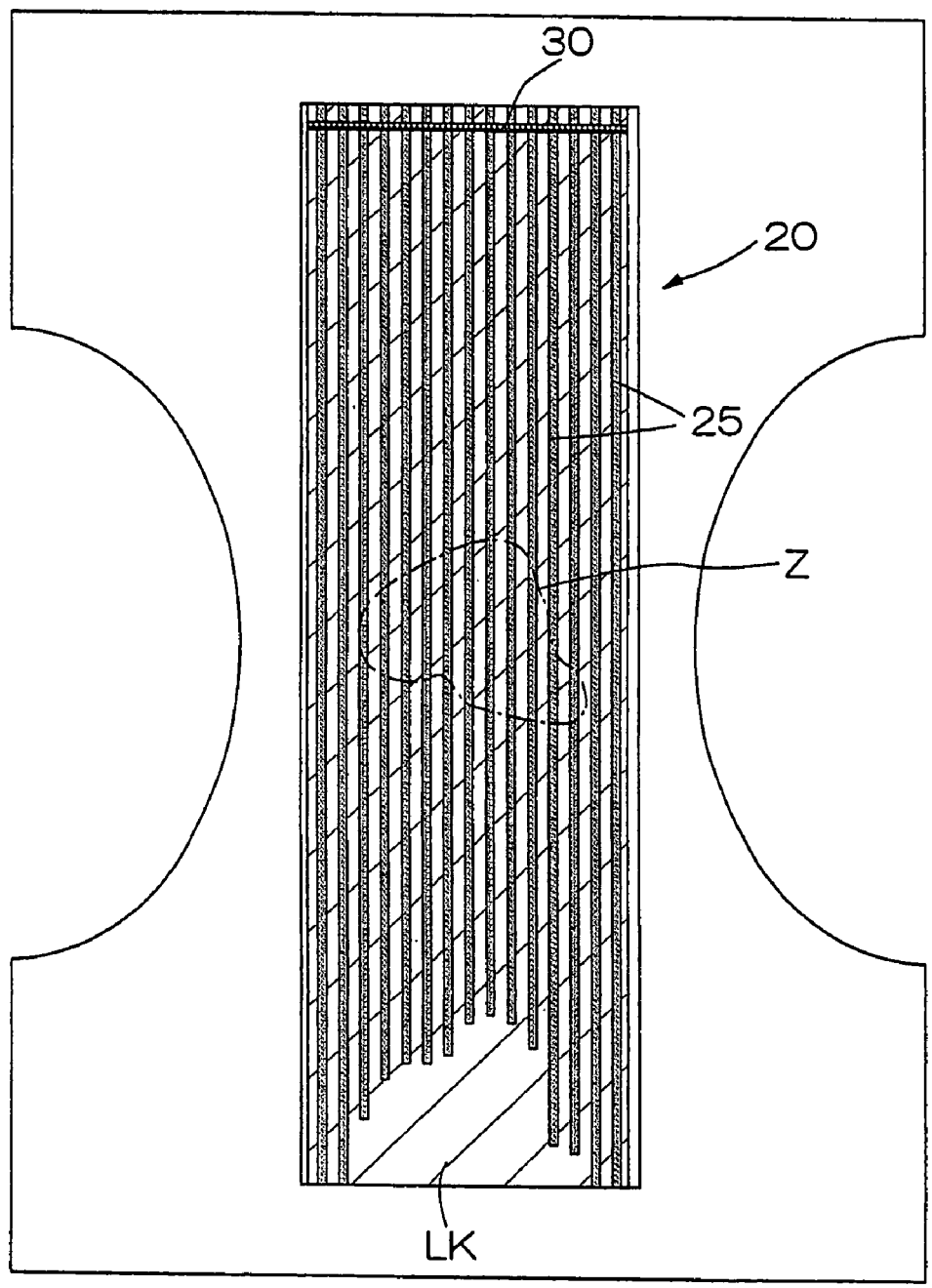
FIG. 47 is a plan view showing an arrangement example of the liquid-retaining member.

For this reason, the liquid-retaining member LK may be arranged so as to cover the entire contraction direction of the absorbent member 25, as shown in FIG. 47. However, in this case, the part Z where body fluids are excreted always remains approximately at the same position, yielding useless non-functional parts. Also in this case, there is the possibility that body fluids are diffused by the liquid-retaining member LK to extend to the part where body fluids are later to be absorbed for contraction, resulting in a reduction of absorption function as well as contraction function when said part absorbs body fluids later.

Figure 48:
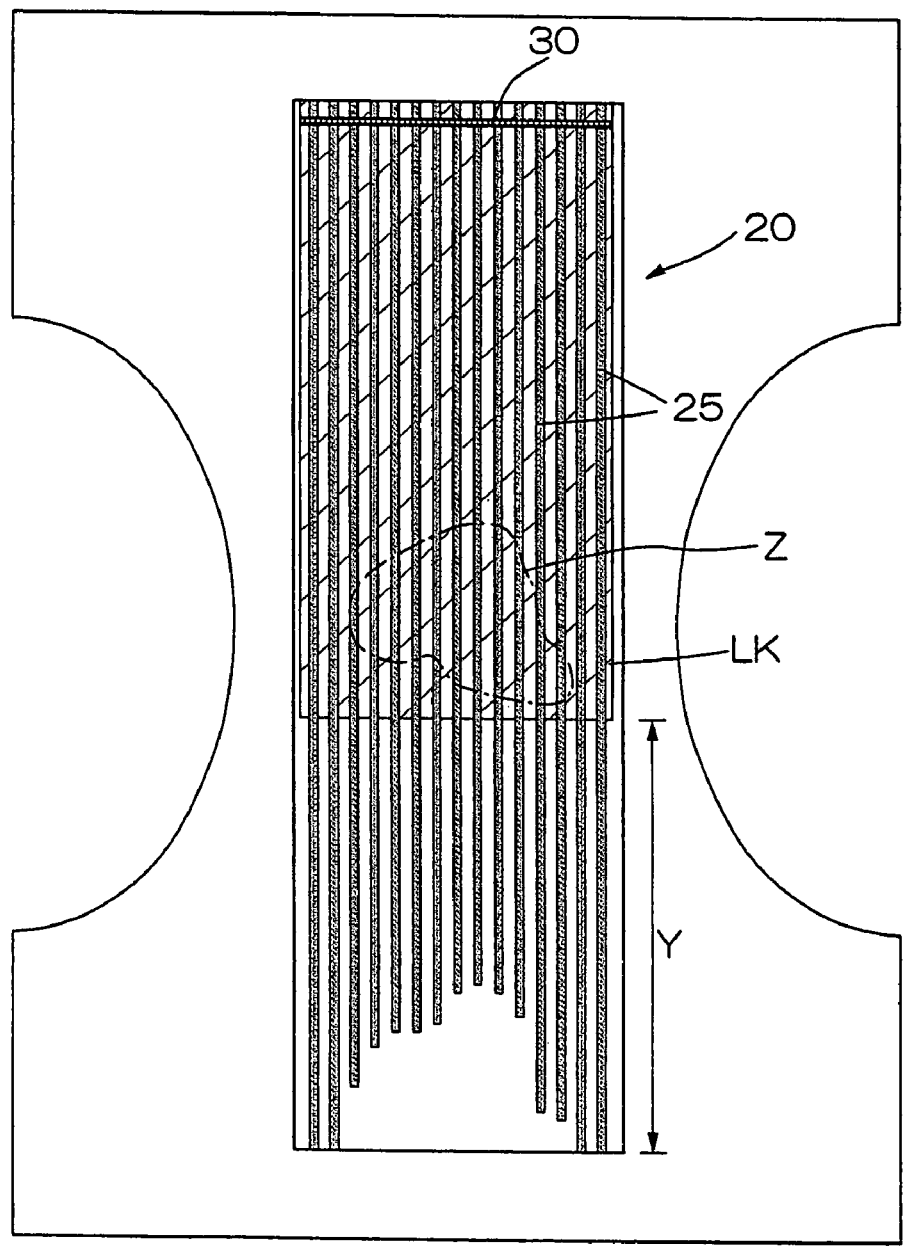
FIG. 48 is a plan view showing another arrangement example of the liquid-retaining member.

Accordingly, the liquid-retaining member LK is more preferably located unevenly on the side of the fixing part 30 of the absorbent member 25, particularly located only from the fixing part 30 to the position Z corresponding to the excretory organ of body fluids (for example, urination part) as shown in the FIG. 48. In this way, when the absorbent member 25 is dislocated by contraction, there is always the liquid-retaining member LK at the newly dislocated place, thereby allowing continuous supply of body fluids to the absorbent member 25 and enough contraction of the absorbent member 25. Further, the other end part Y of the absorbent member 25 corresponding to the part not provided with the liquid-retaining member LK is drawn to be moved to the part corresponding to the liquid-retaining member LK by the contraction of the part of the absorbent member 25 on the side of the fixing part 30 and may be contracted upon absorbing body fluids later while it is being supplied with body fluids from the liquid-retaining member LK, thereby allowing an efficient renewal. Furthermore, the length of the liquid-retaining member LK is controlled to the minimum and the cost-reduction is achieved by such construction. In particular, when the liquid-retaining member LK is arranged only from the fixing part 30 of the absorbent member 25 up to the position Z corresponding to the excretory organ of body fluids (for example, urination part), body fluids hardly diffuse to the other end part Y not provided with the liquid-retaining member LK, resulting in less possibility that absorption function as well as contraction function is reduced when said part Y absorbs body fluids later.

On the other hand, a plurality of separate liquid-retaining members LK of the present invention may be arranged correspondingly to each absorbent member 25 as shown in the aforementioned FIG. 26 and so on, while as shown in FIG. 47 and FIG. 48, the liquid-retaining members LK may be constructed so as to cover the entire area arranged with a plurality of the absorbent members 25.

8 Production Method of the Absorbent Article for Body Fluids

Further, the objective absorbent article of the present invention is generally continuously produced, on the production line, by attaching its parts so as to be stacked in turn beginning with the lower layers. In the production of the article having the contracting absorbent member of the present invention, although not illustrated, the absorbent member 25 is prepared in bulk sample in advance, cut into a predetermined length one after another, arranged on an objective attachment part, specifically on an appropriate place of the liquid-impermeable back-surface side sheet 22 of the aforementioned examples, moving down on the production line, and then fixed at the fixing part 30 as needed.

The absorbent member 25 produced in advance on a separate line and wound on a roll may be set on an assembly line or the production line of the absorbent member 25 may be connected to the assembly line to omit the winding process.

Particularly when the pouch-like carrier 26B is arranged in the folded state, the absorbent member 25 still being in an unfolded state is desirably attached while it is being folded in the width direction at the time of attaching to the objective part.

And more particularly, in the case the absorbent member 25 having the aforementioned expandable pouch-like carrier 26B is arranged in the folded state, it is possible to adopt a method in which the absorbent member 25 is attached to the objective part for attachment while the absorbent member 25 is being folded in the width direction orthogonal to the contraction direction of the absorbent member 25 or tucks are being formed on the pouch-like carrier 26B. Prior to the folding in this instance, a plurality of the seal parts, s1, s1..., formed by bonding the surfaces facing to each other in the thickness direction of the pouch-like carrier 26B in a continuous linear manner from one end to the other end of the width direction may be provided with a spacing in-between in the contraction direction of the absorbent member 25. In thus-formed absorbent member 25, the inner space of the pouch-like carrier 26B is partitioned by the seal parts, S1, S1..., while the lateral expansion is not restrained at the time of swelling of the absorbent member 25.

In contrast, in order to restrain the lateral expansion of the absorbent member 25, a plurality of the seal parts, S1, S1..., formed by bonding the surfaces facing to each other in the thickness direction of the pouch-like carrier 26B in a continuous linear manner from one end to the other end of the width direction are provided with a spacing in-between in the direction of contraction of the absorbent member 25 after having folded or tucked the absorbent member 25.

9 Examples

9.1 Experiment 1: Experiment to Confirm the Renewal Function

Example 1-1

A tape-type paper diaper having a form shown in FIG. 1 and FIGS. 23 to 25 where the absorbent member 25 is fixed as in the example shown in FIG. 37 was obtained. The absorbent member 25 makes use of 400 mm-long, 8 mm-wide nonwoven ribbon made of heat melt compound fiber having a basis weight of 18 g/m$^2$ and "Aqua Pearl" made by Mitsubishi Chemical Corporation as the highly water-absorbent polymer 26A, 1 g of which is bonded in a form shown in FIG. 7 to prevent from falling. As the contraction material, four pieces of "Solvron" (250 dtex) made by Nitivy Co. Ltd. were tied in a bundle, twisted 100 times per 1 m, fixed in the absorbent material for body fluids 26 as in the construction shown in FIG. 7, and used.

Comparative Example 1-1

As the absorbent body for body fluids, the following was used according to a conventional form in place of the absorbent body 20 of the embodiment: 12 g of flap pulp and 9 g of "Aquapearl" made by Mitsubishi Chemical Co. Ltd. as the highly water-absorbent polymer 26A are mixed approximately uniformly and laminated to form 400 mm-long, 150 mm-wide sheet, which is wrapped with a 400 mm-long, 340 mm-wide crepe paper with a basis weight of 19 g/m$^2$ to prevent the highly water-absorbent polymer 26A from falling.

(Test and Result)

Figure 49:
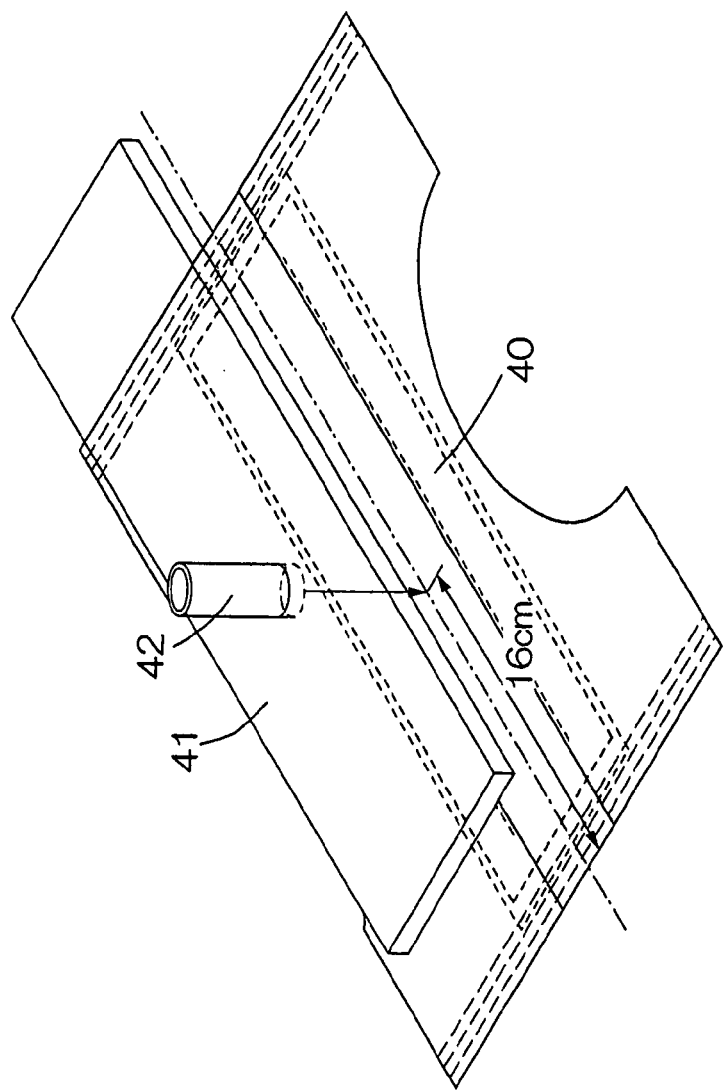
FIG. 49 is a perspective view showing a manner of testing for Experiment 1.

As shown in FIG. 49, a paper diaper 40 was placed in a horizontal position, an acrylic plate 41 having an injection cylinder 42 was placed over it, and the injection cylinder 42 was set on the centerline of the paper diaper 40 at a distance of 16 cm from the edge of the front body.

1) Measurement of absorption rate: under these conditions, the absorption time (second) required for absorbing completely 60 ml of artificial urine through the injection cylinder 42 was determined as the absorption rate. After left standing for 30 minutes, again 60 ml of the artificial urine was injected and allowed to be completely absorbed. After left standing for further 30 minutes, once again 60 ml of the artificial urine was injected and each absorption rate was determined for these operations.

2) Moving distance from injection place of artificial urine: The position at a distance of 16 cm from the edge of the front body was marked and 60 ml of artificial urine was injected into the injection cylinder 42 as in the case of the measurement of the absorption rate, and the moving distance from the marked position was determined every time the measurement of the absorption rate was measured.

3) Area renewal rate: At the time of measuring the absorption rate, an absorption area of the artificial urine was marked right after 60 ml of the artificial urine had been completely absorbed ("initial absorption area"). After left standing for 30 minutes from the time when the artificial urine was completely absorbed, an absorption area remaining in the "initial absorption area" ("remaining absorption area") was marked and subjected to an image analysis. The "remaining absorption area" was marked in the same way after the second and third measurements of the absorption rate and subjected to the image analysis. The area renewal rates were determined by the following equation (2):

$$\text{Area renewal rate} = (\text{"initial absorption area"} - \text{"remaining absorption area"}) / \text{"initial absorption area"} \quad (2)$$

These results are shown in Table I. From these results, it is found that the absorbent body for body fluids of the present invention is rapid in the absorption rate, large in the moving distance of urine and capable of renewing the absorption part. It is apparent from these results that, in the diaper prepared according to the present invention, prompt absorption can be achieved without a decrease in absorption even if excretion is repeated several times in the absence of occurrence of gel blocking, since the highly water-absorbent polymer not absorbing water is newly brought to the absorption part due to the contraction of the absorbent member on absorbing water.

TABLE I

| Measurement item | Example 1-1 | | | Comparative example 1-1 | | |
|---|---|---|---|---|---|---|
| (Unit) | 1st | 2nd | 3rd | 1st | 2nd | 3rd |
| Absorption rate (second) | 3 | 4 | 4 | 6 | 12 | 30 |
| Moving distance of artificial urine (cm) | 7 | 6 | 5 | 0 | 0 | 0 |
| Area renewal rate (%) | 90 | 70 | 50 | 0 | 0 | 0 |

Figure 50:
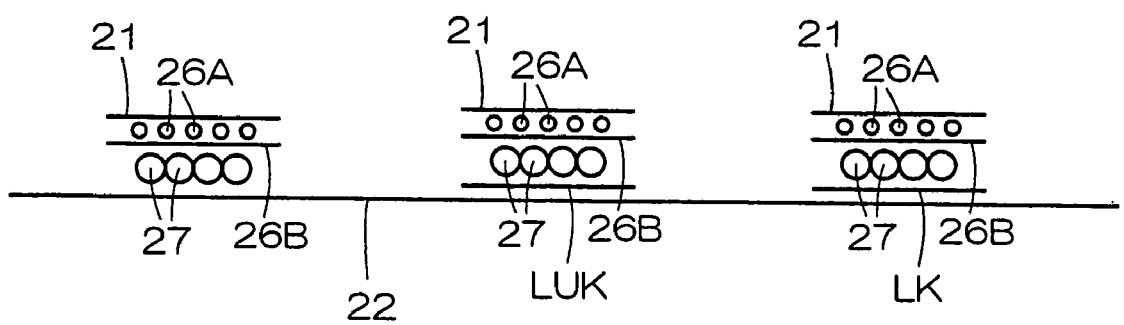
FIG. 50 is a cross sectional view of each main part of samples in Experiment 2 shown schematically.

TABLE I-continued 9.2 Experiment 2: Experiment to Confirm Effect of Liquid-retaining Member 9.2.1 Verification of Effect of Liquid Retention As shown in FIG. 50, samples A to C were placed side by side on a single liquid-impermeable back sheet material 22 (made of polyethylene plastic film) and the effect of liquid retention of liquid-retaining members was compared and verified. The absorbent member 25 of each sample is multi-layered with the contracting material (brand name "Solvron" made by Nitivy Co. Ltd.) 27, the carrier (made of crepe paper) 26B, the highly absorbent polymer and the use-surface side sheet 21 in this order. One end of the multilayered absorbent member of each sample was fixed to the back sheet material 22, and the above absorbent members have an identical length to one another (length in the direction orthogonal to the face of FIG. 50). In this case, the highly absorbent polymer was made continuous by a section of 10 mm-length and arranged intermittently with a space of 20 mm in the longitudinal direction.

It should be noted that the sample A is a comparative example in which no liquid-retaining member is arranged, the sample B is a comparative example in which crepe paper (not liquid-retaining member) LUK was interposed (unfixed) between the contraction material 27 and the back sheet material 22, and the sample C is an example in which hydrophilic spun bond non-woven fabric LK was interposed (unfixed) between the contraction material 27 and the back sheet material 22 as the liquid-retaining member.

When artificial urine was dropped onto an approximate center of the longitudinal direction of each sample, the sample A contracted by 28 mm with a contraction percentage of 10%. On the other hand, the sample B contracted by 18 mm with a contraction percentage of 6% and the sample C contracted by 72 mm with a contraction percentage of 25% from these results, it was found that the arrangement of the liquid-retaining member of the present invention enhanced the contraction efficiency strikingly owing to its liquid-retaining property.

Figure 51:
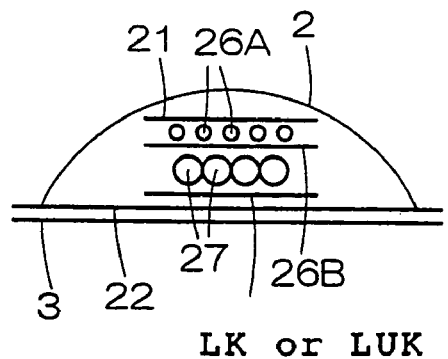
FIG. 51 is a plan view of another sample in Experiment 2.

9.2.2.Verification of effect of liquid-retaining member on reducing wet frictional force As show in FIG.51, the example 2-1 is contact the liquid-impermeable back sheet material 22, the liquid-retaining member (hydrophilic spun bond nonwoven fabric) LK, the contraction material (band name "Solvron" made by Nitivy Co. Ltd.) 27, the cattier (made of crepe paper) 26B, the highly absorbent polymer and the use-surface side sheet 21 were layered in these order, and one end of the absorbent member except the liquid-retaining member LK was fixed to the back sheet material 22, and the comparative example 2-1 was constructed in the same way as that in the experiment 2-1 except that the liquid-retaining member LK was replaced with the non-liquid-retaining member LUK (crepe paper). An appropriate Place of each of the example 2-1 and the comparative example (2-2) was wetted with artificial urine to allow it to be contracted and the frictional force on wetting between the liquid-retaining member LK of the non-liquid-retaining member LUK and the liquid-impermeable back sheet material 22 was measured. In the case, the highly absorbent polymer was made continuous by a section of 10 mm-length and arranged intermittently with a space of 20 mm in the longitudinal direction.

Figure 52:
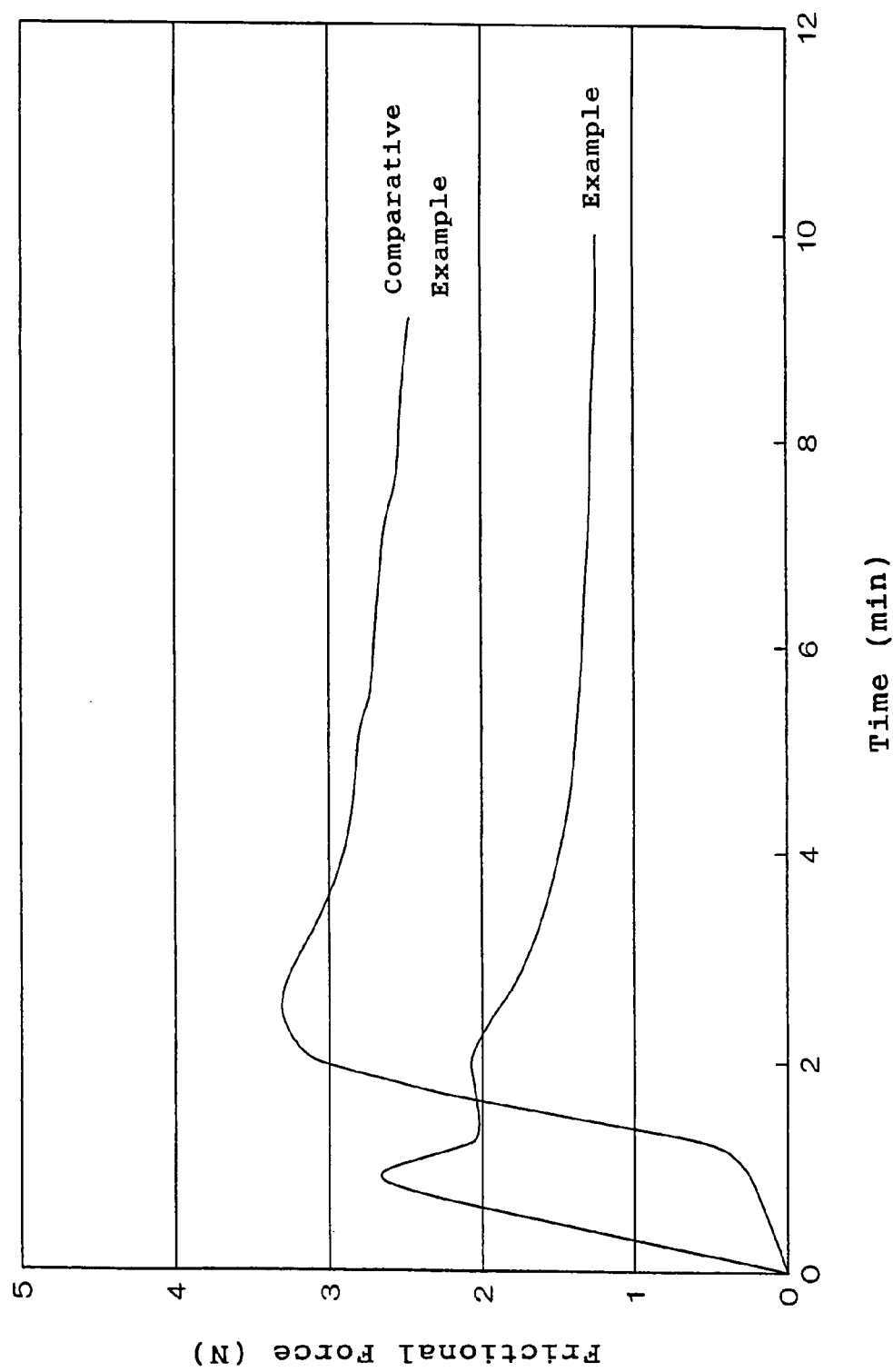
FIG. 52 is a graph showing test results of Experiment 2.

As the result, the frictional force at the time of contraction was strikingly reduced in the example 2-1 which was provided with the liquid-retaining member LK concerned with the present invention when compared to that in the comparative example 2-2 as shown in FIG. 52.

9. 3 Experiment 3: Experiment to Confirm Effect of Cushion Member

Figure 53:
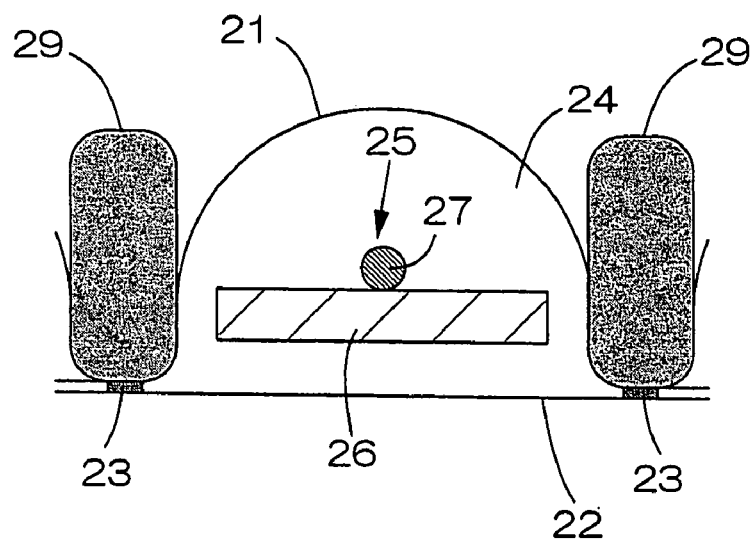
FIG. 53 is a cross sectional view of a main part of a sample in Experiment 3.

As shown in FIG. 53, the absorbent body for body fluids 20 of the present invention was constructed such that the use-surface side sheet 21 and the back-surface side sheet 22 were overlaid, the fixing parts 23 were formed along the longitudinal directional at places spaced in the width direction of the product, the channel space 24 were formed along the longitudinal direction between the adjacent fixing parts, 23 and 23, the absorbent member 25 in which the contraction material 27 was fixed on the absorbent material 26 having 3 cm-width is arranged within each channel space, 24, 24 . . . , and the cushion members, 29 and 29, made by putting the highly absorbent polymer in the pouch-like body were arranged on the upper side (outer side) of the use-surface side sheet 21 at places corresponding to the fixing parts 23.

The cushion member 29 had the partitions 27d along the vertical direction as shown in the aforementioned FIG. 35, and was prepared so that the partitions were not to be removed (example 3-1) of the partitions 27d (29d??) were to be removed (example 3-2) By contacting body fluids.

In addition, the absorbent body for body fluids devoid of and cushion members 29 was prepared as the comparative experiment 3-1 (not illustrated).

Figure 54:
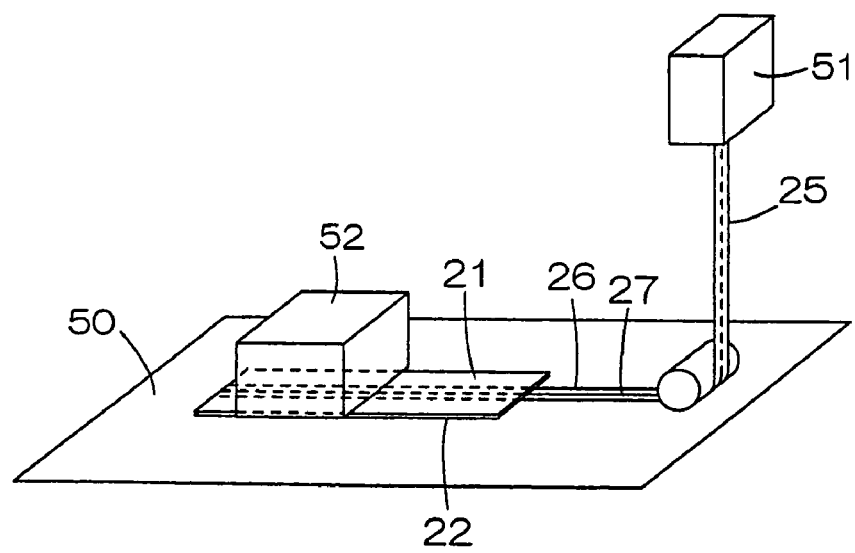
FIG. 54 is a perspective view showing a manner of testing for Experiment 3.

After artificial urine was absorbed by each absorbent body for body fluids of the examples 3-1 and 3-2 and the comparative example 3-1, the absorbent body was place on a level surface 50, only one end of the absorbent 25 was fixed to the chuck of a tensile tester 51, and a weight 52 was placed on the use-surface side sheet 21 so that a pressure of 50g/cm$^2$ may be applied to the other end of the absorbent 25 as shown in FIG. 54. The tensile test was carried out at a cross head speed of 300 mm/min. and the moving resistance of the absorbent 25 against the sheets 21 and 22 was measured.

In addition, without tensioning, the area renewal rates of the absorbent material for body fluids 26 (the ratio of the area renewed with the new absorbent material for body fluids to the area wetted by dropping artificial urine) were measured.

These results are shown in Table II.

TABLE II

|  | Moving resistance (g) | Pressurized area renewal rate (%) |
|---|---|---|
| Example 3-1 | 950 | 76 |
| Example 3-2 | 250 | 92 |
| Comparative example 3-1 | 1500 | 23 |

Figure 55:
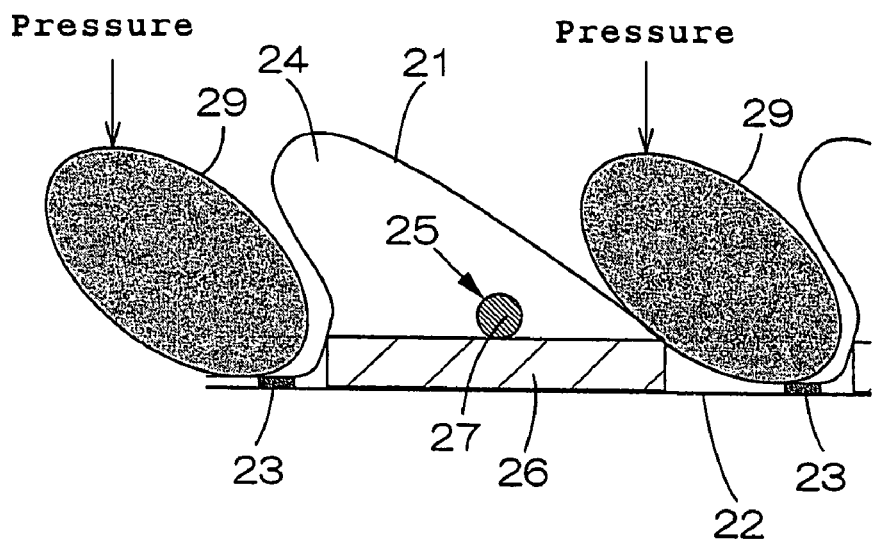
FIG. 55 is a cross sectional view of the main part showing a state of the sample after testing in Experiment 3.
Figure 56:
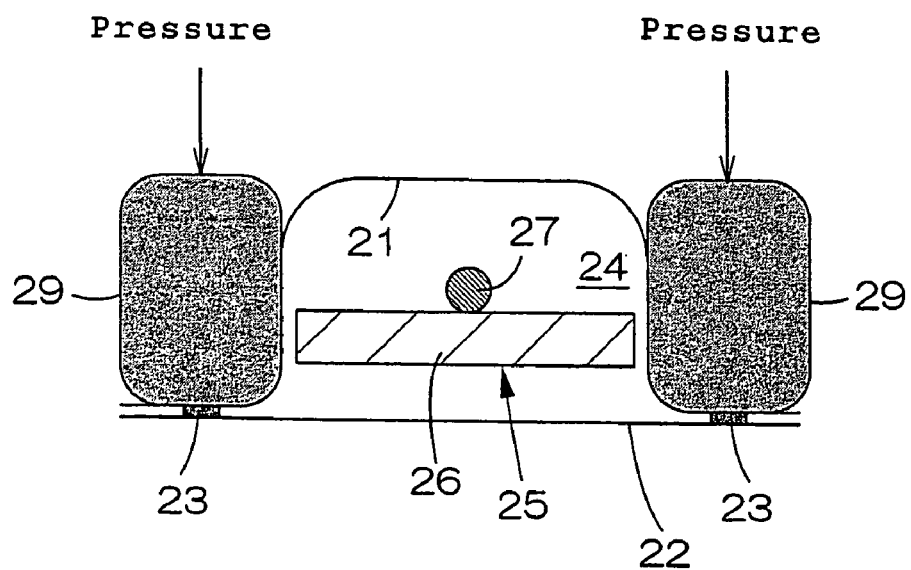
FIG. 56 is a cross sectional view of a main part showing a state of a sample of the present invention after testing in Experiment 3.

From these results, it was found that the moving resistance of the absorbent member 25 was significantly reduced by arranging the cushion members 29. And particularly in the example 2 provided with the removable partitions, the moving resistance was extremely lowered. When the cross sections of the example 3-1 and the example 3-2 were observed after the tensile test, only the part of the cushion member 29 that absorbed body fluids swelled entirely, forming the cross section in an unstable oval-like shape in the example 3-1 as shown in FIG. 55. Consequently, the cushion members 29 fell sideways and pressed the absorbent member 25 with sandwiching it. On the other hand, in the example 2 (3-2??) as shown in FIG. 56, the part which absorbed body fluids in the cushion member 29 was in a stable rectangular-like shape of the cross section corresponding to the external pressure and did not fall sideways, because the highly absorbent polymer in its inside could move freely owing to the removal of the partitions.

Figure 57:
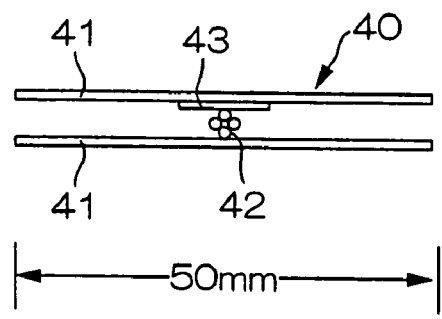
FIG. 57 is a cross sectional view of a sample in Experiment 4.
Figure 58:
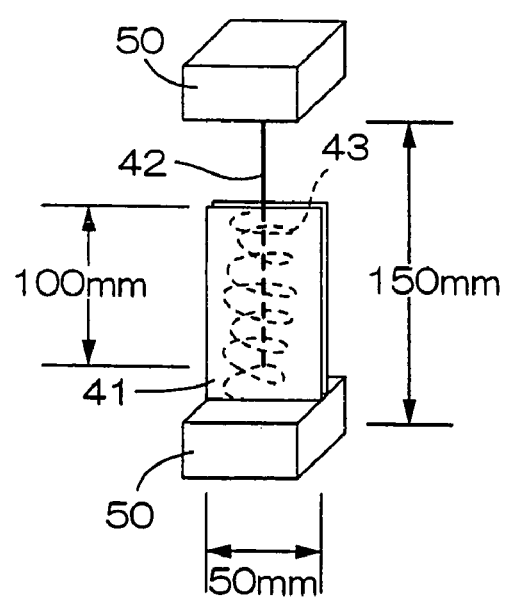
FIG. 58 is a perspective view of a manner of testing for Experiment 4.

9.4 Experiment 4: Experiment to confirm effect of separation of contraction material from absorbent material for body fluids 9.4.1 Separation Test As shown in FIG. 57, a sample sheet 40 was prepared such that a contraction material 42 (thickness; 1100 dtex) made of "Solvron", a brand name of the product of Nitivy Co. Ltd., was arranged between belt-like nonwoven fabrics, 41 and 41, having a 50 mm-width along the longitudinal direction so that the upper end portion of the contraction material 42 might protrude from the upper end of the nonwoven fabrics and the lower end of the contraction material 42 might not reach the lower end of the nonwoven fabrics as shown in FIG. 58, and a variety of hot melt adhesives 43 were applied in a spiral fashion. The adhesives were applied in a length range of 100 mm. As the hot melt adhesives 43, three kinds of water dispersion-type hot melt adhesives (examples 4-1 to 4-3) and one water nondispersion-type hot melt adhesive (comparative example 4-1) were used.

As shown in FIG. 58, the upper end of the contraction material 42 protruding from the sample 40 and the lower end of the nonwoven fabric having no contraction material 42 were inserted in the chucks, 50 and 50, of the tensile tester respectively, and the bond strength between the contraction material 42 and the nonwoven fabric was measured. The distance between the two chucks was adjusted to 150 mm and the cross head speed was 300 mm (mm/min??). The measurements were carried out under the conditions in which the samples were in a dry state and in a wet state made by wetting at the bonding part of the sample by artificial urine. The measurement results are shown in Table III.

TABLE III

|  | Bond strength in dry state (gf) | Bond strength in wet state (gf) |
|---|---|---|
| Example 4-1 | 2800 | 40 |
| Example 4-2 | 1670 | 32 |
| Example 4-3 | 2470 | 113 |
| Comparative example 4-1 | 2750 | 2530 |

9. 4. 2 Confirmation Test of Contraction Efficiency

Using the same water dispersion-type hot melt adhesives and water nondispersion-type hot melt adhesive as those in the above separation test, diapers in the same form as that in the experiment 1 were prepared. Examples having used the former adhesives were referred to as examples 4-4 to 4-6, and an example with the latter adhesive was referred to as comparative example 4-2. Two hundred ml of artificial urine was dropped twice onto diapers of each example and the area renewal rates of the absorbent material for body fluids 26 (the ratio of the area renewed by new absorbent material for body fluids to the area wetted by dropping artificial urine) were measured. These measurement results are shown in Table IV.

TABLE IV

| | First area renewal rate (%) | Second area renewal rate (%) |
|---|---|---|
| Example 4-4 | 91 | 74 |
| Example 4-5 | 94 | 69 |
| Example 4-6 | 92 | 77 |
| Comparative example 4-2 | 24 | 13 |

From these results, it was found that the area renewal rate was much higher in the examples 4-4 to 4-6 where the bonging part between the contraction material 27 and the absorbent material for body fluids 26 may be removed by contacting body fluids compared to that of the comparative example 42 where there is no such removal, demonstration an efficient contraction capability of the absorbent material for body fluids 26 in the former examples.

What is claimed is:

1. An absorbent article for body fluids capable of absorbing and retaining body fluids, the absorbent article comprising:
    an absorbent member which contracts on contacting body fluids;
    wherein the absorbent member comprises a contraction material having a predetermined length and contracting on contacting body fluids and an absorbent material for body fluids practically united with the contraction material;
    wherein the absorbent material for body fluids comprises a highly absorbent polymer, a retaining carrier, and the contraction material;
    wherein the highly absorbent polymer of the absorbent member is arranged intermittently on the retaining carrier in the direction of contraction;
    wherein the predetermined length of the absorbent member in the direction of contraction where the highly absorbent polymer is not arranged in the retaining carrier is adjusted to be from 30 to 400% of the length of the absorbent member in the direction of contraction where the highly absorbent polymer is arranged.

2. An absorbent article for body fluids capable of absorbing and retaining body fluids, comprising:
    an absorbent member which contracts on contacting body fluids;
    wherein the absorbent member comprises a contraction material having a predetermined length and contracting on contacting body fluids and an absorbent material for body fluids practically united with the contraction material;
    wherein the absorbent material for body fluids comprises a highly absorbent polymer, a retaining carrier, and the contraction material;
    wherein the highly absorbent polymer of the absorbent member is arranged intermittently on the retaining carrier in the direction of contraction;
    wherein the contraction material is fixed to the absorbent member where the highly absorbent polymer is arranged in the direction of contraction of the retaining carrier and is not fixed to the absorbent member where the highly absorbent polymer is not arranged.

3. An absorbent article capable of absorbing and retaining body fluids, the absorbent article comprising:
    an absorbent member which contracts on contacting body fluids;
    wherein a plurality of cushion members are provided and an absorbent member is arranged between the cushion members;
    wherein the cushion members comprise a shape extending to the longitudinal direction of the product and are arranged in a plurality lines intermittently in the width direction of the absorbent article;
    wherein the cushion members are constructed by enclosing a body fluid-absorbent cushioning material in a closed pouch-like body made of a sheet permeable to body fluids;
    wherein the pouch-like body of the cushion member is partitioned to have a plurality of compartments and the body fluid-absorbent cushioning material is enclosed in these compartments respectively;
    wherein the partitions are constructed so as to be removed on contacting body fluids.

4. The absorbent article of claim 3, wherein the partitions are formed by bonding the inner surfaces of the pouch-like body to each other using a water-dispersion type hot melt adhesive.

5. The absorbent article of claim 3, wherein the partitions are formed by bonding the inner surfaces of the pouch-like body to each other using a water-soluble adhesive.

* * * * *